(12) United States Patent
McBride et al.

(10) Patent No.: US 7,405,320 B2
(45) Date of Patent: Jul. 29, 2008

(54) THERAPEUTIC AND DIAGNOSTIC CONJUGATES FOR USE WITH MULTISPECIFIC ANTIBODIES

(75) Inventors: William J. McBride, Boonton, NJ (US); David M. Goldenberg, Mendham, NJ (US); Carl Noren, Mt. Arlington, NJ (US); Hans J. Hansen, Picayune, MS (US)

(73) Assignee: Immunomedics, Inc., Morris Plains, NJ (US)

( * ) Notice: Subject to any disclaimer, the term of this patent is extended or adjusted under 35 U.S.C. 154(b) by 911 days.

(21) Appl. No.: 10/776,470

(22) Filed: Feb. 11, 2004

(65) Prior Publication Data

US 2005/0002945 A1 Jan. 6, 2005

Related U.S. Application Data

(63) Continuation-in-part of application No. 10/150,654, filed on May 17, 2002, now Pat. No. 7,138,103, which is a continuation-in-part of application No. 09/823,746, filed on Apr. 3, 2001, now Pat. No. 6,962,702, and a continuation-in-part of application No. 09/382,186, filed on Aug. 23, 1999, now Pat. No. 7,052,872, which is a continuation-in-part of application No. 09/337,756, filed on Jun. 22, 1999, now Pat. No. 7,074,405.

(60) Provisional application No. 60/104,156, filed on Oct. 14, 1998, provisional application No. 60/090,142, filed on Jun. 22, 1998.

(51) Int. Cl.
*C07C 229/00* (2006.01)
*A61K 39/00* (2006.01)
*C07K 1/00* (2006.01)

(52) U.S. Cl. .................. 560/41; 424/184.1; 530/403

(58) Field of Classification Search ................. None
See application file for complete search history.

(56) References Cited

U.S. PATENT DOCUMENTS

| | | | |
|---|---|---|---|
| 2,668,165 A * | 2/1954 | Carpenter ............... 530/231 |
| 4,468,457 A | 8/1984 | Goldenberg et al. |
| 4,735,210 A | 4/1988 | Goldenberg |
| 4,737,453 A | 4/1988 | Primus |
| 4,792,521 A | 12/1988 | Shochat |
| 4,818,709 A | 4/1989 | Primus |
| 4,863,713 A | 9/1989 | Goodwin et al. |
| 4,971,792 A | 11/1990 | Steplewski et al. |
| 5,078,998 A | 1/1992 | Bevan et al. |
| 5,101,827 A | 4/1992 | Goldenberg |
| 5,128,119 A | 7/1992 | Griffiths |
| 5,183,756 A | 2/1993 | Schlom |
| 5,225,541 A | 7/1993 | Hackett et al. |
| 5,274,076 A | 12/1993 | Barbet et al. |
| 5,328,679 A | 7/1994 | Hansen et al. |
| 5,336,278 A * | 8/1994 | Adams et al. .............. 44/419 |
| 5,469,854 A | 11/1995 | Unger et al. |
| 5,502,037 A | 3/1996 | Kondratyer |
| 5,503,987 A | 4/1996 | Wagner |
| 5,514,810 A * | 5/1996 | Platzek et al. ............ 548/300.1 |
| 5,534,254 A | 7/1996 | Huston |
| 5,534,756 A | 7/1996 | Huston et al. |
| 5,541,297 A * | 7/1996 | Hansen et al. ............ 530/391.7 |
| 5,591,828 A | 1/1997 | Bosslet et al. |
| 5,676,923 A * | 10/1997 | Platzek et al. ............ 424/9.363 |
| 5,676,926 A * | 10/1997 | Platzek et al. ................ 424/9.3 |
| 5,683,694 A | 11/1997 | Bagshawe et al. |
| 5,693,762 A | 12/1997 | Queen et al. |
| 5,697,902 A | 12/1997 | Goldenberg |
| 5,716,595 A | 2/1998 | Goldenberg |
| 5,736,120 A * | 4/1998 | Srinivasan ................. 424/1.69 |
| 5,746,996 A | 5/1998 | Govindan et al. |
| 5,753,206 A | 5/1998 | McBride et al. |
| 5,772,981 A | 6/1998 | Govindan et al. |
| 5,776,093 A | 7/1998 | Goldenberg |
| 5,776,094 A | 7/1998 | Goldenberg |
| 5,776,095 A | 7/1998 | Goldenberg |

(Continued)

FOREIGN PATENT DOCUMENTS

EP    0263046    4/1988

(Continued)

OTHER PUBLICATIONS

Boisferon, Hillairet de et al., "Enhanced Targeting Specificity to Tumor Cells by Simultaneous Recognition of Two Antigens" Bioconjugate Chem. 2000 11, 252-460.

(Continued)

*Primary Examiner*—Yvonne Eyler
*Assistant Examiner*—MLouisa Lao
(74) *Attorney, Agent, or Firm*—Richard A. Nakashima

(57) ABSTRACT

Disclosed are compounds that include two or more haptens conjugated by a spacer or a carrier. The haptens may include diethylenetriaminepentaacetate (DTPA), histimine-succinyl-glutamine (HSG), or combinations of DTPA and HSG. The compound also includes an effector molecule which may be conjugated to one or more of the haptens, the spacer/carrier, or both. The effector molecule may be conjugated by a number of linkages including an ester linkage, an imino linkage, an amino linkage, a sulfide linkage, a thiosemicarbazone linkage, a semicarbazone linkage, an oxime linkage, an ether linkage, or combinations of these linkages. Also disclosed are methods of synthesizing the compounds and/or precursors of the compounds.

15 Claims, 18 Drawing Sheets

U.S. PATENT DOCUMENTS

| | | | | |
|---|---|---|---|---|
| 5,780,670 | A | * | 7/1998 | Yamamoto et al. .......... 560/169 |
| 5,820,849 | A | * | 10/1998 | Schmitt-Willich et al. . 424/9.36 |
| 5,837,242 | A | | 11/1998 | Holliger et al. |
| 5,837,243 | A | | 11/1998 | Deo et al. |
| 5,851,527 | A | | 12/1998 | Hansen |
| 5,874,061 | A | * | 2/1999 | Schmitt-Willich et al. ....................... 424/9.363 |
| 5,959,083 | A | | 9/1999 | Bosslet et al. |
| 6,004,529 | A | * | 12/1999 | Yu et al. .................... 424/1.65 |
| 6,010,680 | A | | 1/2000 | Govindan et al. |
| 6,039,773 | A | * | 3/2000 | Cherpeck ..................... 44/399 |
| 6,063,361 | A | * | 5/2000 | Schmitt-Willich et al. . 424/9.36 |
| 6,077,499 | A | | 6/2000 | Griffiths |
| 6,080,785 | A | * | 6/2000 | Platzek et al. ............... 514/547 |
| 6,096,289 | A | | 8/2000 | Goldenberg |
| 6,121,424 | A | | 9/2000 | Whitlow et al. |
| 6,126,916 | A | | 10/2000 | McBride |
| 6,187,284 | B1 | | 2/2001 | Griffiths |
| 6,248,306 | B1 | * | 6/2001 | Schmitt-Willich et al. . 424/1.65 |
| 6,280,706 | B1 | * | 8/2001 | Yu et al. ...................... 424/9.6 |
| 6,962,702 | B2 | * | 11/2005 | Hansen et al. ........... 424/136.1 |
| 7,074,405 | B1 | | 7/2006 | Hansen |
| 7,199,268 | B2 | * | 4/2007 | Platzek et al. ............... 564/153 |
| 2002/0006379 | A1 | | 1/2002 | Hansen et al. |

FOREIGN PATENT DOCUMENTS

| | | |
|---|---|---|
| EP | 0511011 A | 10/1992 |
| EP | 0517024 A2 | 12/1992 |
| EP | 0623675 | 9/1994 |
| EP | 0419387 | 11/1996 |
| IE | 921782 | 12/1992 |
| JP | 03173900 A | 7/1991 |
| WO | WO 9604313 | 2/1996 |
| WO | WO 9725305 A1 * | 7/1997 |
| WO | WO 97/41898 | 11/1997 |
| WO | WO 9808875 | 3/1998 |
| WO | WO 99/66951 A2 | 12/1999 |
| WO | WO 00/34317 | 6/2000 |

OTHER PUBLICATIONS

Pluckthun et al., "New protein engineering approaches to Multivalent and bispecific antibody fragments," Immunotechnology 3 (1997) 83-105.

Pack et al., "Tetravalent Miniantibodies with High Avidity Assembling in *Escherichia coli*," J. Mol. Biol. (1995) 246, 28-34.

Sharkey et al., "A Universal Pretargeting System for Cancer Detection and Therapy Using Bispecific Antibody," Cancer Research 63, 354-363 (Jan. 15, 2003).

Karacay et al., "Studies on a Humanized anti-CEA x murine anti-(In-DTPA) bispecific antibody construct for radioimmunotherapy of CEA-positive tumors," Proceedings of the American Association for Cancer Research Annual Meeting, vol. 40, p. 644 (Mar. 1999).

Karacay et al., "Pretargeting studies with a humanized anti-CEA X Murine anti-(In- DTPA) bispecific antibody construct and Tc-99m/Re-188 labeled peptide," Journal of Nuclear Medicine, Vo. 40, No. 5 Suppl., p. 225 (May 1999).

Gautherot et al., "Delivery of Therapeutic doses of Radioiodine using Bispecific antibody-targeted bivalent Hapatens," Journal of Nuclear Medicine, vol. 39 (11), pp. 1937-1943 (Nov. 1998).

Bodere et al. "Phase I/II trial of two-step radioimmunotherapy in medullary thyroid cancer (MTC) using bispecific anti-CEA/anti-DTPA-in antibody and iodine-131-labeled bivalent hapten," Journal of Nuclear Medicine, vol. 39, No. 5 Suppl., p. 246 (May 1998).

Bardies et al. "Bispecific antibody and iodine-131-labeled bivalent hapten dosimetry in patients with medullary thyroid or small-cell lung cancer," Journal of Nuclear Medicine, vol. 37, pp. 1853-1859 (Nov. 1996).

Kraeber-Bodere et al., "Bispecific antibody and bivalent hapten radioimmunotherapy in CEA-producing medullary tthyroid cancer xenograft," Journal of Nuclear Medicine, vol. 40 (1), pp. 198-224 (Jan. 1999).

Hosono et al., "Biodistriution and dosimetric study in medullary thyroid cancer xenograft using bispecific antibody and iodine-125-labeled bivalent hapten." Journal of Nuclear Medicine, vol. 39 (9), pp. 1608-1613 (Sep. 1998).

Kranenborg et al., "Development and characterization of anti-renal cell carcinoma x antichelate bispecific monoclonal antibodies for two-phase targeting of renal cell carcinoma," Cancer Research, Vo. 55 (23 Wuppl.), pp. 5864S-5867S (Dec. 1, 1995).

Kranenborg et al., "Two-Step radio-immunotargeting of renal-cell carcinoma xenografts in nude mide with anti-renal-cell-carcinoma X anti-DTPA bispecific monoclonal antibodies," International Journal of Cancer, vol. 75 (1), pp. 74-80 (Jan. 5, 1998).

Gautherot et al., "Therapy for colon carcinoma xenografts with bispecific antibody-targeted, iodine-131-labeled bivalent hapten," Cancer, vol. 80, No. Supp. 12, pp. 2618-2623 (Dec. 15, 1997).

Bosslet et al., "Generation of bispecific monoclonal antibodies for two phase radioimmunotherapy," British Journal of Cancer, Vo. 63/5, pp. 681-686 (1991).

Manetti et al. "Intracellular uptake and catabolism of anti-IgM antibodies and bi-specific antibody-targeted hapten by B-lymphoma cells," Int. J. Cancer, vol. 63(2), pp. 250-256 (1995).

Barbet et al., "Radioimmunotherapy of LS174T colon arcinoma in nude mice using an iodine-131-labeled bivalent hapten combined with an anti-CEAX anti-indium-DTPA bispecific antibody," Tumor Biology, vol. 18, No. Suppl. 2, p. 31 (Sep. 1997).

McGuinness et al, "Phage diabody repertoires for selection of large number of bispecific antibody fragments," Nature Biotechnology, 14:1149-1154 (1996).

Alt, et al., "Novel tetravalent and bispecific IgG-like antibody molecules combining single chain diabodies with the immunoglobulin gamma-1 or CH3 region," FEBS LETT, 454: 90-94 (1999).

Olafsen et al., "IgM secretory tailpiece drives multimerisation of bivalent scFv fragments in eukaryotic Cells," Immunotechnology, 4(2):141-153 (1998).

Kipriyanov et al., "Bispecific tandem diabody for tumor therapy with improved antigen binding and pharmacokinetics," J. Mol. Biol., 293(1):41-56 (1999).

Hawkins, et al., "Delivery of Radionuclides to Pretargeted Monoclonal, Antibodies Using Dihydrofolate Reductase and Methotrexagte in an Affinity System," Cancer Research, vol. 53, pp. 2368-2373, May 1993.

Goodwin, et al., "Pre-Targeted Immunoscintigraphy of Murine Tumors with Indium-111-Labeled Bifunctional Haptens," J. Nucl, Med., vol. 29, pp. 226-234, 1998.

Stickney, et al., "Bifunctional Antibody: A binary Radiopharmaceutical Delivery System for Imaging Colorectal Carcinoma," Cancer Research, vol. 51, pp. 6650-6655, Dec. 15, 1991.

Gautherot, et al., "Therapy for Colon Carcinoma Xenografts with Bispecific Antobody-Targeted, Iodine-131-Labeled Bivalent Hapten," Cancer Supplelment, vol. 80, pp. 2618-2623, 1997.

Barbet et al., "Radioimmunodetection of Medullary Thyroid Carcinoma Using Indium-111 Bivalent Hapten and Anti-CEA X Anti-DTPA-Indium," The Journal of Nuclear Medicine, vol. 39, No. 7, Jul. 1998.

Kranenborg, et al. "Development and Characterization of Anti-Renal Cell Carcinoma x Antichelate Bispecific Monoclonal Antibodies for Two-Phase Targeting of Renal Cell Carcinoma," Cancer Research Supplment, vol. 55, pp. 5864s-5867s, Dec. 1, 1995.

Chatziioannou, A., et al., MICROPET 1: performance Evaluation of a Very High Resolution pet Scanner Proceedings of the 44th Annual Meeting Scientific Papers, vol. 38, No. 5, May 1997 Supplement.

Schuhmacher, et al., "Multistep Tumor Targeting in Nude Mice Using Bispecific Antibodies and a Gallium Chelate Suitable for Immunoscintigraphy with Positron Emission Tomography," Cancer Research, vol. 55, pp. 115-123, Jan. 1, 1995.

Sharkey, et al., "Development of a Streptavidin—Anti-Carcinoembryonic Antigen Antibody, Radiolabeled Biotin Pretargeting Method for Radioimmunotherapy of Colorectal Cancer. Studies in A Colon Cancer Xenograft Model," Bioconjugate Chemical, vol. 8, No. 4, 1997.

Arano, Yasushi, et al., "Reassessment of Diethylenetriaminepentaacetic Acid (DTPA) as a Chelating Agent for Indium-111 Labeling of Polypeptides Using a Newly Synthesized Monoreactive DTPA Derivative," J. Med. Chem, vol. 39, pp. 3451-3460, 1996.

Barmas, A., et al. "Two-Step Strategies for the Diagnosis and Treatment of Cancer with Bioconjugates," Antibody, Immunoconjugates, Radiopharm., vol. 5, No. 4, pp. 385-395, 1992.

Bos, Ebo S., et al. "In Vitro Evaluation of DNA-DNA Hybridization as a Two-Step Approach in Radioimmunotherapy of Cancer," Cancer Research, vol. 54, pp. 3479-3486, 1994.

Gautherot, et al., "Radioimmunotherapy of LS174T Colon carcinoma in Nude Mice Using an Iodine-131-Labeled Bivalent Hapten Combined with an Anti-CEA X Anti-Iindium-DTPA Bispecific Antibody," J. Nucl. Med., vol. 38, p. 7, 1997.

Greenwood, F. C., et al., "The Preparation of 131I-Labelled Human Growth Hormone of High Specific Radioactivity," The Biochemical Journal, vol. 89, pp. 114-123; 1963.

Kaneko, T., "New Hydrazone Derivative of Adriamycin and Their Immunoconjugates—a Correlation between Acid Stability and Cytotoxicity," J. Bioconjugate Chem., vol. 2, No. 3, pp. 133-141, 1991.

Karacay, et al., "Experimental Pretargeting Studies of Cancer with a Humanized anti-CEA x Murine anti-[In-DTPA] Bispecific Antidoy Construct and a 99mTc-/188 Re-Labeled Peptide," Bioconjugate Chem., vol. 11, pp. 842-854, 2000.

Losman, M. J., et al., "Generation and Monitoring of Cell Lines Producing Humanized Antibodies," Clin. Cancer Research, vol. 5, (10 Suppl.) pp. 3101s-3105s, 1999.

Penefsky, Harvey S., "A Centrifuged-Column Procedure for the Measurement of Ligand Binding by Beef Heart F," Methods in Enzymology, Part G, vol. 56, pp. 527-530, 1979.

Wang, Shing-Ming, et al., "Specific Activation of Glucuronide Prodrugs by Antibody-targeted Enzyme Conjugates for Cancer Therapy," Cancer Res., vol. 52, pp. 4484-4491, 1992.

De Jonge, Jan, et al., "Production and Characterization of Bispecific Single-Chain Antibody Fragments," Molecular Immunology, vol. 32, No. 17/18, pp. 1405-1412, 1995.

Boden, V., et al., "Preliminary Study of the Metal Binding Site of an Anti-DTPA-Indium Antibody by Equilibrium Binding Immunoassays and Immobilized Metal Ion Affinity Chromatography," Bioconjugate Chem., vol. 6, pp. 373-379, 1995.

Gold et al., Cancer Research, 50 6405-6409, 1990.

Van Spriel, et al., "Immunotherapeutic Perspective for Bispecific antibodies" Immunology Today, 21, 391-396, 2000.

Kontermann, Roland E., "Intracellular and Cell Surface Displayed single-chain Diabodies" Journal of Immunological Methods 226 (1999) 179-188.

Dubel, S., "Reconstitution of human pancreatic RNase from two separate fragments fused to different single chain antibody fragments: on the way to binary immunotoxins" Tumor Targeting (1999) 4, 37-46 XP009010728.

Hayden, M. "Single-chain mono- and bispecific antibody derivatives with novel biological properties and antitumour activity from a COS cell transient expression system" Therapeutic Immunology, 1994, 1, 3-15.

Yang "A Genetically Engineered Single-Chain FV/TNF Molecule Possesses the Anti-Tumor Immunoreactivity of FV as well as the Cytotoxic Activity of Tumor Necrosis Factor" Molecular Immunology vol. 32, No. 12, pp. 873-881, 1995 XP 000653177.

Karacay, H., et al., "Pretargeting Studies with a Murine Anti-Colon-Specific Antigen-P (CSAp) X Chimeric Anti-[Indium-DTPA] Bispecific Antibody and Technetium-99m-Labeled Peptide" Cancer Biotherapy and Radiopharmaceuticals, vol. 15, No. 4, 2000, p. 412, XP008065412.

Karacay, H., et al., "Experimental Pretargeting Studies of Cancer with a Humanized anti-CEA Murine anti-[In-DTPA] Bispecific Antibody Construct and a 99mTc-/188Re-Labeled Peptide" Bioconjugate Chem. 2000, 11, 842-854.

* cited by examiner

Fig. 1  Bis In³⁺ IMP 274
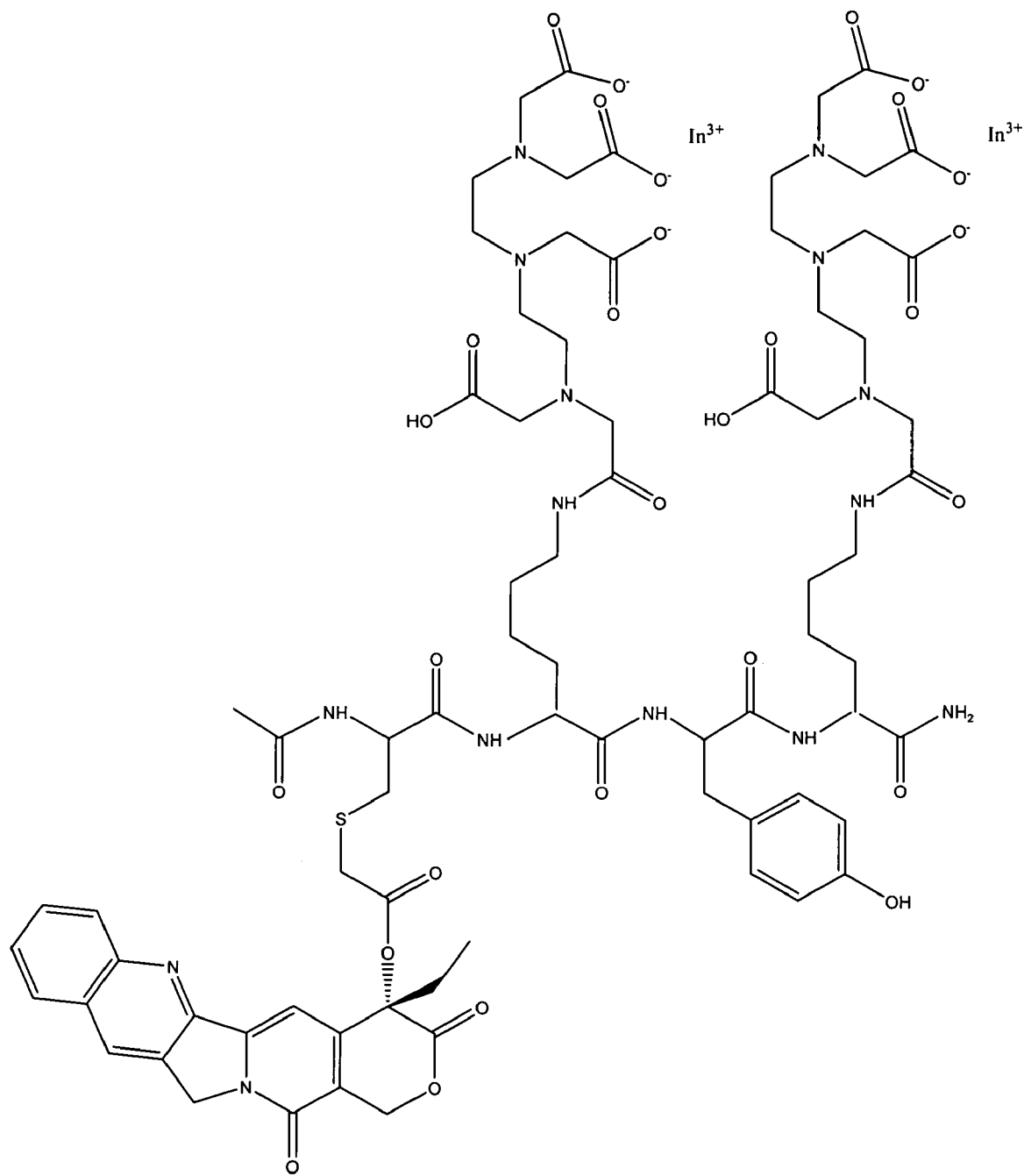

Fig. 2 Bis In³⁺ IMP 274 (SN-38 analog)
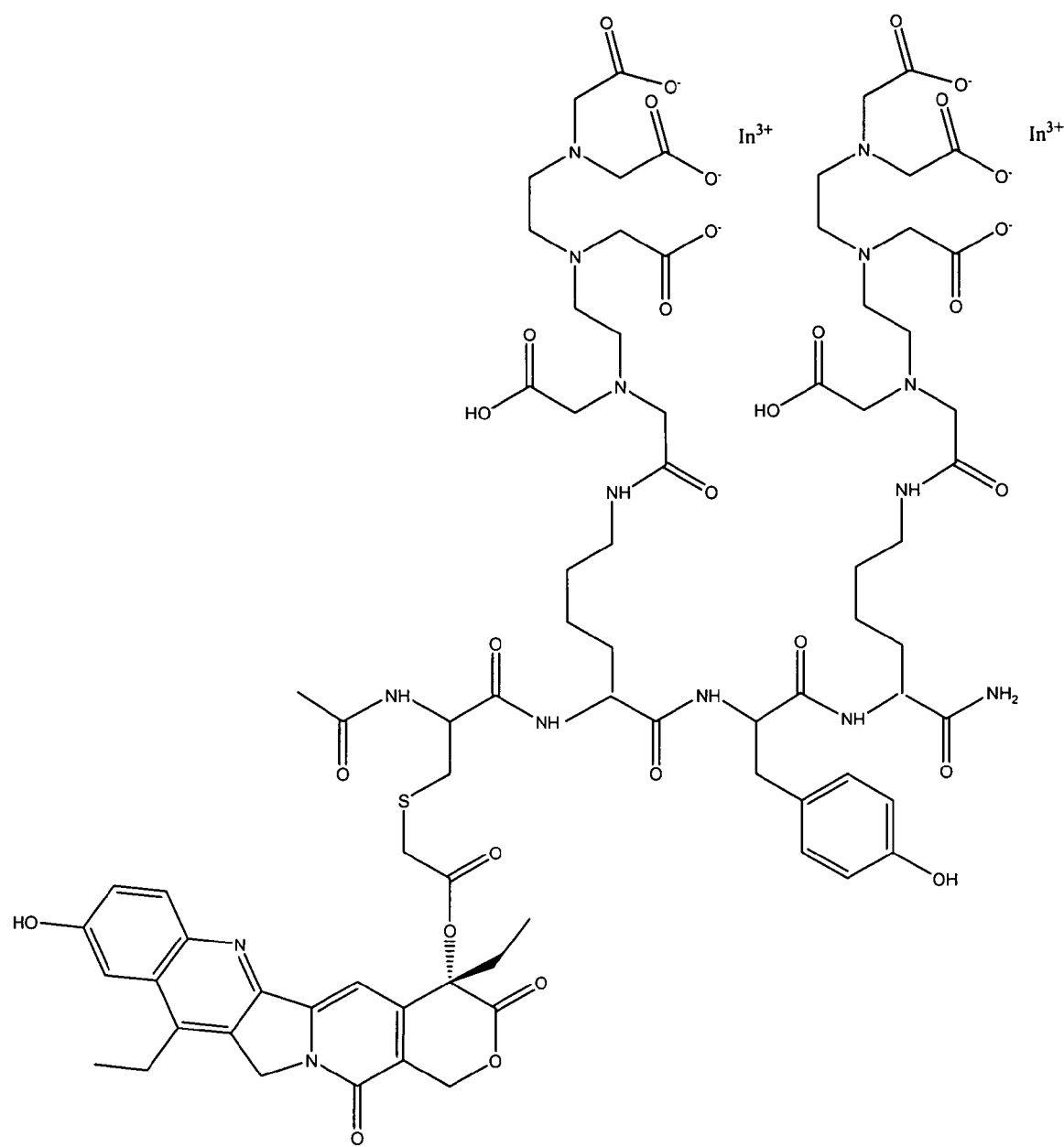

Fig. 3  Bis In³⁺ IMP 274 (SN-38 analog with penicillamine linker)
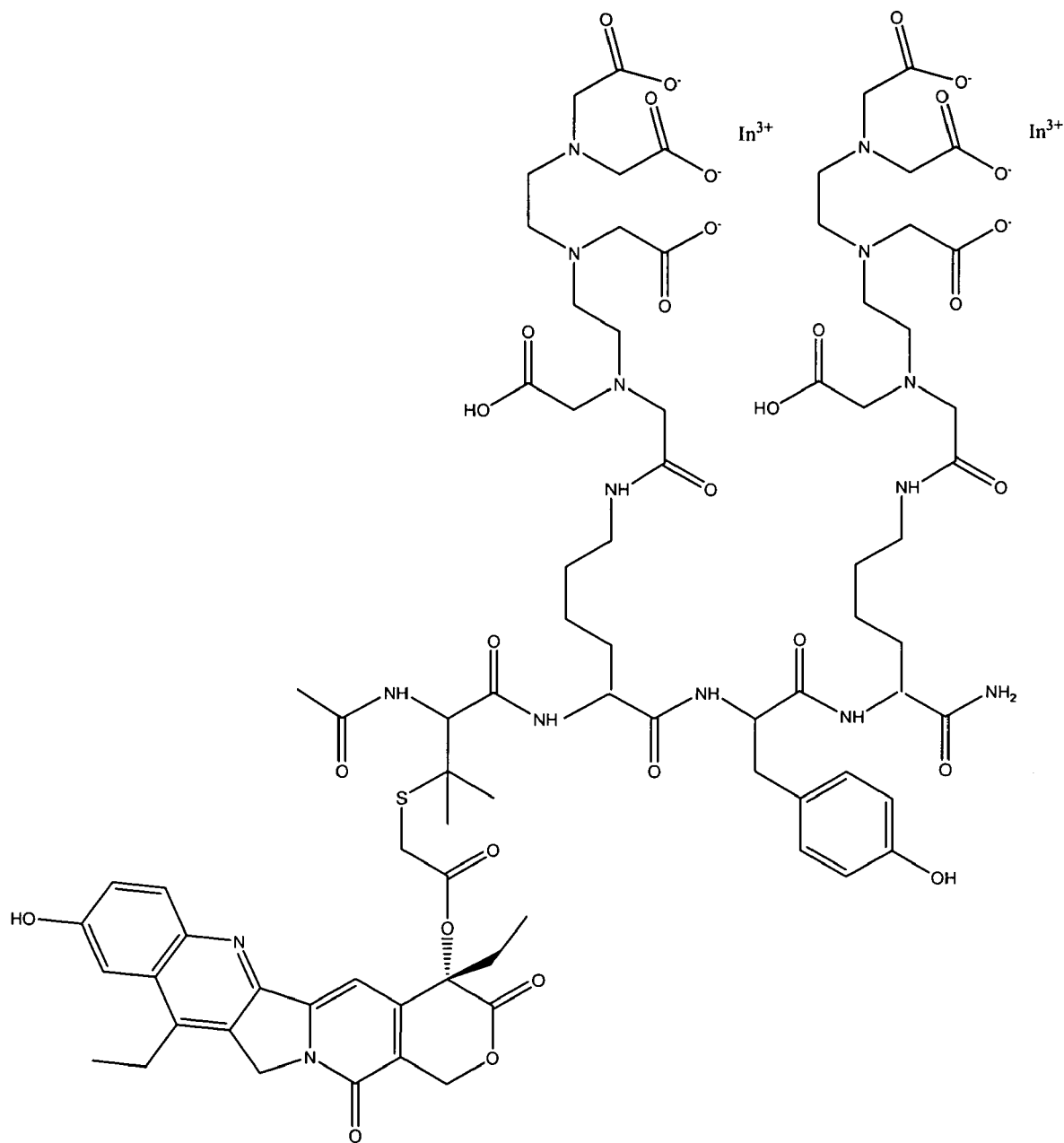

Fig. 4  Bis In³⁺ IMP 274 (SN-38 analog linked to a cysteine using a hindered ester)
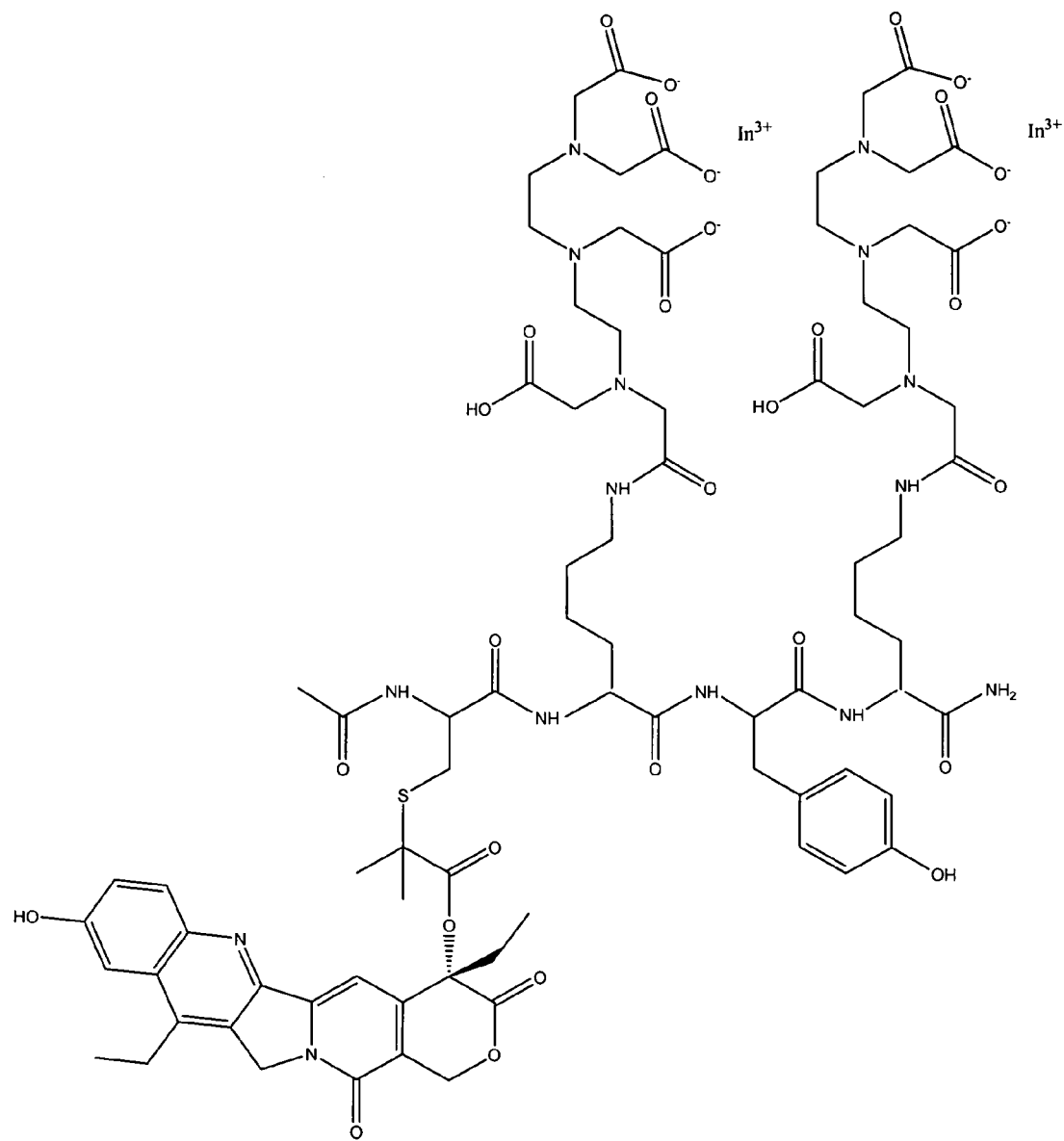

Fig. 5 IMP 225
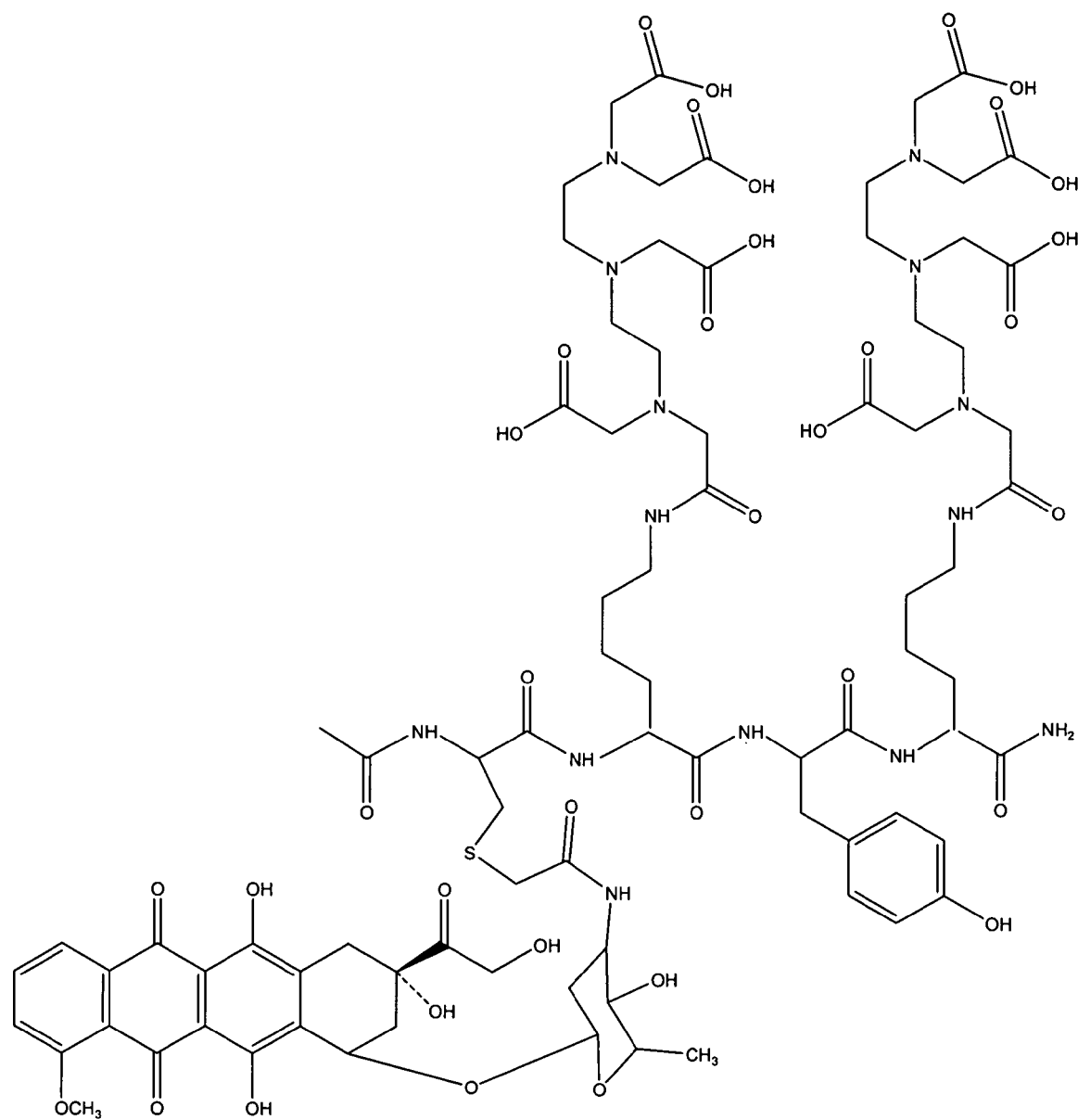

Fig. 6  Bis In³⁺ IMP 224
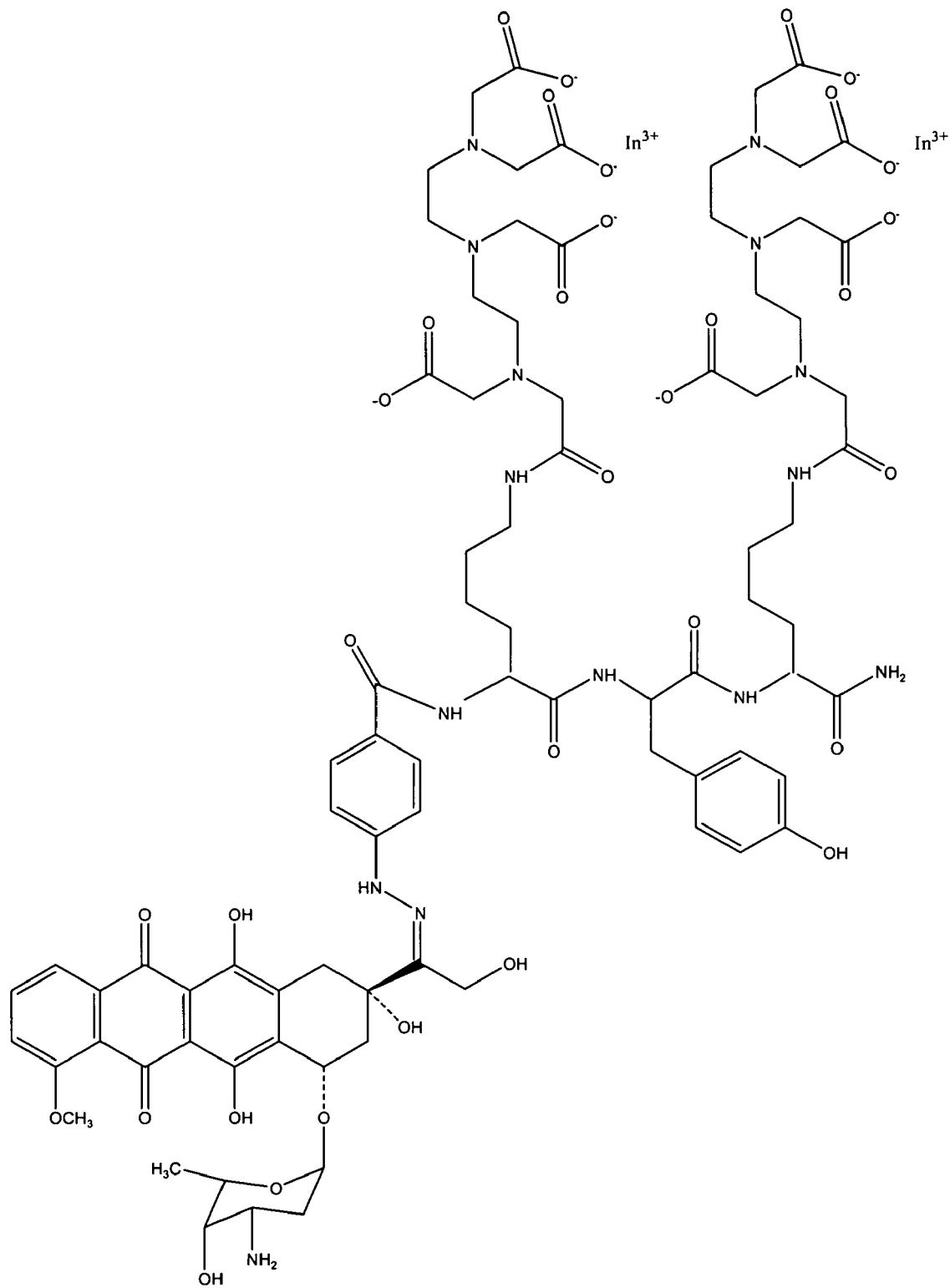

Fig. 7 HPLC analysis (Reverse Phase) of $^{111}$In-Labeled IMP 274
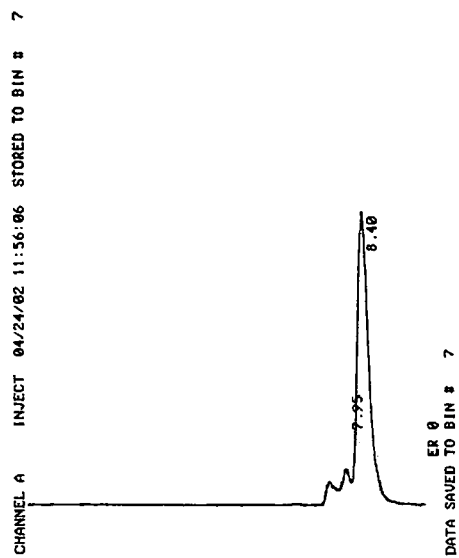

Fig. 8 HPLC Analysis (Size Exclusion) of $^{111}$In-Labeled IMP 274
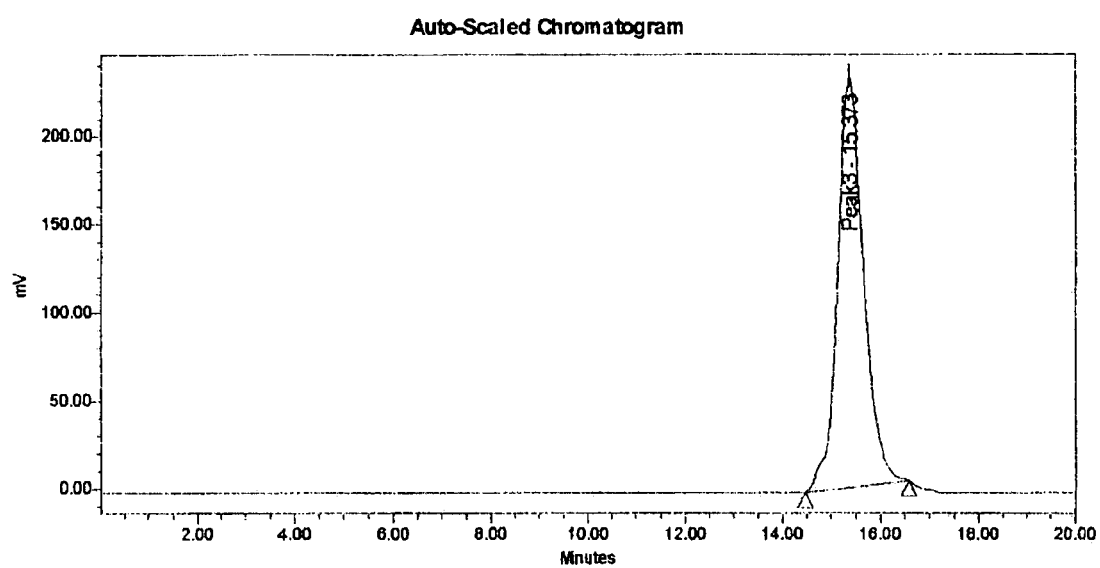

Fig. 9A  HPLC analysis (Reverse Phase) of
$^{111}$In-Labeled IMP 274 in Mouse Serum
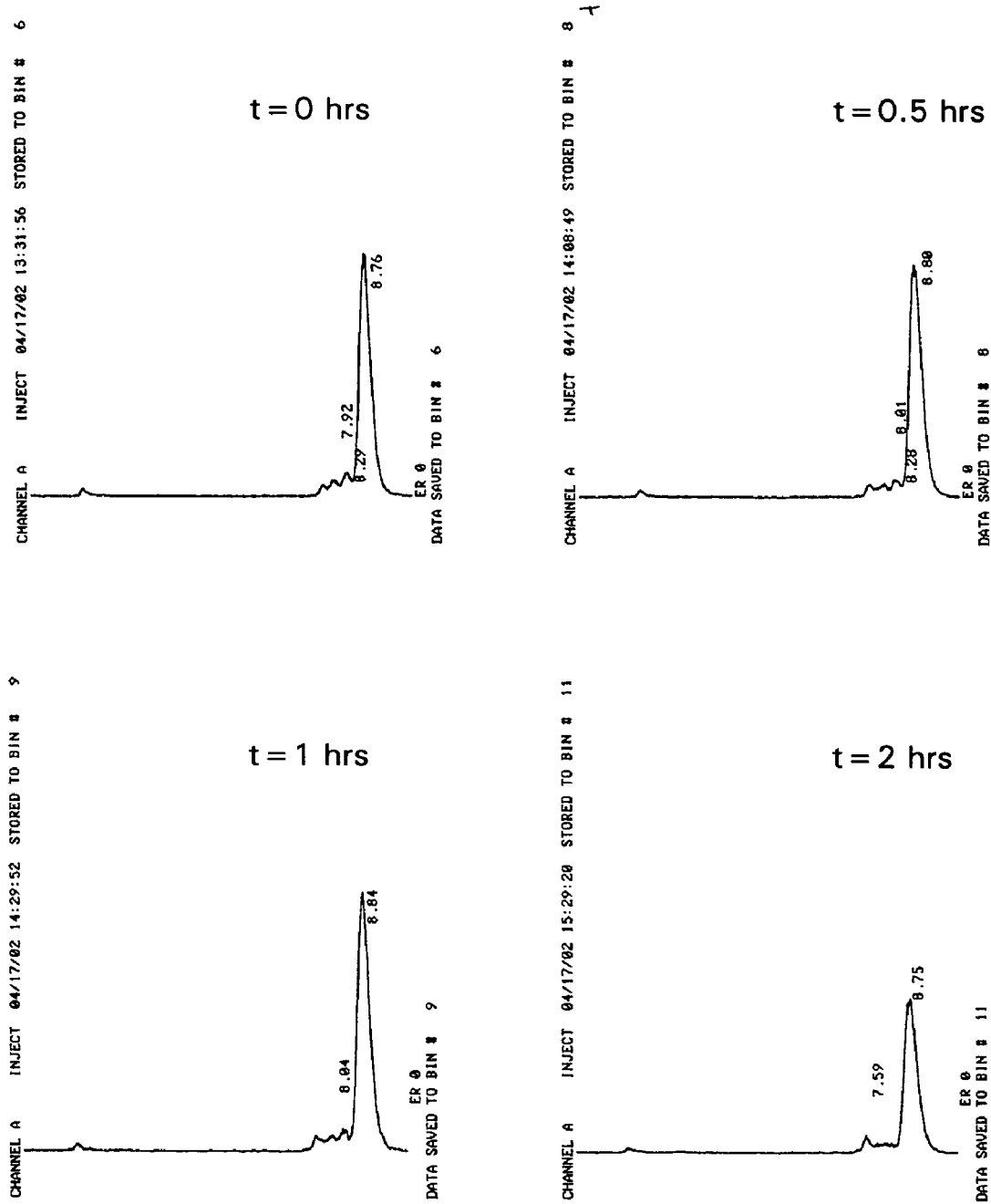

Fig. 9B  HPLC analysis (Reverse Phase) of $^{111}$In-Labeled IMP 274 in Mouse Serum
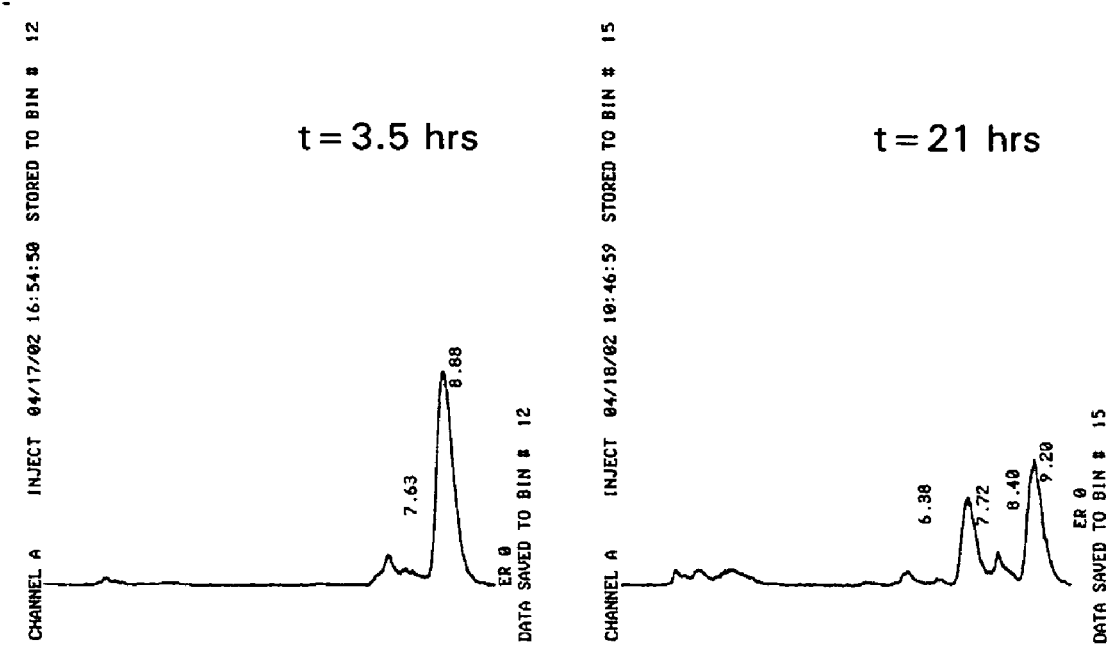

Fig. 10A  HPLC analysis (Reverse Phase) of
$^{111}$In-Labeled IMP 274 in Human Serum
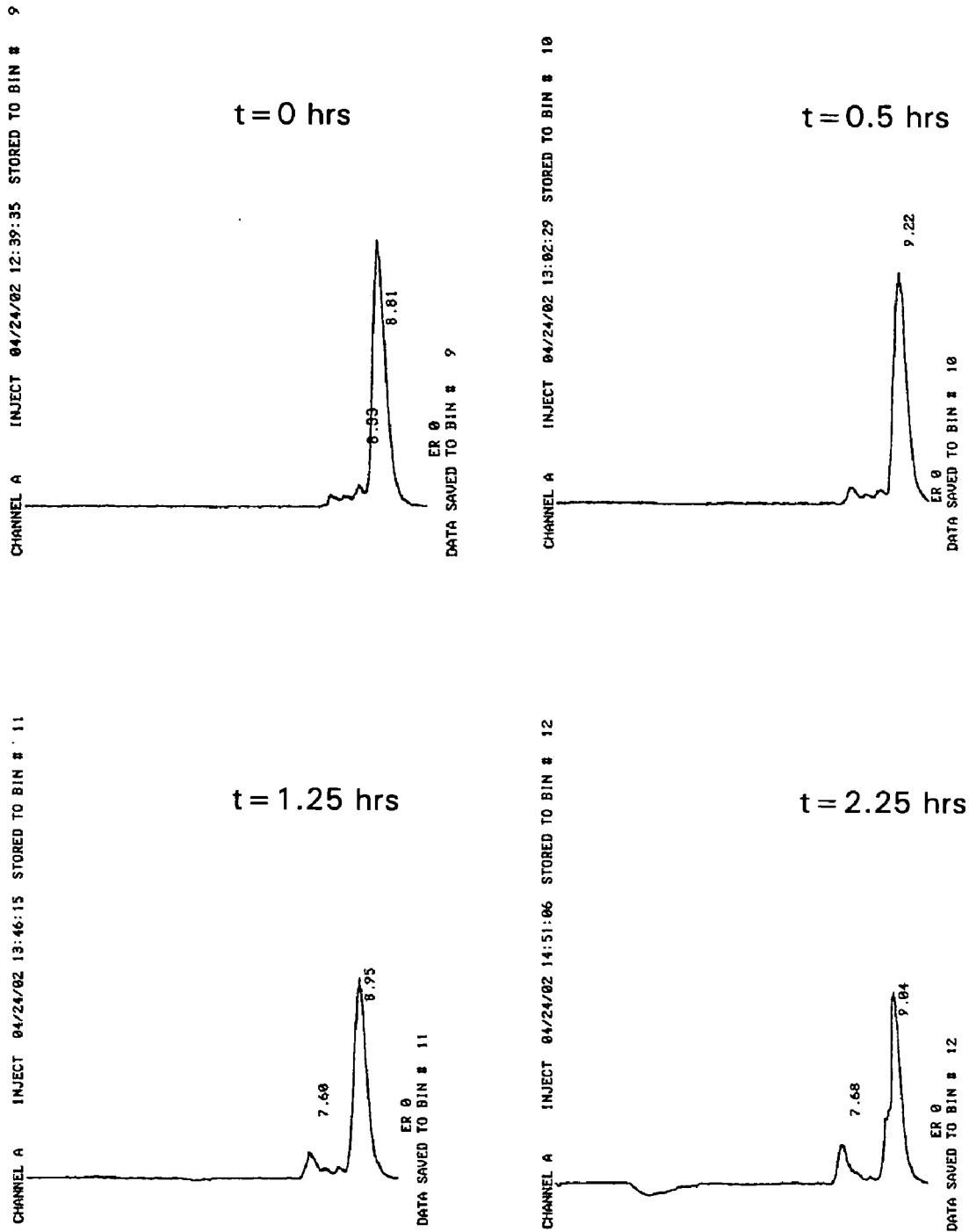

Fig. 10B  HPLC analysis (Reverse Phase) of
$^{111}$In-Labeled IMP 274 in Human Serum
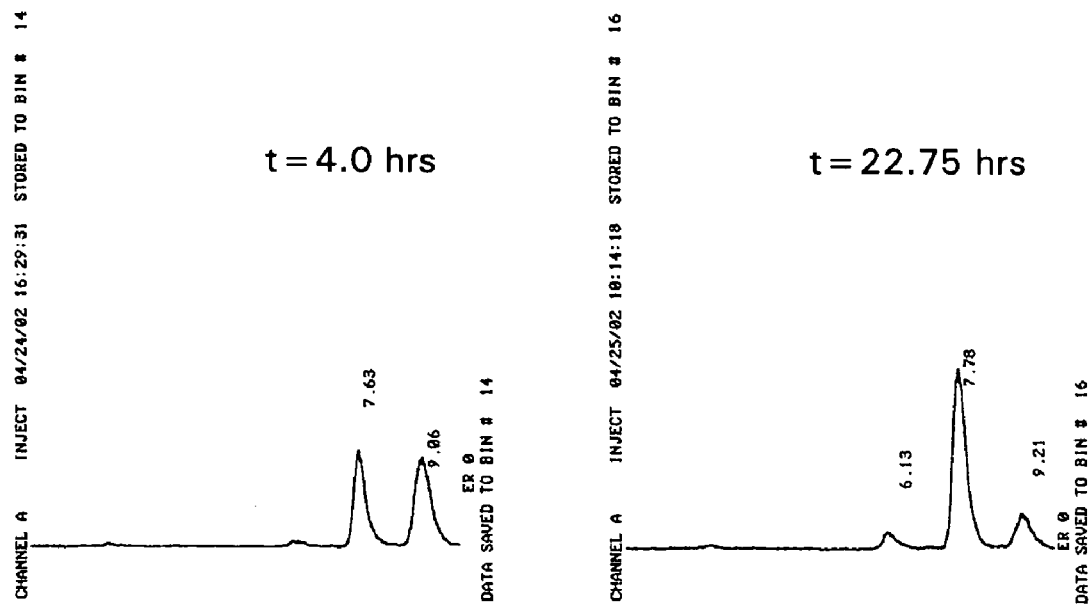

Fig. 11  HPLC analysis (Size Exclusion) of $^{111}$In-Labeled IMP 274 in Mouse Serum containing bsAb 734xhMN14
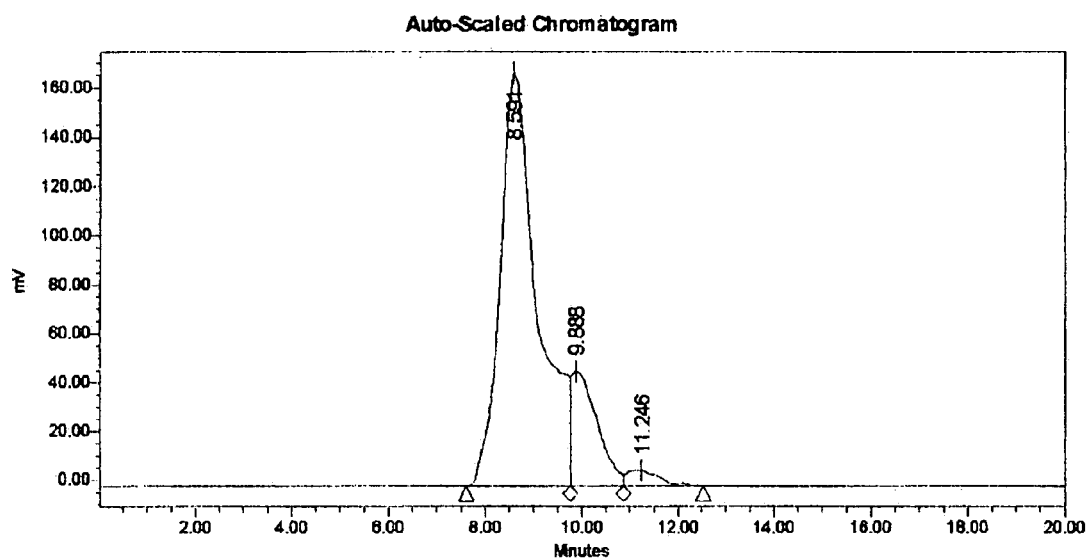

Fig. 12  HPLC analysis (Size Exclusion) of $^{111}$In-Labeled IMP 274 in Human Serum containing bsAb 734xhMN14
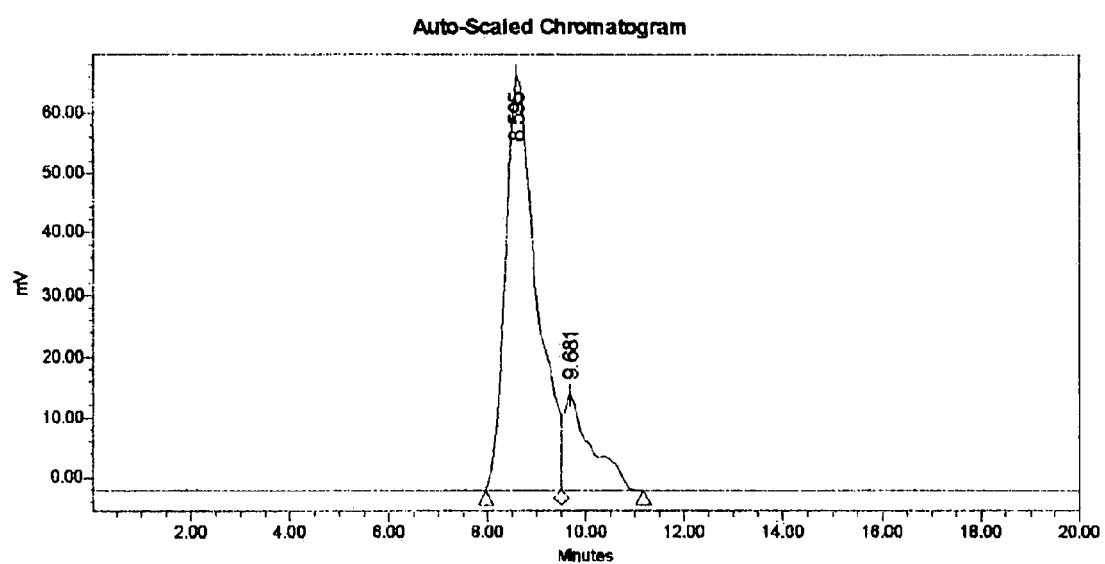

Fig. 13    Stability of IMP 294 (A) and IMP 295 (B) in PBS at 25°C Over 7 Days
A
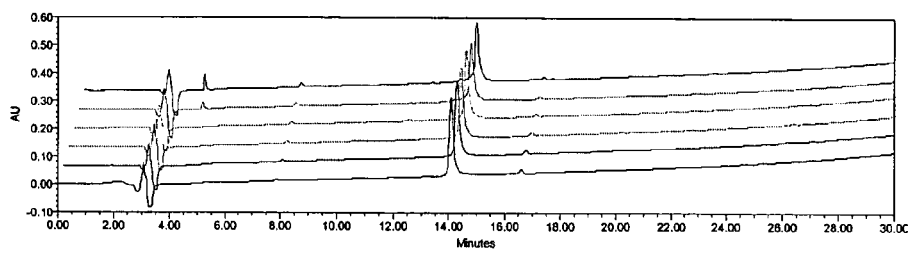
B
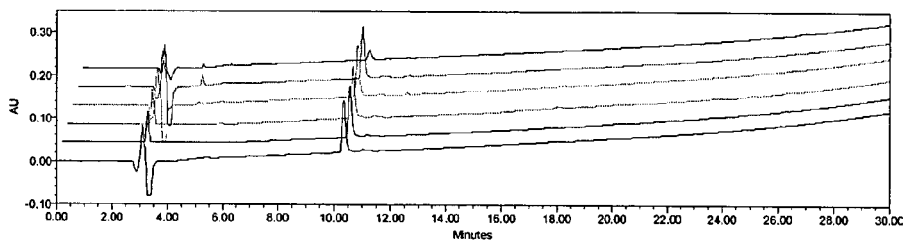

Fig. 14 Pre-targeting in SCID Mice
A.
| SCID Mice Inoculated i.v. with 1.5 x 10⁷ Daudi Cells | | | | | |
|---|---|---|---|---|---|
| Group | (N) | Treatment | Ratio | Dose | Schedule |
| I | 9 | LL2x734<br>IMP-225 | (1:1) | 300 µg (3 x 10⁻⁹ moles)<br>~6 µg (3 x 10⁻⁹ moles) | Days 1, 3, 7, 9<br>Days 2, 4, 8, 10 |
| II | 8 | IMP-225<br>Alone | N/A | ~30 µg (1.5 x 10⁻⁸ moles) | Days 2, 4, 8, 10 |
B.
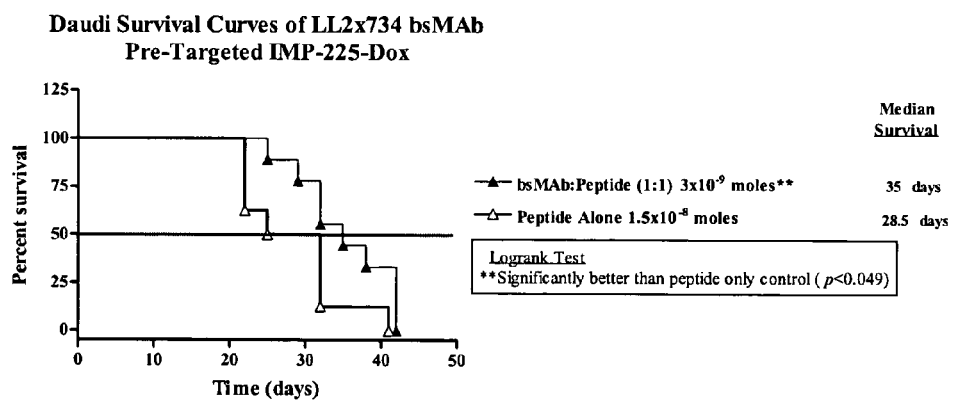

Fig. 15 Synthesis of DTPA Precursor and DTPA (Three Step Method)
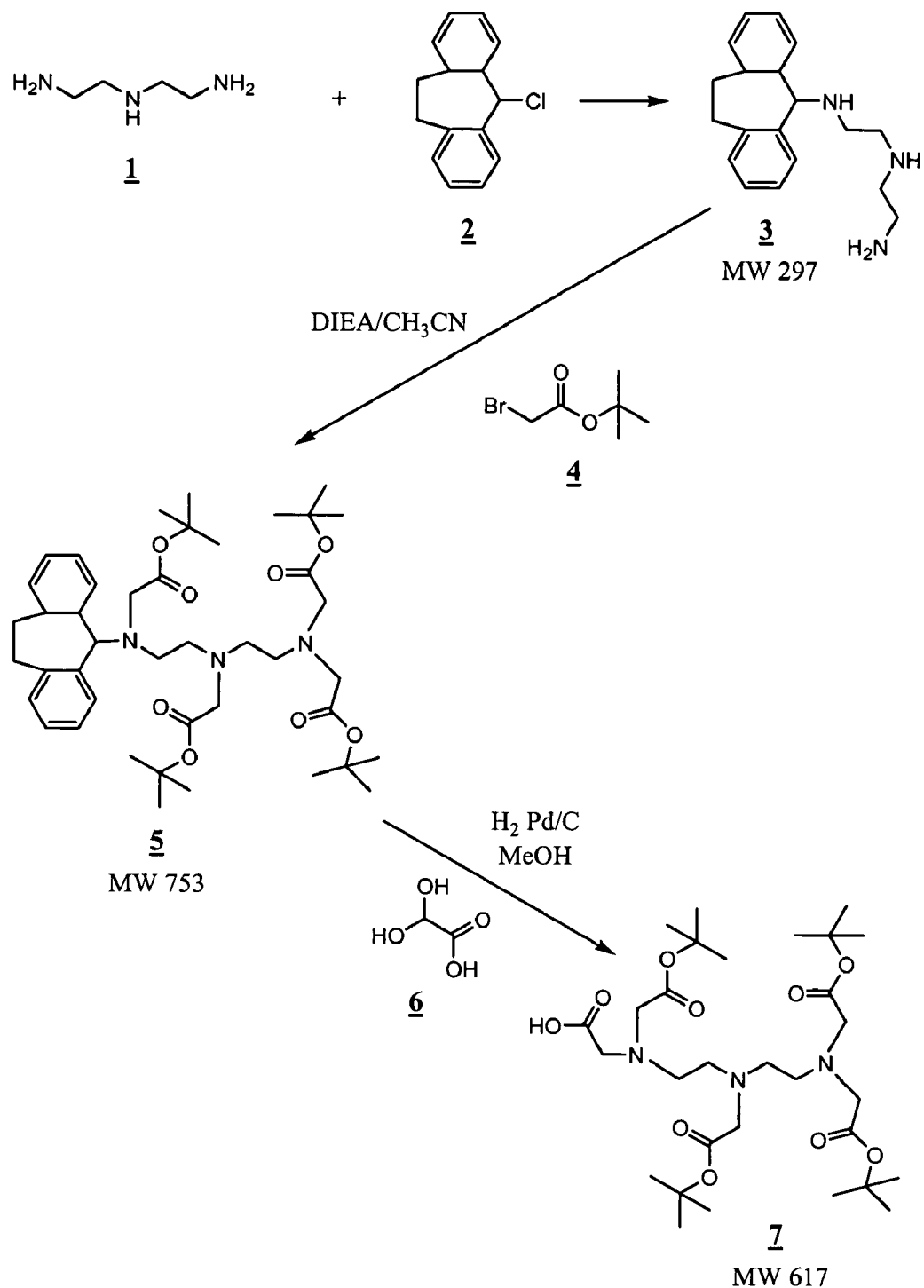

Fig. 16   Synthesis of DTPA Precursor and DTPA (Four Step Method)
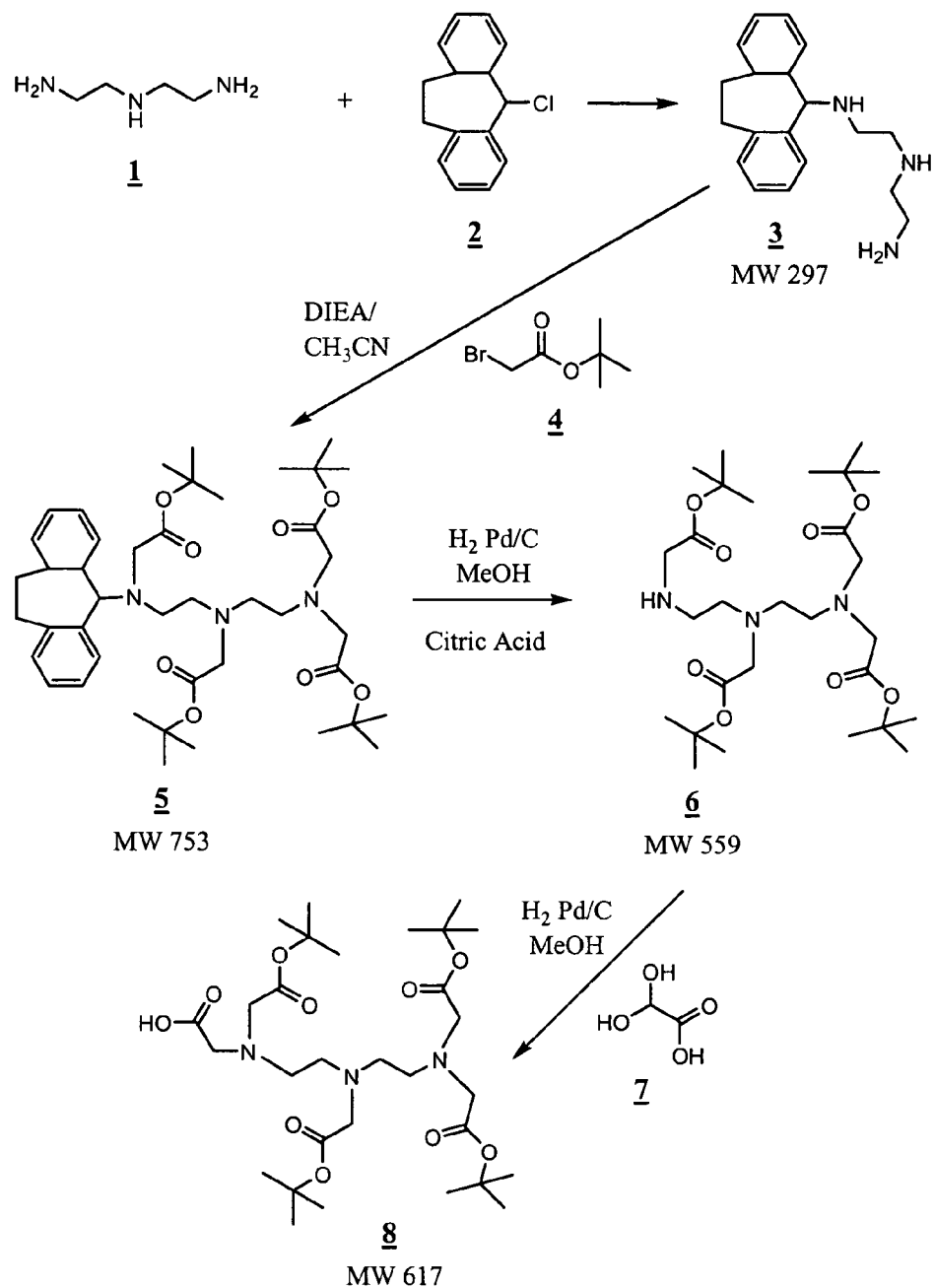

THERAPEUTIC AND DIAGNOSTIC CONJUGATES FOR USE WITH MULTISPECIFIC ANTIBODIES

CROSS-REFERENCE TO RELATED APPLICATIONS

This application is a continuation-in-part of U.S. application Ser. No. 10/150,654, filed May 17, 2002; which is a continuation-in-part of U.S. application Ser. No. 09/382,186, filed Aug. 23, 1999 and a continuation-in-part of U.S. application Ser. No. 09/823,746, filed Apr. 3, 2001; both of which are continuations-in-part of U.S. application Ser. No. 09/337,756, filed Jun. 22, 1999; which claims the benefit under 35 U.S.C. § 119(e) to U.S. application Ser. No. 60/090,142, filed Jun. 22, 1998, and to U.S. application Ser. No. 60/104,156, filed Oct. 14, 1998. The contents of all the aforementioned applications are incorporated herein by reference in their entireties.

BACKGROUND

A general approach to cancer therapy and diagnosis involves directing antibodies or antibody fragments to disease tissues, whereby the antibody or antibody fragment can target a diagnostic agent or therapeutic agent to the disease site. One specific approach to this methodology which has been under investigation, involves the use of bsAbs having at least one arm that specifically binds a targeted diseased tissue and at least one other arm that specifically binds a low molecular weight hapten. In this methodology, a bsAb is administered and allowed to localize to a target and to clear normal tissue. Some time later, a radiolabeled low molecular weight hapten is given, which, being recognized by the second specificity of the bsAb, also localizes to the original target.

Although low MW haptens used in combination with bsAbs possess a large number of specific imaging and therapy uses, it is impractical to prepare individual bsAbs for each possible application. Further, the application of a bsAb/low MW hapten system has several other requirements. First, the arm of the bsAb that binds to the low MW hapten must bind with high affinity, because a low MW hapten is designed to clear the living system rapidly when not bound by bsAb. Second, the non-bsAb-bound low MW hapten actually needs to clear the living system rapidly to avoid non-target tissue uptake and retention. Third, the detection and/or therapy agent must remain associated with the low MW hapten throughout its application within the bsAb protocol.

Of interest with this approach are bsAbs that direct chelators and metal chelate complexes to cancers using Abs of appropriate dual specificity. The chelators and metal chelate complexes used are often radioactive, using radionuclides for radioimmuno-imaging. (See Goodwin et al., U.S. Pat. No. 4,863,713 (describing the use of cobalt-57); Barbet et al., U.S. Pat. No. 5,256,395 and U.S. Pat. No. 5,274,076; Goodwin et al., *J. Nucl. Med.*, 33:1366-1372 (1992); and Kranenborg et al., *Cancer Res* (suppl.), 55:5864s-5867s (1995) and *Cancer* (suppl.) 80:2390-2397 (1997) (all describing the use of indium-111); and Boden et al., *Bioconjugate Chem.*, 6:373-379, (1995); and Schuhmacher et al., *Cancer Res.*, 55:115-123 (1995)(describing the use of gallium-68)). Because the Abs are raised against the chelators and metal chelate complexes, they have remarkable specificity for the complex against which they were originally raised. Indeed, the bsAbs of Boden et al. have specificity for single enantiomers of enantiomeric mixtures of chelators and metal-chelate complexes. This great specificity has proven to be a disadvantage in one respect, in that other nuclides (such as yttrium-90 and bismuth-213 useful for radioimmunotherapy (RAIT), and gadolinium useful for MRI), cannot be readily substituted into available reagents for alternative uses. As a result iodine-131, a non-metal, has been adopted for RAIT purposes by using an I-131-labeled indium-metal-chelate complex in the second targeting step. Another disadvantage to this methodology requires that antibodies be raised against every agent desired for diagnostic or therapeutic use.

As such, pretargeting methodologies have received considerable attention for cancer imaging and therapy. Unlike direct targeting systems where an effector molecule (e.g., a radionuclide or a drug linked to a small carrier) is directly linked to the targeting agent (e.g., a binding molecule such as a bsAb), in pretargeting systems, the effector molecule is given some time after the targeting agent. This allows time for the targeting agent to localize in tumor lesions and, more importantly, clear from the body. Because most targeting agents have been binding proteins such as antibodies, they tend to clear much more slowly from the body (usually days) than the smaller effector molecules (usually in minutes). As such, in direct targeting systems involving therapeutic radionuclides, the body, and in particular the highly vulnerable red marrow, may be exposed to the radiation all the while the targeting agent is slowly reaching its peak levels in the tumor and clearing from the body. However, in a pretargeting system, the radionuclide (i.e., an effector) is usually bound to a small "carrier" molecule, such as a chelate or peptide, which clears very quickly from the body, and thus exposure of normal tissues is minimized. In a pretargeting system, maximum tumor uptake of the radionuclide is also very rapid because the small carrier molecule efficiently transverses the tumor vasculature and binds to the primary targeting agent. The small size of a carrier molecule may also encourage a more uniform distribution in the tumor.

Pretargeting methods have used a number of different strategies, but often involve an avidin/streptavidin-biotin recognition system or bi-specific antibodies that co-recognize a tumor antigen and one or mole haptens on the carrier molecule, which includes an effector molecule. The avidin/streptavidin system is highly versatile and has been used in several configurations. In this system, antibodies coupled with streptavidin or biotin are used as the primary targeting agent. This is followed sometime later by administration of the effector molecule, which may be conjugated with biotin or with avidin/streptavidin, respectively. Another configuration relies on a 3-step approach: (1) first targeting a biotin-conjugated antibody; (2) followed by a bridging with streptavidin/avidin; and (3) then the biotin-conjugated effector is given. These systems can be easily converted for use with a variety of effector substances so long as the effector and the targeting agent can be coupled with biotin or streptavidin/avidin depending on the configuration used. With its versatility for use in many targeting situations and high binding affinity between avidin/streptavidin and biotin, this type of pretargeting has considerable advantages over other proposed systems. However, avidin and streptavidin are foreign proteins and therefore can be immunogenic, which may limit the number of times they can be administered in a clinical application. In this respect, bsAbs have the advantage of being able to be engineered as a relatively non-immunogenic humanized protein. Although the binding affinity of a bsAb (typically $10^{-9}$ to $10^{-10}$ M) cannot compete with the extremely high affinity of the streptavidin/avidin-biotin affinity ($\sim 10^{-15}$ M), both pretargeting systems are dependent on the binding affinity of the primary targeting agent, and therefore the higher affinity of the streptavidin/avidin-biotin systems may not offer a substantial advantage over a bsAb pretargeting system. However, most bsAbs have only one arm available for binding the primary target, whereas the streptavidin/avidin-biotin pretargeting systems typically use a whole IgG with two arms for binding the target, which strengthens target binding. By using a divalent peptide, an affinity enhancement may be achieved, which can greatly improve the binding of the peptide to the target site compared to a monovalent peptide. Thus, both systems can provide excellent targeting ratios with reasonable retention.

Pretargeting with a bsAb also requires one arm of the antibody to recognize an effector molecule or a molecule that contains an effector molecule (e.g., a carrier with an effector together as a "targetable construct"). Most radionuclide targeting systems reported to date have relied on an antibody to a chelate-metal complex, such as antibodies directed against indium-loaded DTPA or antibodies to other chelates. Because the antibody is generally selective for a particular chelate-metal complex, new bsAbs typically need to be constructed for each selected chelate-metal complex. This can be avoided by using a carrier molecule that includes the effector molecule and a hapten, which is specifically recognized by the antibody. As such, the carrier, including the effector and hapten, functions as a targetable construct. The targetable construct is "modular" in nature, in that different effectors can be included in the construct without having to use a different antibody in the pretargeting system, because the antibody recognizes the hapten on the targetable construct. In this way, a variety of effectors can be used in the pretargeting system, provided that the targetable construct that includes the effector maintains the same recognized hapten.

Because in a pre-targeting method the effector molecule (i.e., targeting molecule or carrier molecule) and the binding molecule (i.e., the targeting construct or antibody) are not administered concurrently, the binding molecule must not be internalized by the targeted tissue prior to administering the effector molecule. However, because the binding molecule is bivalent and bispecific, internalization of the binding molecule may be hindered or delayed until after the effector molecule is administered, even if the binding molecule recognizes an antigen that is part of an internalizing receptor on the surface of the targeted tissue. Further, if the effector molecule is multivalent (i.e., it has two or more moieties recognized by the binding molecule), the effector molecule can crosslink two or more binding molecules on the surface of the targeted tissue to facilitate internalization of the crosslinked complex. The effector molecule may also include one or more moieties that facilitate internalization by binding to internalizing receptors on the surface of the targeted tissue (e.g., the folate receptor). Methods of compositions for administering therapeutic and diagnostic agents are described in U.S. Ser. No. 60/444,357, filed Jan. 31, 2003.

Thus, there is a continuing need for immunological agents which can be directed to diseased tissue and can specifically bind to a subsequently administered targetable diagnostic or therapeutic conjugate, and a flexible, modular system that accommodates different diagnostic and therapeutic agents without alteration to the bi-specific or multi-specific antibodies. We have continued to develop the pretargeting system originally described by Janevik-lvanovska et al. that used an antibody directed against a histamine derivative, histamine-succinyl-glycl (HSG), as the recognition system on which a variety of effector substances could be prepared. Excellent pretargeting results have been reported using a radioiodinated and a rhenium-labeled divalent HSG-containing peptide. In the present work, we have expanded this system to include peptides that include haptens and/or chelators such as DTPA, and which may be suitable for radiolabeling with $^{90}Y$, $^{111}In$, and $^{177}Lu$, as well as $^{99m}Tc$.

SUMMARY

Disclosed herein are reagents for therapeutic use, for example, in radioimmunotherapy (RAIT), and diagnostic use, for example, in radioimmunodetection (RAID) and magnetic resonance imaging (MRI). In particular, disclosed herein are targetable molecules for use with binding molecules (i.e. targeting molecules), such as bi-specific antibodies (bsAb) and bi-specific antibody fragments (bsFab) that have at least one arm that specifically binds the targetable construct and at least one other arm that specifically binds a targeted tissue.

The compounds described herein include two or more haptens conjugated by a spacer. The haptens may include diethylenetriaminepentaacetate (DTPA), histimine-succinyl-glutamine (HSG), or combinations of DTPA and HSG. Preferably, the compound includes DTPA. In one embodiment, the compound includes DTPA and HSG. The compounds may be multivalent to facilitate crosslinking of one or more binding molecules on the surface of a targeted tissue to facilitate internalization of the crosslinked complex. The compounds may also include one or more moieties that facilitate internalization by binding to an internalized receptor on the surface of the targeted tissue (e.g., the folate receptor).

The compound also includes an effector molecule which may be conjugated to one or more of the haptens, the spacer, or both. As such, the haptens and/or the spacer may function as carrier molecules for the effector. The effector molecule may be conjugated by a number of linkages, and preferably, the linkage is stable under, physiological conditions in serum, but the linkage is sensitive to hydrolysis when the compounds are localized to target cells or internalized by target cells. For example, the linkages may be subject to acid hydrolysis under the physiological conditions present within lysosomes. Alternatively, hydrolysis of a particular linkage may be catalyzed by one or more enzymes localized at the target cells or internal to the target cells. Suitable linkages may include an ester linkage, an imino linkage, an amino linkage, a sulfide linkage, a thiosemicarbazone linkage, a semicarbazone linkage, an oxime linkage, an ether linkage, or combinations of these linkages.

The compound may also include metal ions. Preferably, the compound includes indium cations. In one embodiment, metal ions, such as indium, are chelated by a hapten such as DTPA.

The spacer may include one or more amino acids, and preferably the spacer includes three or more amino acids. In one embodiment, the peptide may include one or more D-amino acids, (e.g., to create a more stable molecule that is not easily metabolized in serum).

In one particular embodiment the spacer includes a peptide with one or more lysine residues and one or more cysteine residues. In another embodiment, the spacer includes a penicillamine moiety or a moiety that is a derivative of penicillamine. In a further embodiment, the spacer includes a thiolactic acid moiety or a moiety that is a derivative of thiolactic acid.

The haptens and/or effectors may be conjugated to one or more residues of the spacer. For example, the haptens may be conjugated to an ε-nitrogen atom of a lysine residue, or a sulfur atom of a cysteine residue. In another example, the effector is conjugated to a penicillamine moiety or a derivative thereof, or a thiolactic acid moiety or a derivative thereof.

Preferably, the effector molecule is linked by an ester linkage, or another linkage which may be hydrolyzed under physiological conditions after being administered to a subject.

As used herein, an effector molecule includes any molecule that brings about a desirable result. As such, an effector molecule many include drugs, prodrugs, toxins, enzymes, radioisotopes, immunomodulators, cytokines, hormones, nucleotide sequences (e.g., antisense nucleotides or interference RNAs), binding molecules (e.g., antibodies), or combinations of these types of molecules. Examples of antisense oligonucleotides and interference RNAs are disclosed in Kalota et al., *Cancer Biol. Ther.* 2004 January; 3(1); Tong et al., *Clin. Lung Cancer* 2001 February; 2(3): 220-6; Dean et al., *Oncogene* 2003 Dec. 8; 22(56): 9087-96; Nahta et al., *Semin. Oncol.* 2003 October; 30(5 Suppl 16): 143-9; Patry et al., *Cancer Res.* 2003 Nov. 15; 63(22): 7679-88; Duxbury et al., *Biochem Biophys Res Commun.* 2003 Nov. 21; 311 (3) 786-92; Crnkovic-Mertens et al., *Oncogene* 2003 Nov. 13; 22(51): 8330-6; Lipscomb et al., *Clin Exp Metastasis* 2003; 20(6): 569-76; Wall et al., *Lancet* 2003 Oct. 25; 362(9393): 1401-3; Bedford et al., *Semin Cancer Biol* 2003 August; 13(40): 301-8; Damm-Welk et al., *Semin Cancer Biol.* 2003 August; 13(4): 283-92; Duursma et al., *Semin Cancer Biol.* 2003 August; 13(4): 267-73, all of which are incorporated herein by reference in their entireties.

An effector may also include a lipid or a polymer, which may be capable of forming a higher-ordered structure, (e.g., a micelle, liposome, or polymeric structure), which may incorporate other effectors as described herein. Alternatively, the effector may be a higher-ordered structure itself (e.g., a micelle, liposome, polymeric structure, and/or a nanoparticle). Where the effector is a lipid, the lipid-conjugated compound may form an emulsion that is associated with any of the effectors as described herein.

Therapeutic effector molecules may include cytotoxic drugs, such as aplidin, azaribine, anastrozole, azacytidine, bleomycin, bortezomib, bryostatin-1, busulfan, calicheamycin, camptothecin, 10-hydroxycamptothecin, carmustine, celebrex, chlorambucil, cisplatin, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, 2-pyrrolinodoxorubicin (2P-DOX), cyano-morpholino doxorubicin, doxorubicin glucuronide, epirubicin glucuronide, ethinyl estradiol, estramustine, etoposide, etoposide glucuronide, etoposide phosphate, floxuridine (FUdR), 3',5'-O-dioleoyl-FudR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, semustine streptozocin, tamoxifen, taxanes, taxol, testosterone propionate, thalidomide, thioguanine, thiotepa, teniposide, topotecan, uracil mustard, velcade, vinblastine, vinorelbine, vincristine, ricin, abrin, ribonuclease, onconase, rapLR1, DNase I, *Staphylococcal enterotoxin*-A, pokeweed antiviral protein, gelonin, diphtheria toxin, *Pseudomonas exotoxin, Pseudomonas endotoxin*, or combinations of these.

In one embodiment, the effector molecule may be a prodrug that is activated after the compound is administered to a subject. For example, a prodrug may be activated after it is localized to a targeted cell and/or internalized by the targeted cell. In particular, the prodrug may be activated by physiological conditions in the cell (e.g., the acidic environment of lysosomes). Alternatively, the prodrug may be activated by one or more enzymes, (e.g., carboxylesterase can activate prodrugs such as irinotecan (CPT-11). Preferably, the effector molecule includes camptothecin, doxorubicin, or derivatives and/or analogs thereof, and preferably the effector molecule is conjugated by an ester linkage. Doxorubicin derivatives and/or analogs include 2-pyrrolinodoxorubicin (2P-DOX) and cyano-morpholino doxorubicin.

Where an effector molecule is not water soluble, preferably one or more of the haptens, the spacer (e.g., a peptide), and/or the linkage makes the effector molecule more water soluble. In one embodiment, an insoluble effector molecule may be administered as part of an emulsion or liposome, wherein the lipid that forms the emulsion or liposome may be conjugated to one or more of the administered compounds (e.g., the targetable construct). In another embodiment, one or more of the haptens, the spacer, and/or the linkage may reduce the toxicity of the effector molecule. In a further embodiment, one or more of the haptens, the spacer, and/or the linkage facilitate localization of the compound (which includes the effector molecule) to a targeted tissue, while non-targeted compounds (and/or effector molecules) can be rapidly excreted. As such, the biodistribution of the effector molecule may be altered by conjugating the effector to one or more of the haptens, the spacer, and/or the linkage.

The compound may also include an isotope. Examples include $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{75}Se$, $^{77}As$, $^{86}Y$, $^{89}Sr$, $^{89}Zr$, $^{90}Y$, $^{94}Tc$, $^{94m}Tc$, $^{99}Mo$, $^{99m}Tc$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-158}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$, or $^{225}Ac$. The isotope may be covalently linked to the compound or the isotope may be chelated by a chelating moiety present in the compound (e.g., DTPA).

In particular embodiments, the compound includes a peptide, one or more haptens, and one or more effector molecules. Further, the peptide may include one or more sequences $R^1$-Lys(X)-$R^2$-Lys(Y) or Lys(X)-$R^2$-Lys(Y)-$R^1$, where $R^1$ and $R^2$ include one or more amino acids, and where (X) and (Y) include one or more conjugated moieties selected from antigenic molecules, haptens, hard acid chelators, and soft acid chelators. The effector molecule, as described herein, may be conjugated by a linkage to the haptens and/or one or more amino acids present in $R^1$ or $R^2$. Desirably, the linkage is stable in physiological conditions in serum, but the linkage is susceptible to hydrolysis when the compound is internalized in a cell. For example, the linkage may be susceptible to hydrolysis under the acidic conditions in a lysosome or the linkage may be susceptible to hydrolysis as facilitated by an enzyme (e.g., carboxylesterase). Linkages may include an ester linkage, an imino linkage, an amino linkage, a sulfide linkage, a thiosemicarbazone linkage, a semicarbazone linkage, an oxime linkage, an ether linkage, an amide, and combinations of these linkages. As noted herein, the effector molecule may include drugs, prodrugs, toxins, enzymes, radioisotopes, immunomodulators, cytokines, hormones, nucleotide sequences, binding molecules, or combinations of these.

The moiety may be a hard acid chelator, and where the compound includes a hard acid chelator, preferably the compound further includes a cation selected from the group consisting of Group IIa and Group IIIa metal cations. The compound may also include one or more isotopes as described above.

In one embodiment, the moiety includes DTPA, HSG, DOTA, NOTA, TETA, Tscg-Cys, Tsca-Cys, nitroloacetic acid, or combinations of these moieties. Preferably, the compound includes DTPA, HSG, or combinations of DTPA and HSG. Most preferably, the compound includes DTPA. The moieties, designated by (X) and (Y), may be the same or different.

The compound may also include a soft acid chelator. Where the compound includes a soft acid chelator, the compound may also include a cation selected from the group consisting of transition metals, Bi, lanthanides, and actinides. For example, the compound may include Tc, Re, Bi, or combinations of these cations.

It may be desirable to synthesis peptides that include particular amino acids or types of amino acids. For example, in one embodiment the group designated by $R^2$ may include tyrosine. Also, it may be desirable to create a peptide that includes one or more D-amino acids.

Also disclosed herein is a method of treating and/or diagnosing a disease or condition that may lead to a disease in a patient, which may include: (1) administering a binding molecule to the patient, where the binding molecule has at least one arm that binds a targeted tissue and at least one other arm that binds a targetable construct; (2) optionally, administering a clearing composition to the patient and allowing the composition to clear non-localized binding molecules from circulation; and (3) administering to the patient one or more targetable constructs that include one or more of the above-described compounds. For example, the targetable construct may include one or more compounds that include: (1) two or more haptens linked by a spacer, where one or more haptens are DTPA or HSG; and (2) one or more effector molecules conjugated to one or more of the haptens, the spacer, or both. In one embodiment the targetable construct includes a compound that includes: (1) a peptide having one or more of the sequences $R^1$-Lys(X)-$R^2$-Lys(Y) or Lys(X)-$R^2$-Lys(Y)-$R^1$, where $R^1$ and $R^2$ include one or more amino acids and where (X) and (Y) include a conjugated moiety; and (2) an effector molecule conjugated to the peptide. The moiety may include an antigenic molecule, a hapten, a hard acid chelator, a soft acid chelator or combinations of these types of moieties.

As used herein, a binding molecule (i.e., a targeting molecule) may include an antibody or a fragment of an antibody. Particular suitable antibodies or binding molecules may be multivalent and multispecific (e.g., bi-specific antibodies). The binding molecule may include a monoclonal antibody or a fragment of a monoclonal antibody. The antibody or antibody fragment (e.g., monoclonal) may include a human, chimeric or humanized antibody or a fragment of a human, chimeric or humanized antibody. Examples of particular suitable antibodies include MAb 679, MAb 734, MAb Mu-9, MN-14, RS-7, 679, 734, or combinations of these antibodies. The binding molecule or antibody may include a fusion protein. In some embodiments, it may be desirable to use antibodies, fragments thereof, or binding molecules that include the CDRs of Mab 679, Mab 734, Mab Mu-9, MN-14, RS-7, 679, or 734.

As noted herein, the targetable construct may include a peptide including the sequence $R^1$-Lys(X)-$R^2$-Lys(Y) or Lys(X)-$R^2$-Lys(Y)-$R^1$, and an effector molecule conjugated to an amino acid present in $R^1$ or $R^2$ and/or to one or more of the conjugated moieties (X) and/or (Y). Preferably the effector molecule is conjugated by an ester linkage, an amido linkage, and/or a hydrazone linkage.

Also, as noted herein, the effector molecule may include any molecule that brings about a desirable result. For example, the effector molecule may include one or more drugs, prodrugs, toxins, enzymes, radioisotopes, immunomodulators, cytokines, hormones, nucleotide sequences (e.g., antisense oligonucleotide or interference RNAs), binding molecules, or molecules that facilitate administration of the foregoing categories of molecules (e.g., a lipid or polymer capable of forming a higher-ordered structure, or a higher-ordered structure itself, such as a micelle, liposome, polymeric structure, and/or nanoparticle), which may be useful as drug carriers. Specific examples of effector molecules are exemplified herein. In particular, the effector molecule may include camptothecin or a derivative of camptothecin, (e.g., SN-38, 10-hydroxy-CPT, 9-amino-CPT, irinotecan (CPT-11), etc.). Doxorubicin, or derivatives and/or analogs thereof, may also be a particularly suitable effector molecule. Doxorubicin derivatives are described in Nagy et al., *Proc. Natl. Acad. Sci. USA*, 1996, 93:2464-9. Antitumor anthracyclines may also be particularly suitable effector molecules, as described in Monneret, *Eur. J. Med. Chem.* 2001 36:483-93. The effector molecule, (e.g., camptothecin and/or doxorubicin), may be conjugated to the targetable construct and/or associated with a drug-carrier such as a micelle/liposome or an emulsion, wherein the drug-carrier is conjugated to the targetable construct.

In regard to selected enzymes as effector molecules, particularly suitable enzymes may include carboxylesterases, glucuronidases, carboxypeptidases, beta-lactamases, phosphatases, or mixtures of these enzymes.

The methods of treating and/or diagnosing diseases or conditions may be used to treat/diagnose a variety of diseases or conditions. For example, a malignant disease, a cardiovascular disease, an infectious disease, an inflammatory disease, an autoimmune disease, a metabolic disease, a neurological disease, or combinations of these diseases or conditions.

Where the disease or condition is a malignant disease, the binding molecule may specifically bind to a targeted tissue that includes an antigen selected from the group consisting of carcinoembryonic antigen, tenascin, epidermal growth factor receptor, platelet derived growth factor receptor, fibroblast growth factor receptors, vascular endothelial growth factor receptors, gangliosides, HER/2neu receptors and mixtures of these antigens. The targeted tissue may also include a tumor. The binding molecule may specifically bind to antigens produced by or associated with the tumor including colon-specific antigen-p (CSAp), carcinoembryonic antigen (CEA), CD4, CD5, CD8, CD14, CD15, CD19, CD20, CD21, CD22, CD23, CD25, CD30, CD45, CD74, CD80, HLA-DR, Ia, Ii, MUC 1, MUC 2, MUC 3, MUC 4, NCA, EGFR, HER 2/neu, PAM-4, TAG-72, EGP-1, EGP-2, A3, KS-1, Le(y), S100, PSMA, PSA, tenascin, folate receptor, VEGF, PlGF, ILGF-1, necrosis antigens, IL-2, IL-6, T101, MAGE, and combinations of these antigens. Particularly useful antigens include CD74 and EGP-1, which may facilitate internalization of the bound antibody. Antibodies that recognize CD74 include LL1, the use of which is described in U.S. Pat. Nos. 6,458,933; 6,395,276; 6,083,477; and U.S. 2003-0103982. Antibodies that recognize EGP-1 include RS7, which is described in U.S. Ser. No. 10/377,121; U.S. Pat. No. 5,635,603; and Stein et al., 1990, *Cancer Res.*, 50, 1330-1336.

The targeted tissue may include a multiple myeloma, a B-cell malignancy, or a T-cell malignancy. Specific B-cell malignancies may include indolent forms of B-cell lymphomas, aggressive forms of B-cell lymphomas, chronic leukemias, multiple myeloma, and acute lymphatic leukemias. The targeted tissue may also include a lymphoma such as a non-Hodgkin's lymphoma or a Hodgkin's lymphoma.

In addition, the targeted tissue(s) may include a solid tumor, such as a melanoma, a carcinoma, a sarcoma, a glioma, or combinations of these malignancies. Particular carcinomas may include esophageal, gastric, colonic, rectal, pancreatic, lung, breast, ovarian, urinary bladder, endometrial, cervical, testicular, renal, adrenal, liver cancer, or combinations of these carcinomas.

The disease or condition may also include a cardiovascular disease that is associated with granulocytes, lymphocytes, monocytes, D-dimer, and/or fibrin deposits. As such, the binding molecule (i.e., targeting molecule) may specifically bind to antigens that are present on granulocytes, lymphocytes, monocytes, and/or fibrin. Particular cardiovascular diseases or conditions may include a myocardial infarction, ischemic heart disease, atherosclerotic plaques, fibrin clots, emboli, or a combinations of these disease or conditions.

The method may also be used to treat and/or diagnose infectious diseases, for example, bacterial disease, fungal disease, parasitic disease, viral disease, protozoan disease, mycoplasmal, and combinations of these infectious diseases. In particular, the infectious disease may be caused by a pathogen selected from the group consisting of *Microsporum, Trichophyton, Epidermophyton, Sporothrix schenckii, Cryptococcus neoformans, Coccidioides immitis, Histoplasma capsulatum, Blastomyces dermatitidis, Candida albicans*, human immunodeficiency virus (HIV), herpes virus, cytomegalovirus, rabies virus, influenza virus, hepatitis B virus, Sendai virus, feline leukemia virus, Reovirus, poliovirus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus, blue tongue virus, *Anthrax bacillus, Streptococcus agalactiae, Legionella pneumophilia, Streptococcus pyogenes, Escherichia coli, Neisseria gonorrhoeae, Neisseria meningitidis, Pneumococcus*, Hemophilis influenzae B, *Treponema pallidum*, Lyme disease spirochetes, *Pseudomonas aeruginosa, Mycobacterium leprae, Brucella abortus, Mycobacterium tuberculosis*, Tetanus, a helminth, a malaria parasite, *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Babesia bovis, Elmeria tenella, Onchocerca volvulus, Leishmania tropica, Trichinella spiralis, Onchocerca volvulus, Theileria parva, Taenia hydatigena, Taenia ovis, Taenia saginata, Echinococcus granulosus, Mesocestoides corti, Mycoplasma arthritidis, Mycoplasma hyorhinis, Mycoplasma orale, Mycoplasma arginini, Acholeplasma laidlawii, Mycoplasma salivarum, Mycoplasma pneumoniae*, and combinations of these pathogens.

The method may also be used to treat and/or diagnose autoimmune diseases or conditions, such as acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcalnephritis, erythema nodosurn, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitisubiterans, Sjogren's syndrome, primary biliary cirrhosis, Hashimoto's thyroiditis, thyrotoxicosis, scleroderma, chronic active hepatitis, polymyositis/dermatomyositis, polychondritis, parnphigus vulgaris, Wegener's granulomatosis, membranous nephropathy, amyotrophic lateral sclerosis, tabes dorsalis, giant cell arteritis/polymyalgia, perniciousanemia, rapidly progressive glomerulonephritis, psoriasis, fibrosing alveolitis, and combinations of these diseases or conditions.

Neurological diseases may also be treated or diagnosed by using the method. For example, a neurological disease characterized by a metabolic disorder, such as amyloidosis, may be treated or diagnosed by the method where the targeted tissue includes an amyloid deposit.

In addition to administering the binding molecule, optionally the clearing agent, and the targetable molecule, the method may also include administering one or more additional therapeutic or diagnostic agents. Suitable therapeutic or diagnostic agents may include binding molecules (e.g., antibodies or fragments thereof), drugs, prodrugs, toxins, enzymes, enzyme-inhibitors, nucleases, hormones, hormone antagonists, immunomodulators, cytokines, chelators, boron compounds, uranium atoms, photoactive agents, radionuclides, and combinations of these agents. The agents may be administering before, simultaneously, or after administration of the binding molecule, the optional clearing agent, and the targetable molecule. Further, the agents may be conjugated to one or more of the binding molecule, clearing agent, and/or the targetable construct. The agents may also be administered in combination with an emulsion or liposome, which may be conjugated to a compound such as the targetable construct.

In one embodiment, the therapeutic agent includes a cytokine selected from the group consisting of IL-1, IL-2, IL-3, IL-6, IL-10, IL-12, IL-18, IL-21, interferon-α, interferon-β, interferon-γ, G-CSF, and GM-CSF, and mixtures of these cytokines. In another embodiment, the therapeutic agent includes an anti-angiogenic agent selected from the group consisting of angiostatin, endostatin, basculostatin, canstatin, maspin, anti-VEGF antibodies, anti-placental growth factor antibodies, anti-vascular growth factor antibodies, and mixtures of these anti-angiogenic agents.

The method may include administering a diagnostic agent selected from radioisotopes, dyes, radioopaque materials, contrast agents, fluorescent compounds, enhancing agents, and combinations of these diagnostic agents.

It may be desirable to further administer a metal as a therapeutic or diagnostic agent. For example, zinc, aluminum, gallium, lutetium, palladium, boron, gandolinium, uranium, manganese, iron, chrominum, copper, cobalt, nickel, dysprosium, rhenium, europium, terbium, holmium, neodymium, and combinations of these metals may be administered.

Paramagnetic ions, useful for diagnostic procedures, may also be administered. Examples of paramagnetic ions include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III), erbium (III), or combinations of these paramagnetic ions.

The therapeutic and/or diagnostic agent may include one or more agents for photodynamic therapy, (e.g., a photosensitizer). Photosensitizers may include a benzoporphyrin monoacid ring A (BDP-MA), tin etiopurpurin (SnET2), sulfonated aluminum phthalocyanine (AISPc) and lutetium texaphyrin (Lutex).

Therapeutic or diagnostic nuclides may also be administered, including $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$G, $^{75}$Se, $^{77}$As, $^{86}$Y, $^{89}$Sr, $^{89}$Zr, $^{90}$Y, $^{94}$Tc, $^{94m}$Tc, $^{99}$Mo, $^{99m}$Tc, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154-158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb $^{212}$Bi, $^{212}$Pb, $^{213}$Bi, $^{223}$Ra, $^{225}$Ac, and mixtures of these nuclides. Particularly suitable therapeutic nuclides may include $^{32}$P, $^{33}$P, $^{47}$Sc, $^{64}$Cu, $^{67}$Cu, $^{67}$Ga, $^{90}$Y, $^{111}$Ag, $^{111}$In, $^{123}$I, $^{131}$I, $^{142}$Pr, $^{153}$Sm, $^{161}$Tb, $^{166}$Dy, $^{166}$Ho, $^{177}$Lu, $^{186}$Re, $^{188}$Re, $^{189}$Re, $^{211}$At, $^{212}$Pb, $^{212}$Bi, $^{213}$Bi, $^{223}$Ra, $^{225}$Ac, or mixtures of these nuclides. Therapeutic nuclides may emit gamma particles and/or positrons that have an energy of about 70 to about 700 keV.

Particularly suitable diagnostic nuclides may include $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94}$Tc, $^{94m}$Tc, $^{99m}$Tc, $^{111}$In, $^{123}$I, $^{124}$I, $^{125}$I, $^{131}$I, or mixtures of these nuclides. Diagnostic nuclides may emit gamma particles and/or positrons that have an energy of between about 25 to about 4000 keV.

The diagnostic agent may be useful when imaging methods are performed. For example, nuclides such as $^{18}$F may be included to perform positron emission tomography (PET). Alternatively, image enhancing agents useful for performing magnetic resonance imaging (MRI) may be included. Image enhancing agents may include gadolinium ions, lanthanum ions, manganese ions, iron, chromium, copper, cobalt, nickel, fluorine, dysprosium, rhenium, europium, terbium, holmium, neodymium, or mixtures of these agents. In another embodiment, one or more radiopaque agents or contrast agents for X-ray or computed tomography (CT) may be included. Radiopaque or contrast agents may include barium, diatrizoate, ethiodized oil, gallium citrate, iocarmic acid, iocetamic acid, iodamide, iodipamide, iodoxamic acid, iogulamide, iohexol, iopamidol, iopanoic acid, iopromic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, thallous chloride, or combinations of these agents.

The method may also include administering one or more ultrasound contrast agents such as a liposome or dextran. Liposomes may be gas-filled.

The therapeutic and/or diagnostic method may also include performing an operative, intravascular, laparoscopic, or endoscopic procedure, either before, simultaneously, or after the therapeutic and/or diagnostic method.

BRIEF DESCRIPTION OF THE DRAWINGS

FIG. 1 is a schematic representation of the structure of Bis In$^{3+}$ IMP 274.

FIG. 2 is a schematic representation of the structure of a SN-38 analog/derivative of Bis In$^{3+}$ IMP 274.

FIG. 3 is a schematic representation of the structure of a SN-38 analog/derivative of Bis In$^{3+}$ IMP 274 with SN-38 conjugated to a cysteine by a penicillamine linkage.

FIG. 4 is a schematic representation of the structure of a SN-38 analog/derivative of Bis In$^{3+}$ IMP 274 with SN-38 conjugated to a cysteine by a hindered ester linkage.

FIG. 5 is a schematic representation of the structure of IMP 225.

FIG. 6 is a schematic representation of the structure of Bis In$^{3+}$ IMP 224.

FIG. 7 is a graphic representation of the HPLC analysis (reverse phase) of In$^{3+}$ IMP 274 after storage.

FIG. 8 is a graphic representation of the HPLC analysis (size exclusion) of In$^{3+}$ IMP 274 after storage.

FIGS. 9A and B are graphic representations of the HPLC analysis (reverse phase) of In$^{3+}$ IMP 274 incubated with mouse serum.

FIG. 10A and B are graphic representations of the HPLC analysis (reverse phase) of In$^{3+}$ IMP 274 incubated with human serum.

FIG. 11 is a graphic representation of the HPLC analysis (size exclusion) of In$^{3+}$ IMP 274 incubated with mouse serum containing bsAb 734×hMN14.

FIG. 12 is a graphic representation of the HPLC analysis (size exclusion) of In$^{3+}$ IMP 274 incubated with human serum containing bsAb 734×hMN14.

FIG. 13. is a graphic representation of the stability of IMP 294 (A) and IMP. 295 (B) over a one week period. Samples were analyzed ori day 0, 1, 2, 3, 6, and 7.

FIG. 14 displays the results of a pre-targeting experiment using LL2x734 bi-specific antibody and IMP-225 peptide in SCID mice inoculated with Daudi (Burkitt's lymphoma cells).

FIG. 15 is a schematic representation of a method for synthesizing a DTPA precursor and DTPA using a three step method.

FIG. 16 is a schematic representation of a method for synthesizing a DTPA precursor and DTPA using a four step method.

DETAILED DESCRIPTION OF THE PREFERRED EMBODIMENTS

Unless otherwise specified, "a" or "an" means "one or more".

"Predominantly" means "substantially" and/or at least 90%.

Overview

Disclosed herein are compounds that may be useful as targetable constructs for therapeutic or diagnostic methods. The targetable construct may be specifically bound by a binding molecule such as a bi-specific antibody (bsAb) or antibody fragment (bsFab), which has at least one arm that binds the targetable construct and at least one other arm that binds a targeted tissue. Desirably, the targetable construct includes a peptide having at least two units of a recognizable hapten. Examples of recognizable haptens include, but are not limited to, DTPA and HSG. The targetable construct is conjugated to an effector molecule, which includes a variety of agents useful for treating or identifying diseased tissue. Examples of conjugated haptens and/or effector molecules include, but are not limited to, chelators, metal chelate complexes, drugs, enzymes, and toxins (e.g., ricin, abrin, ribonuclease (e.g., RNase), DNase I, *Staphylococcal enterotoxin*-A, pokeweed antiviral protein, gelonin, diphtherin toxin, *Pseudomonas exotoxin, Pseudomonas endotoxin*). Effector molecules may include lipids or polymers, which may be associated with other effector molecules described herein. For example, lipids or polymers may form higher-ordered structures such as micelles/liposomes or polymeric structures. Effector molecules may include nanoparticles, which can be used to deliver effector molecules as described herein.

Bi-specific antibody (bsAb) pretargeting represents a potentially non-immunogenic, highly selective alternative for diagnostic and therapeutic applications. The bsAb pretargeting system described herein represents an additional significant advantage over other pretargeting systems in that it potentially can be developed for use with a variety of different imaging or therapeutic agents. The flexibility of this system is based on use of an antibody directed against DTP or HSG and the development of peptides containing the DTP or HSG residue. DTP-containing and/or HSG-containing peptides can be synthesized, and where the peptide contains DTP, the peptide can be labeled with chelated nuclides, such as $^{111}$In, $^{90}$Y, or $^{177}$Lu, which may be useful in therapy or diagnosis. Antibodies have been generated against the DTPA-$^{111}$In moiety. For pretargeting, the selected peptides can be used in combination with bi-specific antibodies using the anti-DTPA-[111]In Fab' fragment or the anti-HSG Fab' fragment chemically stabilized with the Fab' fragment of either an anti-carcinoembryonic antigen antibody (anti-CEA) or an anti-colon-specific antigen-p antibody (anti-CSAp) to provide tumor targeting capability for tumors expressing these antigens. However, other antigen targets may include diverse tumor-associated antigens known in the art, such as against CD19, CD20, CD21, CD22, CD23, CD30, CD74, CD 80, HLA-DR, Ia, MUC 1, MUC 2, MUC 3, MUC 4, EGFR, HER 2/neu, PAM-4, BrE3, TAG-72 (B72.3, CC49), EGP-1 (e.g., RS7), EGP-2 (e.g., 17-1A and other Ep-CAM targets), Le(y) (e.g., B3), A3, KS-1, S100, IL-2, T101, necrosis antigens, folate receptors, angiogenesis markers (e.g., VEGF), tenascin, PSMA, PSA, tumor-associated cytokines, MAGE and/or fragments thereof. Tissue-specific antibodies (e.g., against bone marrow cells, such as CD34, CD74, etc., and parathyroglobulin antibodies, etc.) as well as antibodies against non-malignant diseased tissues, such as fibrin and/or D-dimer of clots, macrophage antigens of atherosclerotic plaques (e.g., CD74 antibodies), and also specific pathogen antibodies (e.g., against bacteria, viruses, and parasites) are well known in the art.

The peptide described herein can be radiolabeled to a high specific activity in a facile manner that avoids the need for purification. In vivo studies in tumor bearing nude mice showed the radiolabeled peptides cleared rapidly from the body with minimal retention in tumor or normal tissues. See, e.g., Tables 1-12, 14, and 16-18, which show that the pretargeting system is highly flexible, being capable of using a wide array of compounds of diagnostic imaging and therapeutic interest. By achieving excellent tumor uptake and targeting ratios, the disclosed pretargeting system is highly promising for use in many applications.

Additionally encompassed is a method for detecting and/or treating target cells, tissues or pathogens in a mammal, comprising administering an effective amount of a binding molecule (e.g., a bi-specific antibody or antibody fragment) comprising at least one arm that specifically binds a targeted tissue and at least one other arm that specifically binds a targetable construct. As used herein, the term "pathogen" includes, but is not limited to fungi (e.g., *Microsporum, Trichophyton, Epidermophyton, Sporothrix schenckii, Cryptococcus neoformans, Coccidioides immitis, Histoplasma Capsulatum, Blastomyces dermatitidis, Candida albicans*), viruses (e.g., human immunodeficiency virus (HIV), herpes virus, cytomegalovirus, rabies virus, influenza virus, hepatitis B virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus and blue tongue virus), parasites, bacteria (e.g., *Anthrax bacillus, Streptococcus agalactiae, Legionella pneumophilia, Streptococcus pyogenes, Escherichia coli, Neisseria gonorrhoeae, Neisseria meningitidis, Pneumococcus,* Hemophilis influenzae B, *Treponema pallidum,* Lyme disease spirochetes, *Pseudomonas aeruginosa, Mycobacterium leprae, Brucella abortus, Mycobacterium tuberculosis* and *Tetanus toxin*), mycoplasma (e.g., *Mycoplasma arthritidis, M. hyorhinis, M. orale, M. arginini, Acholeplasma laidlawii, M. salivarum,* and *M. pneumoniae*) and protozoans (e.g., *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Babesia bovis, Elmeria tenella, Onchocerca volvulus, Leishmania tropica, Trichinella spiralis, Onchocerca volvulus, Theileria parva, Taenia hydatigena, Taenia ovis, Taenia saginata, Echinococcus granulosus* and *Mesocestoides corti*). See U.S. Pat. No. 5,332,567.

Also disclosed herein are binding molecules which include antibodies and antibody fragments. The antibody fragments are antigen binding portions of an antibody, such as Fab or $F(ab)_2$ and the like. The antibody fragments bind to the same antigen that is recognized by the intact antibody. For example, an anti-CD22 monoclonal antibody fragment binds to an epitope of CD22.

The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("sFv proteins"), and minimal recognition units consisting of the amino acid residues that mimic the "hypervariable region." Three of these so-called "hypervariable" regions or "complementarity-determining regions" (CDR) are found in each variable region of the light or heavy chain. Each CDR is flanked by relatively conserved framework regions (FR). The FR are thought to maintain the structural integrity of the variable region. The CDRs of a light chain and the CDRs of a corresponding heavy chain form the antigen-binding site. The "hypervariability" of the CDRs accounts for the diversity of specificity of antibodies.

As used herein, the term "subject" and "patient" refer to any animal (i.e., vertebrates and invertebrates) including, but not limited to humans and other primates, rodents (e.g., mice, rats, and guinea pigs), lagamorphs (e.g., rabbits), bovines (e.g., cattle), ovines (e.g., sheep), caprines (e.g., goats), porcines (e.g., swine), equines (e.g., horses), canines (e.g., dogs), felines (e.g., cats), domestic fowl (e.g., chickens, turkeys, ducks, geese, other gallinaceous birds, etc.), as well as feral or wild animals, including, but not limited to, such animals as ungulates (e.g., deer), bear, fish, lagamorphs, rodents, birds, etc. It is not intended that the term be limited to a particular age or sex. Thus, adult and newborn subjects, as well as fetuses, whether male or female, are encompassed by the term.

Constructs Targetable to Antibodies

As noted, the above-described compounds can be used as targetable constructs. The targetable construct can be of diverse structure, but is selected not only to diminish the elicitation of immune responses, but also for rapid in vivo clearance when used within the bsAb targeting method. Hydrophobic agents are best at eliciting strong immune responses, whereas hydrophilic agents are preferred for rapid in vivo clearance, thus, an ideal construct will possess both hydrophobic and hydrophilic qualities. This is accomplished, in part, by relying on the use of hydrophilic chelating agents (such as DTPA) to offset the inherent hydrophobicity of many organic effectors (e.g., toxins such as camptothecin). Also, sub-units of the targetable construct may be chosen which have opposite solution properties, for example, peptides, which contain amino acids, some of which are hydrophobic and some of which are hydrophilic. Aside from peptides, carbohydrates may also be used or other suitable molecules may be used to synthesize the compounds described herein.

The targetable construct may include a peptide backbone (e.g., as a spacer) having as few as two amino-acid residues, (with preferably two to ten amino acid residues), and the backbone may be coupled to other moieties such as chelating agents. The targetable construct should be a low molecular weight construct, preferably having a molecular weight of less than 50,000 daltons, and advantageously less than about 20,000 daltons, 10,000 daltons or 5,000 daltons, including any metal ions that may be bound to the chelating agents. For instance, the known peptide DTPA-Tyr-Lys(DTPA)-OH (wherein DTPA is diethylenetriaminepentaacetic acid) has been used to generate antibodies against the indium-DTPA portion of the molecule, as noted above. However, by use of the non-indium-containing molecule, and appropriate screening steps, new Abs against the tyrosyl-lysine dipeptide can also be made. More usually, the antigenic peptide of the targetable construct will have four or more residues, such as the peptide N-acetyl-Cys-Lys(DTPA)-Tyr-Lys(DTPA)-NH$_2$ (SEQ ID NO:1).

The haptens of the targetable construct also provide an immunogenic recognition moiety. Using a hapten such as a DTPA or HSG hapten, bsAbs with high specificity for the construct can be generated. This occurs because antibodies raised to the DTPA or HSG hapten are known and can be easily incorporated into the appropriate bsAb. Thus, coupling of the haptens to the peptide backbone would result in a targetable construct that is specifically recognized by the bsAb or bsFab.

The compound may incorporate unnatural amino acids, e.g., D-amino acids, into a peptide backbone structure to ensure that, when used with the final bsAb/construct system, the arm of the bsAb which recognizes the targetable construct is completely specific. Further, other backbone structures such as those constructed from other non-natural amino acids and peptoids may be present in the compound. Incorporation of D-amino acids and/or L-amino acids can also be used to control the stability of a peptide Peptides to be used as immunogens are synthesized conveniently on an automated peptide synthesizer using a solid-phase support and standard techniques of repetitive orthogonal deprotection and coupling. Free amino groups in the peptide, that are to be used later for chelate conjugation, are advantageously blocked with standard protecting groups such as an acetyl group. Such protecting groups will be known to the skilled artisan. See Greene and Wuts Protective Groups in Organic Synthesis, 1999 (John Wiley and Sons, N.Y.). When the peptides are prepared for later use within the bsAb system, they are advantageously cleaved from the resins to generate the corresponding C-terminal amides, in order to inhibit in vivo carboxypeptidase activity. Methods for preparing targetable constructs are described in U.S. patent application Ser. Nos. 09/337,756; 09/382,186; 09/823,746; and 10/150,654; all of which are incorporated herein by reference.

Chelate Moieties

The presence of hydrophilic chelate moieties on the targetable construct helps to ensure rapid in vivo clearance. In addition to hydrophilicity, chelators are chosen for their metal-binding properties, and may be changed at will because, at least for those targetable constructs for which the bsAb epitope is not the chelator, recognition of the metal-chelate complex is not required.

Particularly useful metal-chelate combinations include 2-benzyl-DTPA and its monomethyl and cyclohexyl analogs, used with $^{47}$SC, $^{52}$Fe, $^{55}$Co, $^{67}$Ga, $^{68}$Ga, $^{111}$In, $^{89}$Zr, $^{90}$Y, $^{161}$Tb, $^{177}$Lu, $^{212}$Bi, $^{213}$Bi, and $^{225}$Ac for radio-imaging and RAIT. The same chelators, when complexed with non-radioactive metals such as Mn, Fe and Gd for use with MRI, may be used along with the bsAbs of the methods described herein. Macrocyclic chelators such as NOTA (1,4,7-triaza-cyclononane-N,N,N-triacetic acid), DOTA, and TETA (p-bromoacetamido-benzyl-tetraethylaminetetraacetic acid) are of use with a variety of metals and radiometals, most particularly with radionuclides of Ga, Y and Cu, respectively.

DTPA and DOTA-type chelators, where the ligand includes hard base chelating functions, such as carboxylate or amine groups, are most effective for chelating hard acid cations, especially Group IIa and Group IIIa metal cations. Such metal-chelate complexes can be made very stable by tailoring the ring size to the metal of interest. Other ring-type chelators such as macrocyclic polyethers are of interest for stably binding nuclides such as $^{223}$Ra for RAIT. Porphyrin chelators may be used with numerous radiometals, and are also useful as certain cold metal complexes for bsAb-directed immuno-phototherapy. Also, more than one type of chelator may be conjugated to the targetable construct to bind multiple metal ions, e.g., cold ions, diagnostic radionuclides and/or therapeutic radionuclides.

Particularly useful diagnostic radionuclides that can be bound to the chelating agents of the targetable construct include, but are not limited to, $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, or other gamma-, beta-, or positron-emitters. Preferably, the diagnostic radionuclides include a decay energy in the range of 25 to 10,000 keV, more preferably in the range of 25 to 4,000 keV., and even more preferably in the range of 20 to 1,000 keV, and still more preferably in the range of 70 to 700 keV. Total decay energies of useful positron-emitting radio-nuclides are preferably <2,000 keV, more preferably under 1,000 keV, and most preferably <700 keV. Radionuclides useful as diagnostic agents utilizing gamma-ray detection include, but are not limited to: $^{51}$Cr, $^{57}$Co, $^{58}$Co, $^{59}$Fe, $^{67}$Cu, $^{67}$Ga, $^{75}$Se, $^{97}$Ru, $^{99m}$Tc, $^{111}$In, $^{114m}$In, $^{123}$I, $^{125}$I, $^{131}$I, $^{169}$Yb, $^{197}$Hg, and $^{201}$TI. Decay energies of useful gamma-ray emitting radionuclides are preferably 20-2000 keV, more preferably 60-600 keV, and most preferably 100-300 keV.

Particularly useful therapeutic radionuclides that can be bound to the chelating agents of the targetable construct include, but are not limited to, $^{111}$In, $^{177}$Lu, $^{212}$Bi, $^{213}$Bi, $^{211}$At, $^{62}$Cu, $^{64}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. The therapeutic radionuclide preferably has a decay energy in the range of 25 to 10,000 keV. Decay energies of useful beta-particle-emitting nuclides are preferably 25-5,000 keV, more preferably 100-4,000 keV, and most preferably 500-2, 500 keV. Also preferred are radionuclides that substantially decay with Auger-emitting particles. For example, $^{58}$Co, $^{67}$Ga, $^{80m}$Br, $^{99m}$Tc, $^{103m}$Rh, $^{109}$Pt, $^{111}$In, $^{119}$Sb, $^{125}$I, $^{161}$Ho, $^{189m}$Os and $^{192}$Ir. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: $^{152}$Dy, $^{211}$At, $^{212}$Bi, $^{223}$Ra, $^{219}$Rn, $^{215}$Po, $^{211}$Bi, $^{225}$Ac, $^{221}$Fr, $^{217}$At, $^{213}$Bi and $^{225}$Fm. Decay energies of useful alpha-particle-emitting radionuclides are preferably 2,000-9,000 keV, more preferably 3,000-8,000 keV, and most preferably 4,000-7,000 keV.

Chelators such as those disclosed in U.S. Pat. No. 5,753, 206, especially thiosemi-carbazonylglyoxylcysteine (Tscg-Cys) and thiosemicarbazinyl-acetylcysteine (Tsca-Cys)

chelators are advantageously used to bind soft acid cations of Tc, Re, Bi and other transition metals, lanthanides and actinides that are tightly bound to soft base ligands, especially sulfur- or phosphorus-containing ligands. It may be useful to link more than one type of chelator to a peptide, (e.g., a hard acid chelator like DTPA for In(III) cations, and a soft acid chelator like Tscg-Cys for Tc cations). Because antibodies to a di-DTPA hapten are known (Barbet '395, supra) and are readily coupled to a targeting antibody to form a bsAb, it is possible to use a peptide with a cold di-DTPA chelator (e.g., not chelated with a radioisotope) and a chelator with a radioisotope in a pretargeting protocol for targeting the radioisotope to diseased tissue. One example of such a peptide is Ac-Lys(DTPA)-Tyr-Lys(DTPA)-Lys(Tscg-Cys)-$NH_2$ (SEQ ID NO:2). This peptide can be preloaded with In(III) and then labeled with $^{99M}Tc$ cations, the In(III) ions being preferentially chelated by the DTPA and the Tc cations binding preferentially to the thiol-containing Tscg-Cys. Other hard acid chelators such as NOTA, DOTA, TETA and the like can be substituted for the DTPA groups, and Mabs specific to them can be produced using analogous techniques to those used to generate the anti-di-DTPA Mab.

It will be appreciated that two different hard acid or soft acid chelators can be incorporated into the linker, (e.g., with different chelate ring sizes), to bind preferentially to two different hard acid or soft acid cations, based on the differing sizes of the cations, the geometries of the chelate rings, and the preferred complex ion structures of the cations. This will permit two different metals, one or both of which may be radioactive or useful for MRI enhancement, to be incorporated into a linker for eventual capture by a pretargeted bsAb.

Chelators are coupled to the peptides of the targetable construct using standard chemistries, some of which are discussed more fully in the working examples below. See also Karacay et al. *Bioconjugate Chem.* 11:842-854 (2000); and U.S. patent application Ser. Nos. 09/337,756; 09/382,186; 09/823,746; and 10/150,654; all of which are incorporated herein by reference. The protecting group abbreviations "Aloc" and "Fmoc" used herein refer to the groups allyloxycarbonyl and fluorenylmethyloxy carbonyl.

General Methods for Preparation of Metal Chelates

Chelator-peptide conjugates may be stored for long periods as solids. They may be metered into unit doses for metal-binding reactions, and stored as unit doses either as solids, aqueous or semi-aqueous solutions, frozen solutions or lyophilized preparations. They may be labeled by well-known procedures.

Typically, a hard acid cation is introduced as a solution of a convenient salt, and is taken up by the hard acid chelator and possibly by the soft acid chelator. However, later addition of soft acid cations leads to binding thereof by the soft acid chelator, displacing any hard acid cations which may be chelated therein. For example, even in the presence of an excess of cold $^{111}InCl_3$, a soft acid chelator may be labeled quantitatively with Tc cations provided by $^{99m}Tc(V)$ glucoheptonate or generated in situ with stannous chloride and $^{99m}Na$—$TcO_4$.

Other soft acid cations such as $^{186}Re$, $^{188}Re$, $^{213}Bi$ and divalent or trivalent cations of Mn, Co, Ni, Pb, Cu, Cd, Au, Fe, Ag (monovalent), Zn and Hg, especially $^{64}Cu$ and $^{67}Cu$, and the like, some of which are useful for radioimmunodetection or radioimmunotherapy, may be loaded onto the linker peptide by analogous methods. Rhenium cations also can be generated in situ from perrhenate and stannous ions or a prereduced rhenium glucoheptonate or other transchelator can be used. Because reduction of perrhenate requires more stannous ion (typically above 200 g/mL final concentration) than is needed for the reduction of Tc, extra care needs to be taken to ensure that the higher levels of stannous ion do not reduce sensitive disulfide bonds such as those present in disulfide-cyclized peptides. During radiolabeling with rhenium, similar procedures are used as are used with the $^{99m}Tc$. One method for the preparation of ReO metal complexes of the Tscg-Cys ligands is by reacting the peptide with $ReOCl_3(P(Ph3)_2$ but it is also possible to use other reduced species such as $ReO(ethylenediamine)_2$.

Other methods for preparing metal-chelate complexes are described in U.S. patent application Ser. Nos. 09/337,756; 09/382,186; 09/823,746; and 10/150,654; all of which are incorporated herein by reference.

Methods of Administering Targetable Constructs, bsAbs, and Additional Therapeutic or Diagnostic Agents It should be noted that much of the discussion presented hereinbelow focuses on the use of bi-specific antibodies and targetable constructs in the context of treating diseased tissue. However, also contemplated is the use of the targetable constructs and bi-specific antibodies in treating and/or imaging normal tissue and organs using the methods described in U.S. Pat. Nos. 6,126,916; 6,077,499; 6,010,680; 5,776,095; 5,776,094; 5,776,093; 5,772,981; 5,753,206; 5,746,996; 5,697,902; 5,328,679; 5,128,119; 5,101,827; and 4,735,210, which are incorporated herein by reference. As used herein, the term "tissue" refers to tissues, including but not limited to, tissues from the ovary, thymus, parathyroid, bone marrow or spleen. An important use when targeting normal tissues is to identify and treat them when they are ectopic (ie., displaced from their normal location), such as in endometriosis.

The targetable construct and/or bsAb may be administered intravenously, intraarterially, intraoperatively, endoscopically, intraperitoneally, intramuscularly, subcutaneously, intrapleurally, intrathecally, by perfusion through a regional catheter, or by direct intralesional injection, orally, and can be by continuous infusion or by single or multiple boluses or through other methods known to those skilled in the art for diagnosing (detecting) and treating diseased tissue. Further, the targetable construct may include agents for other methods of detecting and treating diseased tissue including, without limitation, conjugating dextran or liposome formulations to the targetable construct for use with ultrasound, or other contrast agents for use with other imaging modalities, such as X-ray, CT, PET, SPECT and ultrasound, as previously described.

The administration of a bsAb and the targetable construct discussed above may be conducted by administering the bsAb at some time prior to administration of the therapeutic agent (i.e., effector) which is associated with the linker moiety. The doses and timing of the reagents can be readily devised by a skilled artisan, and are dependent on the specific nature of the reagents employed. If a bsAb-F(ab')$_2$ derivative is given first, then a waiting time of 1-6 days before administration of the targetable construct may be appropriate. If an IgG-Fab' bsAb conjugate is the primary targeting vector, then a longer waiting period before administration of the linker moiety may be indicated, in the range of 3-15 days. Alternatively, the bsAb and the targetable construct may be administered substantially at the same time in either a cocktail form or by administering one after the other.

A wide variety of diagnostic and therapeutic reagents can be advantageously conjugated to the targetable construct. Generally, diagnostic and therapeutic agents can include isotopes, drugs, toxins, oligonucleotides (e.g., antisense oligonucleotides and interference RNAs), cytokines, conjugates with cytokines, hormones, growth factors, conjugates, radionuclides, contrast agents, metals, cytoxoic drugs, and immune modulators. For example, gadolinium metal is used for magnetic resonance imaging and fluorochromes can be conjugated for photodynamic therapy. Moreover, contrast agents can be MRI contrast agents, such as gadolinium ions, lanthanum ions, manganese ions, iron, chromium, copper, cobalt, nickel, dysprosium, rhenium, europium, terbium, holmium, neodymium or other comparable label, CT contrast agents, and ultrasound contrast agents. Additional diagnostic agents can include fluorescent labeling compounds such as fluorescein isothiocyanate, rhodamine, phycoerytherin, phycocyanin, allophycocyanin, o-phthaldehyde and fluorescamine, chemiluminescent compounds including luminol, isoluminol, an aromatic acridinium ester, an imidazole, an acridinium salt and an oxalate ester, and bioluminescent compounds including luciferin, luciferase and aequorin. Radionuclides can also be used as diagnostic and/or therapeutic agents, including for example, $^{90}$Y, $^{111}$In, $^{131}$I, $^{99m}$Tc, $^{186}$Re, $^{188}$Re, $^{177}$Lu, $^{67}$Cu, $^{212}$Bi, $^{213}$Bi, and $^{211}$At.

Therapeutic agents also include, for example, chemotherapeutic drugs such as vinca alkaloids, anthracyclines, epidophyllotoxins, taxanes, antimetabolites, alkylating agents, antibiotics, Cox-2 inhibitors, antimitotics, antiangiogenic and apoptotoic agents, particularly doxorubicin, methotrexate, taxol, CPT-11, camptothecins, and others from these and other classes of anticancer agents. Conjugation of camptothecins to Poly-(L-Glutamic Acid) has been described. See Singer et al., *Annals of N.Y. Acad. of Sci.*, 2000;922:136-500. Other useful therapeutic agents for the preparation of immunoconjugates and antibody fusion proteins include nitrogen mustards, alkyl sulfonates, nitrosoureas, triazenes, folic acid analogs, COX-2 inhibitors, pyrimidine analogs, purine analogs, platinum coordination complexes, hormones, and the like. Suitable therapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable therapeutic agents, such as experimental drugs, are known to those of skill in the art. Therapeutic agents may also include, without limitation, others drugs, prodrugs and/or toxins. The terms "drug," "prodrug," and "toxin" are defined throughout the specification. The terms "diagnostic agent" or "diagnosis" include, but are not limited to, detection agent, detection, or localization. The therapeutic and diagnostic agents may be associated with lipids capable of forming emulsions or liposomes or polymers capable of forming polymeric structures.

When the targetable construct includes a diagnostic agent, the bsAb is preferably administered prior to administration of the targetable construct (which includes the diagnostic agent). After sufficient time has passed for the bsAb to target to the diseased tissue, the targetable construct including the diagnostic agent (i.e., effector) is administered, so that imaging can be performed. Tumors can be detected in body cavities by means of directly or indirectly viewing various structures to which light of the appropriate wavelength is delivered and then collected, or even by special detectors, such as radiation probes or fluorescent detectors, and the like. Lesions at any body site can be viewed so long as nonionizing radiation can be delivered and recaptured from these structures. For example, PET which is a high resolution, non-invasive, imaging technique can be used with antibodies and targetable constructs for the visualization of human disease. In PET, 511 keV gamma photons produced during positron annihilation decay are detected. X-ray, computed tomography (CT), MRI and gamma imaging (e.g., Single Photon Emission Computed Tomography (SPECT)) may also be utilized through use of a diagnostic agent that functions with these modalities. As discussed earlier, the targetable construct may include radioactive diagnostic agents that emit 25-10, 000 keV gamma-, beta-, alpha- and auger-particles and/or positrons. Examples of such agents include, but are not limited to $^{18}$F, $^{45}$Ti, $^{52}$Fe, $^{62}$Cu, $^{64}$Cu, $^{67}$Cu, $^{67}$Ga, $^{68}$Ga, $^{86}$Y, $^{89}$Zr, $^{94m}$Tc, $^{94}$Tc, $^{99m}$Tc, $^{111}$In, $^{123}$I, $^{124}$I, $^{125}$I, $^{131}$I, $^{154-158}$Gd and $^{175}$Lu.

The present bsAbs or bsFabs can be used in a method of photodynamic therapy (PDT) as discussed in U.S. Pat. Nos. 6,096,289; 4,331,647; 4,818,709; 4,348,376; 4,361,544; 4,444,744; 5,851,527. In PDT, a photosensitizer, e.g., a hematoporphyrin derivative such as dihematoporphyrin ether, is administered to a subject. Anti-tumor activity is initiated by the use of light, e.g., 630 nm. Alternate photosensitizers can be utilized, including those useful at longer wavelengths, where skin is less photosensitized by the sun. Examples of such photosensitizers include, but are not limited to, benzoporphyrin monoacid ring A (BPD-MA), tin etiopurpurin (SnET2), sulfonated aluminum phthalocyanine (AlSPc) and lutetium texaphyrin (Lutex).

Additionally, in PDT, a diagnostic agent may be injected, for example, systemically, and laser-induced fluorescence can be used by endoscopes including wireless capsule-sized endoscopes or cameras to detect sites of cancer which have accreted the light-activated agent. For example, this has been applied to fluorescence bronchoscopic disclosure of early lung tumors. Doiron et al. *Chest* 76:32 (1979). In another example, the antibodies and antibody fragments can be used in single photon emission. For example, a Tc-99m-labeled diagnostic agent can be administered to a subject following administration of antibodies or antibody fragments. The subject is then scanned with a gamma camera which produces single-photon emission computed tomographic images and defines the lesion or tumor site.

Photoactive agents or dyes may be useful as therapeutic and/or diagnostic reagents. For example, therapeutically useful immunoconjugates can be obtained by conjugating photoactive agents or dyes to an antibody composite. Fluorescent and other chromogens, or dyes, such as porphyrins sensitive to visible light, have been used to detect and to treat lesions by directing the suitable light to the lesion. In therapy, this has been termed photoradiation, phototherapy, or photodynamic therapy (Jori et al. (eds.), *Photodynamic Therapy of Tumors and Other Diseases* (Libreria Progetto 1985); van den Bergh, *Chem. Britain* 22:430 (1986)). Moreover, monoclonal antibodies have been coupled with photoactivated dyes for achieving phototherapy. Mew et al., *J. Immunol.* 130:1473 (1983); idem., *Cancer Res.* 45:4380 (1985); Oseroff et al., *Proc. Natl. Acad. Sci. USA* 83:8744 (1986); idem., *Photochem. Photobiol.* 46:83 (1987); Hasan et al., *Prog. Clin. Biol. Res.* 288:471 (1989); Tatsuta et al., *Lasers Surg. Med.* 9:422 (1989); Pelegrin et al., *Cancer* 67:2529 (1991). However, these earlier studies did not include use of endoscopic therapy applications, especially with the use of antibody fragments or subfragments. Thus, the immunoconjugates may include photoactive agents or dyes. Endoscopic methods of detection and therapy are described in U.S. Pat. Nos. 4,932,412; 5,525, 338; 5,716,595; 5,736,119; 5,922,302; 6,096,289; and 6,387, 350, which are incorporated herein by reference in their entirety.

Radiopaque and contrast materials are used for enhancing X-rays and computed tomography, and include iodine compounds, barium compounds, gallium compounds, thallium compounds, etc. Specific compounds include barium, diatrizoate, ethiodized oil, gallium citrate, iocarmic acid, iocetamic acid, iodamide, iodipamide, iodoxamic acid, iogulamide, iohexol, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, and thallous chloride. Ultrasound contrast material may also by used including dextran and liposomes, particularly gas-filled liposomes.

Administering Immunomodulators

In one embodiment, an immunomodulator, such as a cytokine, may also be conjugated to the targetable construct by a linker or through other methods known by those skilled in the art. As used herein, the term "immunomodulator" includes cytokines, stem cell growth factors, lymphotoxins, such as tumor necrosis factor (TNF), and hematopoietic factors, such as interleukins (e.g., interleukin-1 (IL-1), IL-2, IL-3, IL-6, IL-10, IL-12, IL-18, and IL-21), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S1 factor," erythropoietin and thrombopoietin. Examples of suitable immunomodulator moieties include IL-2, IL-6, IL-10, IL-12, IL-18, IL-21, interferons, TNFs (e.g., TNF-α), and the like.

Administering Drugs and Prodrugs

Certain cytotoxic drugs that are useful for anticancer therapy are relatively insoluble in serum. In addition, some cytotoxic drugs are also quite toxic in an unconjugated form, and their toxicity is considerably reduced by conversion to prodrugs. Conversion of a poorly soluble drug to a more soluble conjugate, e.g., a glucuronide, an ester of a hydrophilic acid or an amide of a hydrophilic amine, will improve its solubility in the aqueous phase of serum and its ability to pass through venous, arterial or capillary cell walls and to reach the interstitial fluid bathing the tumor. Cleavage of the prodrug deposits the less soluble drug at the target site. Many examples of such prodrug-to-drug conversions are disclosed in U.S. Pat. No. 5,851,527, to Hansen.

Conversion of certain toxic substances such as aromatic or alicyclic alcohols, thiols, phenols and amines to glucuronides in the liver is the body's method of detoxifying them and making them more easily excreted in the urine. One type of antitumor drug that can be converted to such a substrate is epirubicin, a 4-epimer of doxorubicin (Adriamycin), which is an anthracycline glycoside and has been shown to be a substrate for human beta-D-glucuronidase. See, e.g., Arcamone Cancer Res. 45:5995 (1985). Other analogues with fewer polar groups are expected to be more lipophilic and show greater promise for such an approach. Other drugs or toxins with aromatic or alicyclic alcohol, thiol or amine groups are candidates for such conjugate formation. These drugs, or other prodrug forms thereof, are suitable candidates for the site-specific enhancement methods of the presently described compounds and methods.

The prodrug CPT-11 (irinotecan) is converted in vivo by carboxylesterase to the active metabolite SN-38. One application of the therapeutic method, therefore, is to use a bsAb targeted against a tumor and a hapten (e.g. di-DTPA) followed by injection of a di-DTPA-carboxylesterase conjugate. Once a suitable tumor-to-background localization ratio has been achieved, the CPT-11 is given and the tumor-localized carboxylesterase serves to convert CPT-11 to SN-38 at the tumor. Due to its poor solubility, the active SN-38 will remain in the vicinity of the tumor and, consequently, will exert an effect on adjacent tumor cells that are negative for the antigen being targeted. This is a further advantage of the method. Modified forms of carboxylesterases have been described and are within the scope of the disclosed compounds and methods. See, e.g., Potter et al., Cancer Res. 58:2646-2651 (1998) and Potter et al., Cancer Res. 58:3627-3632 (1998). In another embodiment, CPT-11 may be conjugated to a targetable construct that includes DTPA or a targeting molecule, which can further enhance localization and activation of CPT-11 to SN-38 at the tumor.

Etoposide is a widely used cancer drug that is detoxified to a major extent by formation of its glucuronide and is within the scope of the disclosed compounds and methods. See, e.g., Hande et al. Cancer Res. 48:1829-1834 (1988). Glucuronide conjugates can be prepared from cytotoxic drugs and can be injected as therapeutics for tumors pre-targeted with mAb-glucuronidase conjugates. See, e.g., Wang et al. Cancer Res. 52:4484-4491 (1992). Accordingly, such conjugates also can be used with the pre-targeting approach described here. Similarly, designed prodrugs based on derivatives of daunomycin and doxorubicin have been described for use with carboxylesterases and glucuronidases. See, e.g., Bakina et al. J. Med Chem. 40:4013-4018 (1997). Other examples of prodrug/enzyme pairs that can be used within the present methods include, but are not limited to, glucuronide prodrugs of hydroxy derivatives of phenol mustards and beta-glucuronidase; phenol mustards or CPT-11 and carboxypeptidase; methotrexate-substituted alpha-amino acids and carboxypeptidase A; penicillin or cephalosporin conjugates of drugs such as 6-mercaptopurine and doxorubicin and beta-lactamase; etoposide phosphate and alkaline phosphatase.

Co-administering Enzymes and Prodrugs

An enzyme capable of activating a prodrug at the target site or improving the efficacy of a normal therapeutic by controlling the body's detoxification pathways may be a component of the compound (e.g., conjugated to the spacer or hapten). An enzyme-hapten conjugate can be administered to the subject following administration of the pre-targeting bsAb and can be directed to the target site. After the enzyme is localized at the target site, a cytotoxic drug is injected, which is known to act at the target site, or a prodrug form thereof which is converted to the drug in situ by the pretargeted enzyme. After being administered, the drug may be detoxified to form an intermediate of lower toxicity, most commonly a glucuronide, using the mammal's ordinary detoxification processes. The detoxified intermediate, e.g., the glucuronide, is reconverted to its more toxic form by the pretargeted enzyme and thus has enhanced cytotoxicity at the target site. This results in a recycling of the drug. Similarly, an administered prodrug can be converted to an active drug through normal biological processes. The pretargeted enzyme improves the efficacy of the treatment by recycling the detoxified drug. This approach can be adopted for use with any enzyme-drug pair.

In an alternative embodiment, the enzyme-hapten conjugate can be mixed with the targeting bsAb prior to administration to the patient. After a sufficient time has passed for the enzyme-hapten-bsAb conjugate to localize to the target site and for unbound conjugate to clear from circulation, a prodrug is administered. As discussed above, the prodrug is then converted to the drug in situ by the pre-targeted enzyme.

In another embodiment, the pre-targeting bsAb is administered to the patient and allowed to localize to the target and substantially clear circulation. At an appropriate later time, a targetable construct comprising a prodrug, for example polyglutamic acid (SN-38-ester)$_{10}$, is given, thereby localizing the prodrug specifically at the tumor target. It is known that tumors have increased amounts of enzymes released from intracellular sources due to the high rate of lysis of cells within and around tumors. A practitioner can exploit this characteristic by appropriately selecting prodrugs capable of being activated by these enzymes. For example, carboxylesterase activates the prodrug poly-glutamic acid (SN-38-ester)$_{10}$ by cleaving the ester bond of the poly-glutamic acid (SN-38-ester)$_{10}$ releasing large concentrations of free SN-38 at the tumor. Alternatively, the appropriate enzyme also can be targeted to the tumor site.

After cleavage from the targetable construct, the drug is internalized by the tumor cells. Alternatively, the drug can be internalized as part of an intact complex by virtue of cross-linking at the target. The targetable construct can induce internalization of tumor-bound bsAb and thereby improve the efficacy of the treatment by causing higher levels of the drug to be internalized.

Compounds that Include Prodrugs Conjugated to Peptide Carriers

A variety of peptide carriers (e.g., as spacers) are well-suited for conjugation to prodrugs, including polyamino acids, such as polylysine, polyglutamic (E) and aspartic acids (D), including D-amino acid analogs of the same, and co-polymers, such as poly(Lys-Glu) {poly[KE]}, advantageously at a ratio from 1:10 to 10:1. Copolymers based on amino acid mixtures such as poly(Lys-Ala-Glu-Tyr (SEQ ID NO: 3) (KAEY; 5:6:2:1) can also be employed. Smaller polymeric carriers of defined molecular weight can be synthesized by solid-phase peptide synthesis techniques, readily producing polypeptides of from 2-50 residues in chain length. Another advantage of this type of reagent, other than precise structural definition, is the ability to place single or any desired number of chemical handles at certain points in the chain. These can be used later for attachment of recognition and therapeutic haptens at chosen levels of each moiety.

Poly(ethylene) glycol [PEG] has desirable in vivo properties for a bi-specific antibody prodrug approach. The desirable in vivo properties of PEG derivatives and the limited loading capacity due to their dimeric functionality has led to the preparation of PEG co-polymers having greater hapten-bearing capacity such as those described by Poiani et al. See, e.g., Poiani et al. *Bioconjugate Chem.*, 5:621-630, 1994. PEG can be used to conjugate any component of the compound, (such as drugs or prodrugs to lysine residues). For example, PEG derivatives can be activated at both ends to create bis (succinimidyl)carbonate derivatives and co-polymerized with multi-functional diamines such as lysine. The product of such co-polymerization, containing (-Lys(COOH)-PEG-Lys (COOH)-PEG-)$_n$ repeat units wherein the lysyl carboxyl group is not involved in the polymerization process, can be used for attachment of SN-38 residues. The SN-38 residues are reacted with the free carboxyl groups to produce SN-38 esters of the (-Lys-(COOH)-PEG-Lys(COOH)-PEG-)$_n$ chain.

Other synthetic polymers that can be used to conjugate haptens and/or prodrugs include N-(2-hydroxypropyl)methacrylamide (HMPA) copolymers, poly(styrene-co-maleic acid/anhydride (SMA), poly(divinylether maleic anhydride) (DIVEMA), polyethyleneimine, ethoxylated polyethyleneimine, starburst dendrimers and poly(N-vinylpyrrolidone) (PVP). As an example, DIVEMA polymer comprised of multiple anhydride units is reacted with a limited amount of SN-38 to produce a desired substitution ratio of drug on the polymer backbone. Remaining anhydride groups are opened under aqueous conditions to produce free carboxylate groups. A limited number of the free carboxylate groups are activated using standard water-soluble peptide coupling agents, (e.g., 1-ethyl-3-(3-dimethylaminopropyl)carbodiimide hydrochloride (EDC)), and coupled to a recognition moiety bearing a free amino group. An example of the latter is histamine, to which antibodies have been raised in the past.

The above exemplifications of polymer/drug conjugates embody the use of SN-38, which is the active metabolite of the prodrug CPT-11 (irinotecan). SN-38 has an aromatic hydroxyl group that was used in the above descriptions to produce aryl esters susceptible to esterase-type enzymes. Similarly the camptothecin analog topotecan, widely used in chemotherapy, has an available aromatic hydroxyl residue that can be used in a similar manner as described for SN-38, producing esterase-susceptible polymer-prodrugs. Water soluble derivatives of camptothecin are described in U.S. Pat. No. 4,943,579, incorporated herein by reference. Conjugation of camptothecins to poly-(L-glutamic acid) has been described. See Singer et al., *Annals of the N.Y. Acad. Sci.*, 922:136-150 (2000).

Doxorubicin also contains aromatic hydroxyl groups that can be coupled to carboxylate-containing polymeric carriers using acid-catalyzed reactions similar to those described for the camptothecin family. Similarly, doxorubicin analogs like daunomycin, epirubicin and idarubicin can be coupled in the same manner. Doxorubicin and other drugs with amino 'chemical handles' active enough for chemical coupling to polymeric carriers can be effectively coupled to carrier molecules via these free amino groups in a number of ways. Polymers bearing free carboxylate groups can be activated in situ (EDC) and the activated polymers mixed with doxorubicin to directly attach the drug to the side-chains of the polymer via amide bonds. Amino-containing drugs can also be coupled to amino-pendant polymers by mixing commercially available and cleavable cross-linking agents, such as ethylene glycobis(succinimidylsuccinate) (EGS, Pierce Chemical Co., Rockford, Ill.) or bis-[2-(succinimido-oxycarbonyloxy) ethyl]sulfone (BSOCOES, Molecular Biosciences, Huntsville, Ala.), to cross-link the two amines as two amides after reaction with the bis(succinimidyl) ester groups. This is advantageous as these groups remain susceptible to enzymatic cleavage. For example, (doxorubicin-EGS)$_n$-polylysine remains susceptible to enzymatic cleavage of the diester groups in the EGS linking chain by enzymes such as esterases. Doxorubicin also can be conjugated to a variety of peptides, for example, HyBnK(DTPA)YK(DTPA)-NH$_2$, using established procedures (HyBn=p-H$_2$NNHC$_6$H$_4$CO$_2$H). See Kaneko et al., *J. Bioconjugate Chem.*, 2: 133-141, 1991.

In one preferred embodiment, a therapeutic conjugate can be synthesized which includes camptothecin, a derivative of camptothecin, or doxorubicin coupled to a carrier comprising amine residues and a chelating agent, such as DTPA, to form a DTPA-peptide-doxorubicin conjugate, wherein the DTPA forms the recognition moiety for a pretargeted bsAb. Preferably, the carrier comprises a tyrosyl-lysine dipeptide, (e.g., Tyr-Lys(DTPA)-NH$_2$), and more preferably still it comprises Lys(DTPA)-Tyr-Lys(DTPA)-NH$_2$. Doxorubicin phenyl hydrazone conjugated to bis-DPTA containing peptides are particularly desirable in a therapeutic context.

Methotrexate also has an available amino group for coupling to activated carboxylate-containing polymers, in a similar manner to that described for doxorubicin. It also has two glutamyl carboxyl groups (alpha and gamma) that can be activated for coupling to amino-group containing polymers. The free carboxylate groups of methotrexate can be activated in situ (EDC) and the activated drug mixed with an amino-containing polymer to directly attach the drug to the side-chains of the polymer via amide bonds. Excess unreacted or cross-reacted drug is separated readily from the polymer-drug conjugate using size-exclusion or ion-exchange chromatography.

Maytansinoids and calicheamicins (such as esperamycin) contain mixed di- and tri-sulfide bonds that can be cleaved to generate species with a single thiol useful for chemical manipulation. The thiomaytensinoid or thioespera-mycin is first reacted with a cross-linking agent such as a maleimido-peptide that is susceptible to cleavage by peptidases. The C-terminus of the peptide is then activated and coupled to an amino-containing polymer such as polylysine.

Conjugation of Compounds to Lipids

The aforementioned compounds (e.g., targetable constructs and components thereof) and binding molecules (e.g., bsAbs) may be conjugated to: (1) lipids capable of delivering an effector (such as a drug); (2) molecules that can form a higher-ordered structure, (such as amphiphilic lipids or polymers), which are capable of delivering an effector (such as a drug); and/or (3) higher-ordered structures capable of delivering an effector, (such as a micelle, liposome, polymeric structure, or nanoparticle). The formation of liposomes, micelles, and emulsions is known in the art. (See, e.g., Wrobel et al., Biochimica et Biophysica Acta, 1235:296 (1995); Lundberg et al., J. Pharm. Pharmacol., 51:1099-1105 (1999); Lundberg et al., Int. J. Pharm., 205:101-108 (2000); Lundberg, J. Pharm. Sci., 83:72-75 (1994); Xu et al., Molec. Cancer Ther., 1:337-346 (2002); Torchilin et al., Proc. Nat'l. Acad. Sci., 100:6039-6044 (2003); U.S. Pat. Nos. 5,565,215; 6,379,698; and U.S. 2003/0082154). Nanoparticles or nanocapsules formed from polymers, silica, or metals, which are useful for drug delivery or imaging, have been described as well. (See, e.g., West et al., Applications of Nanotechnology to Biotechnology, 11:215-217 (2000); U.S. Pat. Nos. 5,620,708; 5,702,727; and 6,530,944).

Where the targeting molecule is conjugated to a lipid, preferably the lipid is capable of forming an emulsion or a higher-ordered structure such as a micelle or liposome. For example, the lipid may be amphiphilic (e.g., a phospholipid). To facilitate conjugation to a targetable construct, the lipid may contain one or more groups capable of reacting with the targetable construct such as nucleophilic carbons, (e.g., at a distal terminus). Polyethyleneglycol (PEG)-maleimide is a suitable lipid, whereby the maleimide can react with free thiol groups present on the targetable construct (e.g., on reduced cysteine residues). Maleimide groups may also be present on other carriers as described herein for conjugating targetable constructs or binding molecules. For example, nanoparticles may contain maleimide groups for conjugating a targetable construct. In addition to maleimide groups, other groups for conjugating targetable constructs or binding molecules may include vinylsulfones as described in U.S. Pat. No. 6,306,393. The lipid-conjugated, targetable constructs may form emulsions or liposomes that can incorporate effector molecules as described herein (e.g., hydrophobic drugs).

The conjugation of antibodies or binding molecules to lipids to form a targeted carrier for therapeutic or diagnostic agents has been described. (See, e.g., Bendas, Biodrugs, 15:215-224 (2001); Xu et al., Molec. Cancer Ther., 1:337-346 (2002); Torchilin et al., Proc. Nat'l. Acad. Sci., 100:6039-6044 (2003); Bally, et al., J. Liposome Res., 8:299-335 (1998); Lundberg, Int. J. Pharm., 109:73-81 (1994); Lundberg, J. Pharm. Pharmacol., 49:16-21 (1997); Lundberg, Anti-cancer Drug Design, 13:453-461 (1998)). See also U.S. Pat. No. 6,306,393; U.S. Ser. No. 10/350,096; U.S. Ser. No. 09/590,284; U.S. Ser. No. 60/138,284, filed Jun. 9, 1999; and U.S. Ser. No. 60/478,830, filed Jun. 17, 2003. All these references are incorporated herein by reference. The same chemistry used to conjugate binding molecules (i.e., targeting molecules) to lipids may be utilized to conjugate targetable constructs to lipids.

Preparation of Drug-Loaded Emulsions

Lipid-conjugated molecules can form emulsions or liposomes that include effectors such as drugs. The emulsions are composed of two major parts: (1) an oil core, (e.g., triglyceride); and (2) emulsifiers that stabilize the oil core, (e.g., phospholipids). Triolein (TO), egg phosphatidylcholine (EPC), dipalmitoyl phosphatidylethanolamine (DPPE), cholesterol (CHOL), 8-hydroxy-1,3,6-pyrenetrisulfonate (HPTS), polyoxyethylenesorbitan monooleate (sorbitan 80), methoxypolyethyleneglycol (PEG mean mol. wt 2000), oleoyl chloride, 3-(4,5-dimethylthiazol-2-yl)-2,5-diphenyltetrazolium bromide (MTT) and DL-dithiotreitol (DTT) are obtained from commercial sources such as Sigma Chemical Co. (St. Louis, Mo.). Poly(ethylene glycol)-maleimide-N-hydroxysuccinimidyl ester (MAL-PEG$_{2000}$-NHS) can be purchased from Shearwater Polymers Europe (Enschede, The Netherlands). [$^3$H]Cholesteryl oleoyl ether (COE) and [$^{14}$C]dipalmitoyl phosphatidylcholine are obtained from Amersham International plc (Amersham, UK). A PEG$_{2000}$ derivative of dipalmitoyl phosphatidylethanolamine (DPPE) with a maleimide group at the distal terminus of the PEG chain (DPPE-PEG-MAL) is synthesized by reacting 25 mol NHS-PEG-MAL with 23 mol DPPE and 50 mol triethylamine in chloroform for 6 h at 40° C. The product can be purified by preparative silica gel TLC.

Submicron lipid emulsions can be prepared as described in detail elsewhere. (See, Lundberg, J. Pharm. Sci., 83:72-75 (1994); Lundberg et al., Int. J. Pharm., 134:119-127 (1996); U.S. Ser. No. 60/478,830, filed Jun. 17, 2003; and U.S. Pat. No. 6,306,393). The drug-loaded emulsions include TO, EPC, polysorbate 80, DPPE-PEG$_{2000}$-MAL, and an effector (such as the drug FUdR-dO), at a ratio of 2:2:0.8:0.6:0.3 (w/w). The components are dispensed into vials from stock solutions and the solvent is evaporated to dryness under reduced pressure. Phosphate-buffered saline (PBS) is added and the mixture is heated to 50° C.; vortex-mixed for 30 s; and sonicated with a Branson probe sonicator for 2 min.

Drug loaded liposomes are composed of EPC, DPPE-PEG$_{2000}$-MAL, FUdR-dO 1:0.2:0.1 (w/w). A ratio of EPC, CHOL, DPPE-PEG$_{2000}$-MAL 2:0.5:0.4 is suitable. Dried lipid films are hydrated in 25 mM HEPES and 140 mM NaCl buffer (pH 7.4), (containing 35 mM HPTS when appropriate); and are subsequently subjected to five freezing-thawing cycles and sonication for 2 min with a Branson probe sonicator. The phospholipid concentration are quantitated by incorporating [$^{14}$C]DPPC.

Conjugation of Lipid Drug-Carriers to Targetable Constructs

Coupling of the aforementioned compounds (i.e., targetable constructs) or binding molecules to lipid drug-carriers can be performed by reacting the maleimide (MAL) groups at the distal PEG termini on the surface of a carrier and a free thiol group, or other suitable group, on a targetable construct or binding molecule. Where the targetable construct or binding molecule contains disulfide groups, the disulfide groups can be reduced before the coupling reaction with 50 mM dithiotreitol for 1 h at 4° C. in 0.2 M tris buffer (pH 6.5) to provide free thiol groups. The reduced molecule can be separated from excess dithiotreitol by use of Sephadex G-25 spin-columns, equilibrated with 50 mM sodium acetate buffered 0.9% saline (pH 5.3). The conjugation can be performed in HEPES-buffered saline (pH 7.4) for 16 h at room temperature under argon. Excess maleimide groups can be blocked with 2 mM 2-mercaptoethanol for 30 min, whereafter excess Ab and 2-mercaptoethanol can be removed on a Sepharose CL-4B column. The conjugated-liposomes can be collected near the void volume of the column, passed through a 0.22 μm sterile filter and stored at 4° C. The coupling efficiency can be estimated by use of a fluorescein labeled targetable construct or binding molecule.

Compounds for Combined Therapeutic and Diagnostic Methods

In still other embodiments, the bi-specific antibody-directed delivery of therapeutics or prodrug polymers to in vivo targets can be combined with bi-specific antibody delivery of radionuclides, such that combination chemotherapy and radioimmunotherapy is achieved. Each effector (e.g., nuclide and drug), may be conjugated to or non-covalently associated with the targetable construct and administered simultaneously, or the nuclide can be given as part of a first targetable construct and the drug given in a later step as part of a second targetable construct. In one embodiment, a peptide containing a single prodrug and a single nuclide is constructed. For example, the tripeptide Ac-Glu-Gly-Lys-$NH_2$ can be used as a carrier portion of a targetable construct, whereby SN-38 is attached to the gamma glutamyl carboxyl group as an aryl ester, while a chelate is attached to the epsilon amino group as an amide, to produce the complex Ac-Glu(SN-38)-Gly-Lys (chelate)-$NH_2$. The chelate can then be radiolabeled with various metals for imaging and therapy purposes including $^{111}$In, $^{90}$Y, $^{153}$Sm, $^{177}$Lu and $^{89}$Zr. Because the metal-chelate complex can represent the recognized hapten on the targetable construct, the antibody can be designed to recognize and bind a selected metal-chelate complex at a sufficiently high affinity. Generally, this affinity (log $K_a$) is between 6-11. Polymeric peptides can be given as readily as the more chemically defined lower MW reagent above, and are indeed preferred. Also, triply substituted polymers can be used, such as poly[Glu(Sn-38)$_{10}$-Lys(Y-90-chelate)$_n$(histamine-succinate)$_m$, where n and m are integers, such that the recognition agent is independent of the radioimmunotherapy agent. The prodrug can be activated by carboxylesterases present at the tumor site or by carboxylesterases targeted to the site using a second targetable construct.

Alternatively, a combination therapy can be achieved by administering the chemotherapy and radioimmunotherapy agents in separate steps. For example, a patient expressing CEA-tumors is first administered bsAb with at least one arm which specifically binds CEA and at least one other arm which specifically binds the targetable construct whose hapten is a complex (e.g., indium-DTPA or yttrium-DOTA). Later the patient is treated with a targetable construct comprising a conjugate (e.g., indium-DTPA-beta-glucuronidase or yttrium-DOTA-beta-glucuronidase. After sufficient time for bsAb and enzyme localization and clearance, a second targetable construct, comprising Ac-Cys(Campto-$COCH_2$)-Lys(indium-DTPA)-Tyr-Lys(indium-DTPA)-$NH_2$ or Ac-Glu (SN-38)-Gly-Lys(Y-90-DOTA)-$NH_2$, is given. The second targetable construct localizes to the tumor by virtue of bsAb at the tumor that are not already bound to a first targetable construct. First targetable constructs which are localized to the target site act on the Ac-Cys(CPT)-Lys(indium-DTPA)-Tyr-Lys(indium-DTPA)-$NH_2$ or Ac-Glu(SN-38)-Gly-Lys(Y-90-DOTA)-$NH_2$ to liberate CPT or SN-38. Localization of both the prodrug and its respective enzyme to the target site enhances the production of active drug by ensuring that the enzyme is not substrate limited. This embodiment constitutes a marked improvement of current prodrug methodologies currently practiced in the art.

Another advantage of administering the prodrug-polymer in a later step, after the nuclide has been delivered as part of a previously given targetable construct, is that the synergistic effects of radiation and drug therapy can be manipulated and, therefore, maximized. It is hypothesized that tumors become more 'leaky' after RAIT due to radiation damage. This can allow a polymer-prodrug to enter a tumor more completely and deeply. This results in improved chemotherapy.

Alternatively, the RAIT therapy agent can be attached to the bsAb rather than to the targetable construct. For example, an anti-CEA×anti-DTPA bsAb conjugated to Y-90-DOTA can be administered first to a patient with CEA-expressing tumors. In this instance, advantage is taken of the selectivity of certain anti-chelate mabs in that an anti-indium-DTPA antibody do not bind to a yttrium-DOTA chelate. After the Y-90-DOTA-anti-CEA×anti-indium-DTPA has maximized at the tumor and substantially cleared non-target tissue, a conjugate of indium-DTPA-glucuronidase is injected and localized specifically to the CEA tumor sites. The patient is then injected with a polymer-prodrug such as poly(Glu)(SN-38)$_{10}$. The latter is cleaved selectively at the tumor to active monomeric SN-38, successfully combining chemotherapy with the previously administered RAIT.

Antibodies

Bi-specific antibodies or antibody fragments can be used in the present method, with at least one binding site specific to an antigen at a target site and at least one other binding site specific to the enzyme component of the antibody-enzyme conjugate. Such an antibody can bind the enzyme prior to injection, thereby obviating the need to covalently conjugate the enzyme to the antibody. Alternatively, the antibody can be injected and localized at the target site and, after non-targeted antibody has substantially cleared from the circulatory system of the mammal, an enzyme can be injected in an amount and by a route which enables a sufficient amount of the enzyme to reach a localized antibody or antibody fragment and bind to it to form the antibody-enzyme conjugate in situ.

The methods disclosed herein also contemplate the use of multivalent target binding proteins which have at least three different target binding sites as described in patent application Ser. No. 60/220,782 filed Jul. 25, 2000. Multivalent target binding proteins have been made by cross-linking several Fab-like fragments via chemical linkers. See U.S. Pat. Nos. 5,262,524; 5,091,542 and Landsdorp et al., *Euro. J. Immunol.* 16: 679-83 (1986). Multivalent target binding proteins also have been made by covalently linking several single chain Fv molecules (scFv) to form a single polypeptide. See U.S. Pat. No. 5,892,020. A multivalent target binding protein which is basically an aggregate of scFv molecules has been disclosed in U.S. Pat. Nos. 6,025,165 and 5,837,242. A trivalent target binding protein comprising three scFv molecules has been described in Krott et al., *Protein Engineering* 10(4): 423-433 (1997).

Clearing Agents

A clearing agent can be used which is given between doses of the bsAb and the targetable construct. It has been discovered that a clearing agent of novel mechanistic action can be used with the methods described herein, namely a glycosylated anti-idiotypic Fab' fragment targeted against the disease targeting arm(s) of the bsAb. Anti-CEA (MN-14 Ab)×anti-peptide bsAb is given and allowed to accrete in disease targets to its maximum extent. To clear residual bsAb, an anti-idiotypic Ab to MN-14, termed Wl12, is given, preferably as a glycosylated Fab' fragment. The clearing agent binds to the bsAb in a monovalent manner, while its appended glycosyl residues direct the entire complex to the liver, where rapid metabolism takes place. Then the therapeutic or diagnostic agent which is associated with the targetable construct is given to the subject. The Wl12 Ab to the MN-14 arm of the bsAb has a high affinity and the clearance mechanism differs from other disclosed mechanisms (see Goodwin et al., ibid), as it does not involve cross-linking, because the Wl12-Fab' is a monovalent moiety. Clearing agents and uses thereof are described in U.S. Pat. Nos. 6,667,024; 6,468,530; 6,387,350; 6,096,289; 5,922,302; 5,736,119; 5,698,405; 5,698,178; 5,686,578; and U.S. Pat. No. 5,525,338; all of which are incorporated herein by reference in their entireties.

Kits

The compounds may be packaged as a kit suitable for use in treating or identifying diseased tissues in a patient by performing the methods disclosed herein. Minimally, the kit includes one or more of the compounds herein (e.g., as a targetable construct or targetable molecule). The kit can also include one or more binding molecules (e.g., antibodies or fragments thereof as targeting molecules) and/or one or more clearing agents. The kit can also include instruments which facilitate identifying or treating diseased tissue. Examples include, but are not limited to application devices, such as syringes. The kit can also include solutions required for identifying or treating diseased tissue. The kit can also include instructions and/or labels with instructions.

Methods for Raising Antibodies

Abs to peptide backbones and/or haptens are generated by well-known methods for Ab production. For example, an immunogen can be injected into an immunocompetent animal. The immunogen may include a peptide conjugated to KLH, (e.g., (peptide)$_n$-KLH, wherein KLH is keyhole limpet hemocyanin, and n=1-30, in complete Freund's adjuvant). The primary injection may be followed by two subsequent injections of the same immunogen suspended in incomplete Freund's adjuvant, and these injections may be followed by a subsequent i.v. boost of antigen (i.e., peptide). Three days after the i.v. boost of antigen, spleen cells are harvested and fused with Sp2/0-Ag14 myeloma cells. Culture supernatants of the resulting clones are then analyzed for anti-peptide reactivity using a direct-binding ELISA. Fine specificity mapping of the generated Abs can be analyzed by using peptide fragments of the original antigen/peptide. These fragments can be prepared readily using an automated peptide synthesizer. For Ab production, enzyme-deficient hybridomas are isolated to enable selection of fused cell lines. This technique also can be used to raise antibodies to one or more of the chelates comprising the linker, e.g., In(III)-DTPA chelates. Monoclonal mouse antibodies to an In(III)-di-DTPA are known (Barbet '395 supra).

The antibodies used in the present compounds and methods are specific to a variety of cell surface or intracellular tumor-associated antigens as marker substances. These markers may be substances produced by the tumor or may be substances which accumulate at a tumor site, on tumor cell surfaces or within tumor cells, whether in the cytoplasm, the nucleus or in various organelles or sub-cellular structures. Among such tumor-associated markers are those disclosed by Herberman, "Immunodiagnosis of Cancer", in Fleisher ed., "The Clinical Biochemistry of Cancer", page 347 (American Association of Clinical Chemists, 1979) and in U.S. Pat. Nos. 4,150,149; 4,361,544; and 4,444,744. See also U.S. Pat. No. 5,965,132, to Thorpe et al., U.S. Pat. No. 6,004,554, to Thorpe et al., U.S. Pat. No. 6,071,491, to Epstein et al., U.S. Pat. No. 6,017,514, to Epstein et al., U.S. Pat. No. 5,882,626, to Epstein et al., U.S. Pat. No. 5,019,368, to Epstein et al., and U.S. Pat. No. 6,342,221, to Thorpe et al., and U.S. patent application Ser. Nos. 09/337,756; 09/382,186; 09/823,746; and 10/150,654 all of which are incorporated herein by reference.

Tumor-associated markers have been categorized by Herberman, supra, in a number of categories including oncofetal antigens, placental antigens, oncogenic or tumor virus associated antigens, tissue associated antigens, organ associated antigens, ectopic hormones and normal antigens or variants thereof. Occasionally, a sub-unit of a tumor-associated marker is advantageously used to raise antibodies having higher tumor-specificity, e.g., the beta-subunit of human chorionic gonadotropin (HCG) or the gamma region of carcinoembryonic antigen (CEA), which stimulate the production of antibodies having a greatly reduced cross-reactivity to non-tumor substances as disclosed in U.S. Pat. Nos. 4,361, 644 and 4,444,744. Markers of tumor vasculature (e.g., VEGF), of tumor necrosis (Epstein patents), of membrane receptors (e.g., folate receptor, EGFR), of transmembrane antigens (e.g., PSMA), and of oncogene products can also serve as suitable tumor-associated targets for antibodies or antibody fragments. Markers of normal cell constituents which are expressed copiously on tumor cells, such as B-cell complex antigens (e.g., CD19, CD20, CD21, CD22, CD23, and HLA-DR on B-cell malignancies), as well as cytokines expressed by certain tumor cells (e.g., IL-2 receptor in T-cell malignancies) are also suitable targets for the antibodies and antibody fragments as used herein. Other well-known tumor associated antigens that can be targeted by the antibodies and antibody fragments used herein include, but are not limited to, CEA, CSAp, TAG-72, MUC-1, MUC-2, MUC-3, MUC-4, EGP-1, EGP-2, BrE3, PAM-4, KC-4, A3, KS-1, PSMA, PSA, tenascin, T101, S100, MAGE, HLA-DR, CD19, CD20, CD22, CD30, CD74, IFG, ILG-1, and IL-6.

Preferred bi-specific antibodies are those which incorporate the Fv of MAb Mu-9 and the Fv of MAb 734, the Fv of MAb MN-14 and the Fv of MAb 734, the Fv of MAb RS-7 and the Fv of MAb 734, the Fv of MAb Mu-9 and the Fv of MAb 679, the Fv of MAb RS-7 and the Fv of MAb 679, or the Fv of MAb MN-14 and the Fv of MAb 679, and their human, chimerized or humanized counterparts. The monoclonal antibody MN-14, as well as its chimerized and humanized counterparts, are disclosed in U.S. Pat. No. 5,874,540. Also preferred are bi-specific antibodies which incorporate one or more of the CDRs of Mu-9 or 679. Particularly suitable bi-specifica antibodies may include LL2×734, LL2×679, PAM4×734, PAM4×679, LL1×734, and LL1×679. The antibody can also be a fusion protein or a bi-specific antibody that incorporates a Class-III anti-CEA antibody and the Fv of 679. Class-III antibodies, including Class-III anti-CEA are discussed in detail in U.S. Pat. No. 4,818,709.

The present invention is further illustrated by, though in no way limited to, the following examples.

EXAMPLES

Example 1

Synthesis of 20-O-chloroacetyl Camptothecin

20-O-chloroacetyl camptothecin has been described. See U.S. Pat. No. 4,943,579. Camptothecin (1.0 gm) was dissolved in 40 mL of $CHCl_3$. Chloroacetic anhydride (1.2 eq), pyridine (1.0 eq) and DMAP (0.1 eq) was added to this mixture which was then refluxed for two hours. After no observable change in the reaction mixture, additional chloroacetic anhydride (1.2 eq) and pyridine (1.0 eq) was subsequently added and the mixture was refluxed for an additional 2 hrs. HPLC showed the reaction taking place. An additional amount of chloroacetic anhydride (2.1 eq) and pyridine (4.3 eq) was added and the reaction mixture was refluxed for another 2 hrs. HPLC showed the reaction to be complete. Mixture was worked up by washing with 65 mL of $H_2O$, then 0.1 N NaOH solution, then another 65 mL of $H_2O$. Organic layer was dried with $Na_2SO_4$ then filtered and finally removed under reduced pressure. Yellow precipitate formed. HPLC showed one product. ESMS results show $MH^+$: 425. Final yield after drying: 1.178 g ($2.772 \times 10^{-3}$ mol, 96.5%).

Example 2

Synthesis of IMP 274, Ac-Cys(Campto-$COCH_2$)-Lys (DTPA)-Tyr-Lys(DTPA)-$NH_2$

The IMP 274 peptide (see FIG. 1) was synthesized using a protocol similar to that described by Karacay et. al. *Bioconjugate Chem.* 11:842-854 (2000). IMP 222, (Ac-Cys-Lys (DTPA)-Tyr-Lys(DTPA)-$NH_2$) (38.1 mg) and 11.7 mg (1.0 eq) of 20-O-chloroacetyl camptothecin were each dissolved separately in 150 μL DMF. The two quantities were combined and stirred. Pyridine (100 μL) was added and the reaction vessel was purged with Argon and sealed with parafilm. Little change was noted by HPLC after 1.5 hrs. DIEA (50 mL) was then added to the reaction mixture. HPLC shows the reaction to have gone to completion after 2 hrs. The reaction mixture was purified using a prep column and fractions were sent for analysis by ESMS ($MH^+$: 1721). Four fractions show pure product with RT of ~7.1 minutes. Final yield: 22.2 mg ($1.290 \times 10^{-5}$ mol, 46.9%). Similarly, chemistry well known in the art can be used to synthesis derivatives of IMP 274 as shown in FIGS. 2-4.

Example 3

IMP 274 Labeling Kit

Labeling kits were made by dissolving citric acid (0.414 gm), HPCD (5.0074 gm), in 80 mL of DI $H_2O$. This mixture was then adjusted to pH 4.25 after which IMP 274 (0.0021 gm) was added. The volume was QS to 100 mL with DI $H_2O$ and 1 mL aliquots of this solution, filtered through a 0.22 μm filter, were added to lyophilization vials which were then frozen, lyophilized, and stoppered under vacuum.

Example 4

IMP 274 Peptide Labeling

A IMP 274 In-111 labeling kit was dissolved in 0.5 mL DI water. 110 μL of the solution was removed and placed in an acid washed Eppendorf tube. 1.8 mCi of the In-111 (preferably from Perkin Elmer) was added to the Eppendorf tube. The solution was allowed to incubate at room temperature for 20 min then 250 μL of the $1.0 \times 10^{-4}$ M In(III) solution (0.1 M NaOAc pH4.5) was added. The solution containing the cold indium was incubated at room temperature for 30 min. An aliquot, 140 μL, was removed and diluted with PBS or saline to 7.0 mL in a serum stoppered vial.

Example 5

Stability of $In_2$-IMP 274 Kits in an In-Vitro Testing Formulation Buffer

Lyophilized kits containing 1 mg of IMP 274 were prepared for in-vitro testing. The kits contain 2-hydroxypropyl-β-cyclodextrin (an excipient and solubilizer), a buffer, and cold Indium to form a complex with the DTPA moieties. To test stability after a repeated freeze-thaw cycle, the kits were thawed; aliquots were withdrawn and examined by reverse phase HPLC and size exclusion HPLC (without dilution or manipulation). The solutions were examined using a Waters 4.6×250 mm×Terra RP $C_{18}$ 5 μm column. The UV was monitored at 220 nm, The HPLC conditions were as follows: flow rate of 1 mL/min, linear gradient 100% A (0.1% TFA in water) to 100% B (90% $CH_3CN$, 10% water, 0.1% TFA) over 30 min. The peptide demonstrated stability in the formulation buffer. See FIGS. 7 and 8.

Example 6

IMP 274 Labeling and Stability Studies

IMP 274 was labeled with $^{111}$In. After being labeled, this protein was tested for stability in human and nude mouse serum over a period of 24 hrs. The studies show that the peptide does undergo stability changes in the presence of both human serum ($t_{1/2}$=4 hrs.) and mouse serum ($t_{1/2}$=18 hrs.). IMP 274 was also tested for binding with the humanized antibody, m734xhMN14. Studies were analyzed both on the reverse phase and the size exclusion HPLC systems.

Example 7

IMP 274 Labeling: Mouse and Human Labeling, Completed Separately $^{111}$InCl$_3$ (31 μL and 21 μL) was added respectively to 500 μL of DI $H_2O$. These quantities were added to the prepared vial of IMP 274 and allowed to sit for approximately 20 minutes. An additional 900 μL of cold In Acetate Buffer ($1.0 \times 10^{-4}$M, 0.5M NaOAc, pH 6.5) was added to each and were allowed to sit for an additional 45 minutes. The total volume for each vial was 1431 μL and 1421 μL with a molar quantity of $1.220 \times 10^8$ moles of IMP 274 yielding a concentration of $8.526 \times 10^{-6}$M for the mouse serum study and $8.586 \times 10^{-6}$M for the human serum study.

Example 8

IMP 274 Mouse and Human Serum Stability

One labeled peptide mixture, 50 μL, was combined with 450 μL fresh mouse and another with human serum. These were vortexed and placed under a constant temperature of 37° C. Samples were analyzed, at various time points, by HPLC for stability between 0 hr, and 23 hrs. The radiometric chromatograms show that the labeled peptide changed over time. (FIGS. 9 and 10). The dilutions of 50 μL of peptide in 500 μL of solution changed the concentration of both mixtures to $8.526 \times 10^{-7}$M for the mouse experiment and $8.586 \times 10^7$M human serum experiment.

Example 9

Addition of Antibody and Mouse Serum to IMP 274

$^{111}$In-IMP 274 (10 μL) was added to 3 μL of the antibody (antibody/peptide ratio of ~22:1) and 290 μL of 0.9% Saline. The mixture was vortexed and analyzed by size exclusion HPLC. (FIG. 11).

Example 10

Addition of Antibody and Human Serum to IMP 274

$^{111}$In-IMP 274 (16 μL) was added to 10 μL of antibody (antibody/peptide ratio of ~23:1) and 24 μL 0.9% Saline. The mixture was vortexed and analyzed by size exclusion HPLC. (FIG. 12).

Example 11

Synthesis of IMP 156
(Ac-Phe-Lys(DTPA)-Tyr-Lys-DTPA-NH$_2$)

The peptide on the resin was synthesized by reacting the resin with six equivalents of amino acid per coupling. The activating agents were diisopropylcarbodiimide and N-hydroxybenzotriazole. The couplings were run at room temperature overnight. The resin (2.109 g Ac-Phe-Lys(Aloc)-Tyr(But)-Lys(Aloc)NH-Sieber Amide Resin (~7×10$^{-4}$ mol)) was washed with 2×40 mL CH$_2$Cl$_2$. Tributyltin hydride, 5 mL was added to the resin. Piperidine, 2 mL was mixed with 1 mL of acetic acid, the mixture became hot and crystals formed. The crystals were dissolved in 40 mL CH$_2$Cl$_2$ and mixed with 0.729 g Pd[P(Ph)3]4. This solution was added to the resin mixture and mixed at room temperature for 1.5 hr. The cleavage solution was drained from the resin. The resin was then treated with a second one hour treatment with fresh Aloc cleavage reagents. The resin was washed with 40 mL portions of 3×CH$_2$Cl$_2$, 2×50 mL portions of 25% piperidine in DMF, 40 mL portions of NMP, IPA, NMP, IPA, IPA, and 4×NMP. DTPA tetra-t-butyl ester, 3.679 g (5.95×10$^{-3}$ mol) was dissolved in 20 mL NMP and mixed with 1 mL diisopropylcarbodiimide and 0.991 g N-hydroxybenzotriazole monohydrate. This solution was incubated at room temperature for 10 min and then added to the resin. The DTPA was reacted with the resin for 15 hr at room temperature. The resin was then washed with 40 mL portions of NMP, IPA, NMP, IPA, IPA, (the resin was ninhydrin negative) 4×NMP, 4×CH$_2$Cl$_2$ and then dried under a stream of nitrogen. The peptide was cleaved from the resin by a 3 hr treatment with a solution containing 14 mL TFA, 0.5 mL triisopropylsilane, and 0.5 mL anisole. The crude peptide was precipitated in ether, collected by centrifugation and dried in a vacuum oven at room temperature. The crude peptide was resuspended in TFA for 1.5 hr to finish cleaving the protecting groups from the peptide. The peptide was purified by reverse phase HPLC using 0.1% TFA buffers to afford 0.54 g of pure product after lyophilization (ESMS MH$^+$ 1377).

Example 12

Synthesis of IMP 222
(Ac-Cys-Lys(DTPA)-Tyr-Lys(DTPA)-NH$_2$

Fmoc-Lys(Aloc)-Tyr(But)-Lys(Aloc)-NH-Sieber Amide Resin (5.148 g, ~1.0×10$^{-2}$ mol) was added to a column, rinsed with 50 mL NMP, and then swelled by addition of a second 50 mL portion of NMP. N2 gas was added and bubbled through the resin for ~30 minutes (i.e., the column was bubbled). The solution was removed and 40 mL 25% Piperidine/NMP was added. The column was bubbled for 4 minutes and the solution was removed. A second 40 mL portion of 25% Piperidine/NMP was added. The column was bubbled for an additional 15 minutes and the solution was removed. The resin was rinsed with 50 mL portions of NMP, IPA, NMP, IPA, and then 4×NMP. Fmoc-Cys(Trt)OH (5.860 g), and N-hydroxybenzotriazole (1.535 g) were both dissolved in ~35 mL NMP. Diisopropylcarbodiimide (1.6 mL) was added. After the reagents were dissolved, the solution was added to the resin and the column was bubbled using N2 gas for ~18 hrs. The solution was removed and the resin was rinsed with 50 mL portions of NMP, IPA, NMP, IPA, and then 4×NMP. A 25% Piperidine/NMP solution was added. The column was again bubbled with N2 gas for 4 minutes and the solution was removed. This was repeated again for 15 minutes with the 25% Piperidine/NMP solution and the solution was removed. The resin was rinsed with 50 mL portions of NMP, IPA, NMP, IPA, and then 4×NMP. Acetic Anhydride (4.8 mL) was added to 40 mL of NMP and then Diisopropylethylamine (8.9 mL) was added. This solution was added to the resin and the column was bubbled with N2 gas for ~2 hrs. The resin was rinsed with 50 mL portions of NMP, IPA, NMP, IPA, and then 4×NMP. The resin was then rinsed with 2×50 mL CH$_2$Cl$_2$. Tributyltin hydride (5 mL) was added to the resin. A previously mixed solution of Tetrakis(Triphenylphosphine)Palladium(0) (1.095 g), Glacial acetic acid (2 mL), Piperidine (4 mL) and ~55 mL of CH$_2$Cl$_2$ was also added to the resin. The column was bubbled with N2 gas for ~2 hrs. and the solution was removed. The procedure was repeated with Tributyltin hydride (5 mL), Tetrakis(Triphenylphosphine)Palladium(0) (1.001 g), Glacial acetic acid (2 mL), Piperidine (4 mL) and ~55 mL of CH$_2$Cl$_2$. The column was bubbled with N2 gas for ~1 hr. and the solution was removed. The resin was rinsed with 50 mL portions of NMP, IPA, NMP, IPA, and then 4×NMP. Tetra t-butyl ester DTPA (7.087 g) was dissolved in ~25 mL NMP. To this solution was added N-hydroxybenzotriazole (1.715 g) and diisopropylcarbodiimide (1.8 mL). The column was bubbled with N2 gas for ~18 hrs and the solution was removed. The resin was rinsed with 50 mL portions of NMP, IPA, NMP, IPA, and then 4×NMP. This was followed by 3×50 mL rinses of CH$_2$Cl$_2$. The resin was dried by slow purge of N$_2$ gas for ~30 minutes. The peptide was cleaved from the resin and deprotected by addition of premixed solution consisting of 60 mL Trifluoroacetic acid, 2 mL Anisole, and 2 mL Triisopropylsilane. The column was bubbled with N$_2$ gas for ~2 hrs, the solution was removed, and the supernatant was collected. The resin was rinsed with an additional amount of 25 mL Trifluoroacetic acid, which was collected as well. The supernatant was poured into 50 mL polyethylene centrifuge tubes (~10 mL per tube). The peptide was precipitated out of solution by addition of 40 mL Diethyl ether to each followed by vortexing and centrifuging for approximately 5 minutes. The supernatant was decanted and the procedure was repeated twice more. The remaining crude peptide was dried under vacuum overnight. The crude peptide was redissolved with approximately 10 mL trifluoroacetic acid and monitored by HPLC due to incomplete cleavage. The precipitation procedure using diethyl ether was repeated after ~2 hrs. All the crude dried peptide was combined and dissolved in 8 mL of deionized water. The peptide solution was loaded onto a Waters RCM® Preperative Column and, using mobile phases A (0.1% TFA in DI H$_2$O) and B (0.1% TFA in 90% Acetonitrile/10% DI H$_2$O), purified using a gradient of 100%/0% to 70%/30% over 80 minutes at 65 mL min$^{-1}$. Fractions #7, 8, 9, & 10 contained pure material by analytical HPLC. The fractions were frozen and lyophilized to yield a total of 521.4 mg of pure material. Samples were sent for ESMS analysis which showed MH$^+$: 1333 and [M−H]: 1331 for each fraction.

Example 13

Synthesis of Bromoacetyl Doxorubicin

Doxorubicin hydrochloride, 0.9993 g (1.72×10$^{-3}$ mol) was dissolved in 10 mL DMF and mixed with 0.5 mL pyridine. The solution was cooled in an ice bath. Bromo acetyl bromide, 160 µL (1.84×10$^{-3}$ mol), was added to the reaction mixture. Diisopropylethyl amine, 0.6 mL was added after 3.5 hr. HPLC analysis showed mostly starting material so the starting material was precipitated by mixing with ether. The precipitate was washed with 2×30 mL portions of ether and dried in a vacuum oven at room temperature. The doxorubicin was redissolved in 10 mL DMF. Diisopropylethylamine, 1 mL, was added followed by the addition of 250 μL ($2.87 \times 10^{-3}$ mol) of additional bromo acetyl bromide. The solution was mixed for 17 min and precipitated with 60 mL ether. The red solid precipitate was washed with three additional 60 mL portions of ether. The red solid precipitate was resuspended in 10 mL CH$_3$CN and precipitated by pouring into 50 mL of ether to obtain a red powder. The red powder was collected by centrifugation and was again washed with 3×60 mL portions of ether. The crude product was then purified by flash chromatography by dissolving the crude product in CHCl$_3$ and placing on flash silica ¾ full in a 150 mL sintered glass funnel. The silica was eluted with 200 mL portions of ether, chloroform, 4×95:5 chloroform/methanol and 2×90:10 chloroform/methanol. The product was in the second (0.1390 g) and third (0.2816 g) 95:5 chloroform/methanol fractions.

Example 14

Synthesis of IMP 225

The bromoacetyl doxorubicin (0.0714 g, $1.08 \times 10^{-4}$ mol) was mixed with 0.1333 g ($1.00 \times 10^{-4}$ mol) IMP 222 and dissolved in 1.0 mL DMF. Potassium bicarbonate, 0.4544 g was suspended in 1 mL H$_2$O and then added to the DMF solution, which warmed slightly. The reaction mixture was incubated at room temperature overnight. The reaction mixture was poured into 30 mL of ether in a 50 mL centrifuge tube. The contents of the tube were mixed and the ether layer was decanted. The ether wash was repeated with a second 30 mL portion of ether. The solution was then acidified with 1 M HCl and purified in two portions by HPLC on a Waters 19×300 mm Prep Nova-Pak HRC18 6 μm 60 Å column. The gradient started at 100% 0.1% TFA in water (Buffer A) flowing at 25 mL/min and, using a linear gradient, it went to 50:50 Buffer A:B (buffer B being 90% CH$_3$CN 0.1% TFA, 10% H$_2$O) over 80 min. The fractions containing the desired product were collected and lyophilized to afford 0.0895 g (47% yield) of the desired product (ESMS MH$^+$ 1916). See FIG. 5 for chemical structure of IMP 225.

Example 15

Synthesis of IMP 294 (In$_2$-labeled IMP 225)

A 0.1 M citric acid buffer was prepared by dissolving 0.386 g of citric acid in 15 mL H$_2$O. The buffer solution was adjusted to pH 3.60 by the addition of 1 M NaOH and the solution was diluted to 20 mL. The peptide, 0.293 g ($1.53 \times 10^{-5}$ mol, 100 mol %) was mixed with 0.0128 g ($5.79 \times 10^{-5}$ mol, 378 mol %) InCl$_3$ and dissolved in 5 mL of the citrate buffer. The reaction solution was incubated at room temperature overnight and then purified by HPLC on a Waters 19×300 mm Prep Nova-Pak HRC18 6 μm 60 Å column. The gradient started at 90% Buffer A (defined above) and 10% Buffer B (defined above) flowing at 25 mL/min and, using a linear gradient, it went to 60:40 Buffer A:B over 80 min. The fractions containing the desired product were collected and lyophilized to afford 0.0160 g (49% yield) of the desired product (ESMS MH-2318).

Example 16

Synthesis of IMP 295 (In$_2$-labeled IMP 156)

The peptide, IMP 156, 0.1299 g ($9.43 \times 10^{-5}$ mol, 100 mol %) was mixed with 0.0740 g ($3.34 \times 10^{-4}$ mol, 355 mol %) and dissolved in 5 mL of the 0.1 M, pH 3.6 citrate buffer. The reaction solution was incubated at room temperature for ~4 hr then purified by HPLC on a Waters 19×300 mm Prep Nova-Pak HRC18 6 μm 60 Å column. The gradient started at 100% Buffer A (defined above) flowing at 25 mL/min and, using a linear gradient, it went to 50:50 Buffer A:B over 80 min. The fractions containing the desired product were collected and lyophilized to afford 0.1095 g (73% yield) of the desired product (ESMS MH$^{31}$ 1598).

Example 17

Stability of IMP 294 and IMP 295 in PBS at 25° C.

A phosphate buffered saline (PBS) solution was prepared by mixing 2.535 g Na$_2$HPO$_4$, 0.450 g NaH$_2$PO$_4$.H$_2$O, 4.391 g NaCl and diluting to 500 mL with H$_2$O. A stock solution of IMP 294 was prepared by dissolving 0.0011 g of the peptide in 5.00 mL of PBS. A 2.0 mL aliquot of the stock solution was removed and mixed with 4.9 mL of PBS to provide a $3 \times 10^{-5}$ M solution of the IMP 294 (In$_2$ IMP 225) in PBS. A stock solution of IMP 295 was prepared by dissolving 0.0011 g of the peptide in 5.00 mL of PBS. A 2.0 mL aliquot of the stock solution was removed and mixed with 7.2 mL of PBS to provide a $3 \times 10^{-5}$ M solution of the IMP 295 (In$_2$ IMP 156) in PBS. The samples were incubated in the auto-injector of the Waters Alliance HPLC at 25° C. The samples were analyzed by reverse phase HPLC using a Waters Xterra™ RP$_{18}$ 5 μm 4.6×250 mm column, part number W10891 R 015, which was heated at 25° C. The flow rate for the column was 1 mL/min and the eluent was monitored at 220 nm with a PDA detector. A linear gradient was used starting at 100% Buffer A going to 100% Buffer B over 30 min. Injections, (100 μL) were made daily for one week. See FIGS. 13A and B.

Example 18

Synthesis of IMP 224

An amount of 0.0596 g of the phenyl hydrazine containing peptide IMP 221 (H$_2$N—NH—C$_6$H$_4$—CO-Lys(DTPA)-Tyr-Lys(DTPA)-NH$_2$ MH+1322, made by Fmoc SPPS) was mixed with 0.0245 g of Doxorubicin hydrochloride in 3 mL of DMF. The reaction solution was allowed to react at room temperature in the dark. After 4 hours an additional 0.0263 g of IMP 221 was added and the reaction continued overnight. The entire reaction mixture was then purified by HPLC on a Waters Nova-Pak (3-40×100 mm segments, 6 μm, 60 Å) prep column eluting with a gradient of 80:20 to 60:40 Buffer A:B over 40 min (Buffer A=0.3% NH$_4$OAc, Buffer B=0.3% NH$_4$OAc in 90% CH$_3$CN). The fractions containing product were combined and lyophilized to afford 0.0453 g of the desired product, which was confirmed by ESMS MH$^+$1847. See FIG. 6 for chemical structure of IMP 224.

Example 19

IMP 224 Kit Formulation

The peptide of Example 14 was formulated into kits for In-111 labeling. A solution was prepared which contained 5.014 g 2-hydroxypropyl-α-cyclodextrin, and 0.598 g citric acid in 85 mL. The solution was adjusted to pH 4.20 by the addition of 1 M NaOH and diluted with water to 100 mL. An amount of 0.0010 g of the peptide IMP 224 was dissolved in 100 mL of the buffer, and 1 mL aliquots were sterile filtered through a 0.22 μm Millex GV filter into 2 mL lyophilization vials which were immediately frozen and lyophilized.

Example 20

In-111 Labeling of IMP 224 Kits

The In-111 was dissolved in 0.5 mL water and injected into the lyophilized kit. The kit solution was incubated at room temperature for 10 min then 0.5 mL of a pH 7.2 buffer which contained 0.5 M NaOAc and $2.56\times10^{-5}$ M cold indium was added.

Example 21

In-Vitro Stability of IMP 224 Kits

An IMP 224 kit was labeled as described with 2.52 mCi of In-111. Aliquots (0.15 mL, 370 µCi) were withdrawn and mixed with 0.9 mL 0.5 M citrate buffer pH 4.0, 0.9 mL 0.5 M citrate buffer pH 5.0, and 0.9 mL 0.5 M phosphate buffer pH 7.5. The stability of the labeled peptide was followed by reverse phase HPLC. HPLC Conditions: Waters Radial-Pak C-18 Nova-Pak 8×100 mm, Flow Rate 3 mL/min, Gradient: 100% A=0.3% NH$_4$OAc to 100% B=90% CH$_3$CN, 0.3% NH$_4$OAc over 10 min. The stability results are shown in Table 1.

TABLE 1

In-Vitro Stability of In/In-111 IMP 224

| Kit | | pH 4.0 | | pH 5.0 | | pH 7.5 | |
| --- | --- | --- | --- | --- | --- | --- | --- |
| Time | % Intact Peptide | Time | % Intact Peptide | Time | % Intact Peptide | Time | % Intact Peptide |
| 0 | 100 | 24 min | 100 | 0 | 100 | 24 min | 100 |
| | | 2 hr | 100* | | | 2 hr | 100* |
| 21 hr | 89 | 19 hr | 25 | 21 hr | 89 | 19 hr | 25 |

*Some peptide decomposed but was not included in the calculation of the areas of the peaks

Example 22

Biodistribution of In-111-Labeled IMP 274 and 1-125-Labeled hRS-7×MAb 734 in CALU-3 Tumor Bearing Nude Mice and Pretargeting with hRS-7×MAb 734

Seventy nude mice were implanted with CALU-3 cells. These mice were used to look at the possibility of doing pretargeting with EGP-1 expressing tumors. Tumor binding and in-vivo clearance of the bispecific antibody 1-125 hRS-7×734 was assayed using time points of 2, 4, 24 and 48 hr. In addition, we performed a pretargeting experiment with I-125 hRS-7×734. For the pretargeting experiment the peptide In-111/In IMP 274 was injected at 16 and 24 hr after the injection of the bispecific antibody hRS-7×734. The animals in the pretargeting study were sacrificed at 3 and 24 hr after the injection of the peptide. A third group of animals received only the In-11/In IMP 274 peptide. These animals were sacrificed at 1, 3, 6 and 24 hr post injection of the peptide. Typically, five mice were used for each time point. The following tissues were weighed and counted: Tumor, Liver, Spleen, Kidney, Lung, Blood, Stomach, Small Intestine, Large Intestine, Heart and Urine.

Antibody Clearing Group: At least 35 animals were injected with 100 µL of a solution containing the bispecific antibody I-125 hRS-7×734 (5 µCi, 15 µg, $1.5\times10^{-10}$ mol).

The 20 animals in the antibody clearance group were split into five groups of five animals each and sacrificed at 2, 4, 24 and 48 hr postinjection.

Pretargeting Group: The 30 animals in the pretargeting group were split into six groups of approximately five animals each. Approximately 24 hours later, the I-125 labeled bispecific antibody was injected into another 10 animals, and the peptide 100 µL (10 µCi, $1.5\times10^{-11}$ mol) was injected into those 10 animals at 4 hr postinjection of the antibody. The animals were sacrificed at 3 and 24 hr after the injection of the peptide. Approximately 24 hours later, the peptide, 100 µL (10 µCi, $1.5\times10^{-11}$ mol), was injected into 10 animals at 24 hr postinjection of the antibody. The animals were sacrificed at 3 and 24 hr after the injection of the peptide. Approximately 48 hours later, 10 animals were injected with 100 µL of the peptide. Five animals per time point were sacrificed at 3 hr and 24 hr post injection of the peptide.

Peptide Alone Group: Approximately 24 hours after the start of the study, the peptide 100 µL (10 µCi, $1.5\times10^{-11}$ mol) was injected into 15 animals. The animals were split into three groups and sacrificed at 1, 3, 6 and 24 hr post injection of the peptide. The results of the study are summarized in Tables 2-9.

TABLE 2

In-111/IMP 274 Biodistribution in CALU-3 Tumor Bearing Nude Mice, % ID/g

| Tissue | 1 Hr | 3 Hr | 6 Hr | 24 Hr |
| --- | --- | --- | --- | --- |
| Tumor | 0.32 ± 0.11 | 0.14 ± 0.02 | 0.11 ± 0.02 | 0.13 ± 0.02 |
| Liver | 0.11 ± 0.02 | 0.10 ± 0.01 | 0.10 ± 0.02 | 0.10 ± 0.02 |
| Spleen | 0.11 ± 0.02 | 0.10 ± 0.01 | 0.09 ± 0.01 | 0.09 ± 0.02 |
| Kidney | 2.24 ± 0.66 | 1.93 ± 0.18 | 1.59 ± 0.18 | 1.05 ± 0.18 |
| Lung | 0.22 ± 0.04 | 0.12 ± 0.05 | 0.11 ± 0.04 | 0.06 ± 0.01 |
| Blood | 0.25 ± 0.06 | 0.12 ± 0.02 | 0.09 ± 0.02 | 0.03 ± 0.00 |
| Stomach | 0.09 ± 0.05 | 0.12 ± 0.02 | 0.03 ± 0.01 | 0.03 ± 0.01 |
| Sm. Int. | 0.25 ± 0.13 | 0.21 ± 0.10 | 0.06 ± 0.01 | 0.08 ± 0.02 |
| Large Int. | 0.13 ± 0.14 | 0.62 ± 0.38 | 0.22 ± 0.05 | 0.06 ± 0.01 |
| Heart | 0.10 ± 0.02 | 0.07 ± 0.01 | 0.06 ± 0.01 | 0.04 ± 0.01 |
| Urine | 269 ± 366 | 7.28 ± 10.9 | 0.82 ± 0.56 | 0.20 ± 0.10 |

TABLE 3

I-125-labeled hRS-7 × 734 Biodistribution in CALU-3 Tumor Bearing Nude Mice, % ID/g

| Tissue | 2 Hr | 4 Hr | 24 Hr | 48 Hr |
| --- | --- | --- | --- | --- |
| Tumor | 2.80 ± 0.81 | 3.98 ± 1.71 | 5.10 ± 2.20 | 1.84 ± 0.40 |
| Liver | 2.80 ± 0.70 | 2.94 ± 1.08 | 0.67 ± 0.14 | 0.19 ± 0.01 |
| Spleen | 2.37 ± 1.08 | 2.95 ± 0.86 | 0.63 ± 0.20 | 0.15 ± 0.05 |
| Kidney | 5.73 ± 1.36 | 5.37 ± 1.42 | 0.70 ± 0.16 | 0.13 ± 0.01 |
| Lung | 3.46 ± 1.73 | 2.81 ± 1.20 | 0.71 ± 0.19 | 0.09 ± 0.02 |
| Blood | 13.2 ± 2.49 | 9.69 ± 2.28 | 1.53 ± 0.22 | 0.14 ± 0.02 |
| Stomach | 3.41 ± 0.58 | 6.59 ± 2.36 | 1.83 ± 1.21 | 0.17 ± 0.05 |
| Sm. Int. | 1.61 ± 0.40 | 1.47 ± 0.45 | 0.39 ± 0.11 | 0.05 ± 0.00 |
| Large Int. | 0.82 ± 0.22 | 1.02 ± 0.28 | 0.36 ± 0.11 | 0.06 ± 0.01 |
| Heart | 2.74 ± 0.99 | 2.92 ± 0.94 | 0.52 ± 0.07 | 0.05 ± 0.01 |
| Urine | 4.05 ± 1.96 | 3.13 ± 2.36 | 4.05 ± 3.54 | 1.40 ± 0.72 |

TABLE 4

In-111-labeled IMP 274 Biodistribution in CALU-3 Tumor Bearing Nude Mice Pretargeted with hRS-7 × m73. Peptide Injected 4, 24, & 48 hr Post bsAb Injection, 10:1 bsAb/peptide Ratio. % ID/g Determined 3 Hr Post Injection of the Peptide.

| Tissue | 4 hr Post bsAb | 24 hr Post bsAb | 48 hr Post bsAb |
|---|---|---|---|
| Tumor | 2.88 ± 1.54 | 10.3 ± 1.89 | 4.58 ± 1.02 |
| Liver | 3.73 ± 1.42 | 0.92 ± 0.26 | 0.14 ± 0.04 |
| Spleen | 2.95 ± 0.71 | 0.82 ± 0.30 | 0.14 ± 0.02 |
| Kidney | 5.15 ± 0.53 | 2.61 ± 0.25 | 1.32 ± 0.50 |
| Lungs | 2.63 ± 0.67 | 0.79 ± 0.14 | 0.17 ± 0.05 |
| Blood | 11.4 ± 3.60 | 2.06 ± 0.59 | 0.23 ± 0.03 |
| Stomach | 1.22 ± 0.23 | 0.42 ± 0.21 | 0.10 ± 0.11 |
| Sm Int | 2.31 ± 0.46 | 0.52 ± 0.25 | 0.11 ± 0.05 |
| Large Int | 2.54 ± 0.96 | 0.56 ± 0.19 | 0.86 ± 0.48 |
| Heart | 2.54 ± 0.71 | 0.67 ± 0.16 | 0.09 ± 0.01 |
| Urine | 39.8 ± 33.5 | 22.4 ± 25.0 | 7.55 ± 4.89 |

TABLE 5

In-111-labeled IMP 274 Biodistribution in CALU-3 Tumor Bearing Nude Mice Pretargeted with hRS-7 × m734. Peptide injected 4, 24 & 48 hr Post bsAb Injection, 10:1 bsAb/peptide Ratio. Tumor/nontumor (T/NT) Ratios Determined 3 Hr Post Injection of the Peptide.

| Tissue | 4 hr Post bsAb | 24 hr Post bsAb | 48 hr Post bsAb |
|---|---|---|---|
| Tumor | — | — | — |
| Liver | 0.76 ± 0.43 | 11.8 ± 4.68 | 34.4 ± 8.97 |
| Spleen | 0.92 ± 0.44 | 14.0 ± 6.58 | 33.7 ± 3.78 |
| Kidney | 0.54 ± 0.28 | 3.88 ± 0.85 | 3.86 ± 1.36 |
| Lungs | 1.07 ± 0.59 | 13.1 ± 3.55 | 28.9 ± 6.19 |
| Blood | 0.24 ± 0.12 | 5.29 ± 2.09 | 19.5 ± 3.46 |
| Stomach | 2.30 ± 1.21 | 33.2 ± 24.7 | 95.4 ± 73.9 |
| Sm Int | 1.29 ± 0.76 | 25.4 ± 16.9 | 47.5 ± 21.1 |
| Large Int | 1.40 ± 1.09 | 19.9 ± 7.80 | 8.23 ± 6.86 |
| Heart | 1.08 ± 0.53 | 16.0 ± 5.76 | 51.4 ± 9.73 |
| Urine | 0.20 ± 0.22 | 10.6 ± 22.0 | 2.06 ± 3.32 |

TABLE 6

In-111-labeled IMP 274 Biodistribution in CALU-3 Tumor Bearing Nude Mice Pretargeted with hRS-7 × m73. Peptide Injected 4, 24, & 48 hr Post bsAb Injection, 10:1 bsAb/peptide Ratio. % ID/g Determined 24 Hr Post Injection of the Peptide.

| Tissue | 4 hr Post bsAb | 24 hr Post bsAb | 48 hr Post bsAb |
|---|---|---|---|
| Tumor | 5.26 ± 2.76 | 9.66 ± 0.50 | 4.79 ± 1.11 |
| Liver | 4.95 ± 2.51 | 0.90 ± 0.20 | 0.17 ± 0.03 |
| Spleen | 4.95 ± 2.62 | 1.19 ± 0.32 | 0.16 ± 0.04 |
| Kidney | 4.75 ± 1.55 | 2.22 ± 0.68 | 1.21 ± 0.29 |
| Lungs | 0.93 ± 0.49 | 0.36 ± 0.09 | 0.11 ± 0.04 |
| Blood | 0.60 ± 0.22 | 0.31 ± 0.06 | 0.07 ± 0.02 |
| Stomach | 0.39 ± 0.24 | 0.09 ± 0.03 | 0.05 ± 0.05 |
| Sm Int | 0.64 ± 0.22 | 0.21 ± 0.04 | 0.08 ± 0.01 |
| Large Int | 0.76 ± 0.34 | 0.18 ± 0.02 | 0.09 ± 0.04 |
| Heart | 2.03 ± 0.99 | 0.42 ± 0.11 | 0.07 ± 0.01 |
| Urine | 5.68 ± 3.42 | 1.00 ± 1.02 | 0.56 ± 0.53 |

TABLE 7

In-111-labeled IMP 274 Biodistribution in CALU-3 Tumor Bearing Nude Mice Pretargeted with hRS-7 × m734. Peptide injected 4, 24 & 48 hr Post bsAb Injection, 10:1 bsAb/peptide Ratio. T/NT Ratios Determined 24 Hr Post Injection of the Peptide.

| Tissue | 4 hr Post bsAb | 24 hr Post bsAb | 48 hr Post bsAb |
|---|---|---|---|
| Tumor | — | — | — |
| Liver | 1.06 ± 0.14 | 11.2 ± 2.49 | 29.2 ± 12.5 |
| Spleen | 1.10 ± 0.19 | 8.54 ± 2.18 | 30.0 ± 7.89 |
| Kidney | 1.07 ± 0.31 | 4.72 ± 1.63 | 4.07 ± 1.01 |
| Lungs | 5.90 ± 1.47 | 27.9 ± 6.69 | 47.5 ± 12.4 |
| Blood | 8.53 ± 1.80 | 32.5 ± 6.72 | 70.6 ± 24.7 |
| Stomach | 15.4 ± 5.88 | 117 ± 47.7 | 137 ± 77.1 |
| Sm Int | 7.90 ± 1.89 | 47.3 ± 9.61 | 59.4 ± 16.1 |
| Large Int | 6.81 ± 0.99 | 55.4 ± 8.46 | 64.7 ± 28.2 |
| Heart | 2.57 ± 0.26 | 24.3 ± 6.19 | 74.1 ± 19.9 |
| Urine | 0.99 ± 0.17 | 25.9 ± 28.2 | 120 ± 216 |

TABLE 8

In-111-labeled IMP 274 Biodistribution in CALU-3 Tumor Bearing Nude Mice Pretargeted with 250 mg hRS-7 × m734. Peptide Injected 48 hr Post bsAb Injection, 136:1 bsAb/peptide Ratio. % ID/g and T/NT Ratios Determined 3 & 24 hr Post Injection of the Peptide.

| Tissue | 3 hr % ID/g | 3 hr T/NT | 24 hr % ID/g | 48 hr T/NT |
|---|---|---|---|---|
| Tumor | 10.9 ± 3.14 | — | 8.48 ± 2.77 | — |
| Liver | 3.18 ± 1.21 | 3.80 ± 1.53 | 2.23 ± 1.27 | 4.51 ± 1.91 |
| Spleen | 2.56 ± 0.92 | 4.62 ± 1.59 | 1.25 ± 0.26 | 6.98 ± 2.31 |
| Kidney | 4.52 ± 0.78 | 2.42 ± 0.49 | 1.91 ± 0.41 | 4.55 ± 1.42 |
| Lung | 3.49 ± 1.36 | 3.59 ± 1.72 | 0.66 ± 0.21 | 13.6 ± 4.51 |
| Blood | 12.8 ± 4.53 | 0.96 ± 0.44 | 1.13 ± 0.51 | 8.49 ± 3.72 |
| Stomach | 1.00 ± 0.27 | 12.0 ± 6.36 | 0.19 ± 0.07 | 48.0 ± 19.1 |
| Sm. Int. | 0.94 ± 0.34 | 13.2 ± 6.34 | 0.26 ± 0.05 | 34.4 ± 13.5 |
| Large Int. | 0.60 ± 0.11 | 18.5 ± 5.14 | 0.25 ± 0.06 | 34.6 ± 11.2 |
| Heart | 2.95 ± 1.26 | 4.41 ± 2.35 | 0.64 ± 0.30 | 15.4 ± 7.59 |
| Urine | 33.2 ± 42.7 | — | 2.84 ± 0.71 | 3.14 ± 1.21 |

TABLE 9

I-125-labeled hRS-7 × 734 Biodistribution in CALU-3 Tumor Bearing Nude Mice Pretargeted 48 hr Prior to Peptide Injection with 250 mg hRS-7 × m734, 136:1 bsAb/peptide Ratio. % ID/g and T/NT Ratios Determined 3 & 24 hr Post Injection of the Peptide.

| Tissue | 3 hr % ID/g | 3 hr T/NT | 24 hr % ID/g | 48 hr T/NT |
|---|---|---|---|---|
| Tumor | 10.9 ± 3.14 | — | 8.48 ± 2.77 | — |
| Liver | 0.19 ± 0.06 | 11.5 ± 4.82 | 0.10 ± 0.02 | 9.10 ± 1.61 |
| Spleen | 0.22 ± 0.07 | 9.79 ± 4.40 | 0.10 ± 0.06 | 12.2 ± 6.42 |
| Kidney | 0.29 ± 0.14 | 7.85 ± 3.09 | 0.13 ± 0.05 | 7.93 ± 2.80 |
| Lung | 0.27 ± 0.10 | 8.04 ± 2.69 | 0.09 ± 0.01 | 10.3 ± 1.84 |
| Blood | 0.18 ± 0.06 | 11.3 ± 2.40 | 0.05 ± 0.03 | 21.0 ± 6.42 |
| Stomach | 0.45 ± 0.29 | 5.36 ± 1.93 | 0.16 ± 0.06 | 6.52 ± 2.95 |
| Sm. Int. | 0.08 ± 0.02 | 24.4 ± 5.01 | 0.04 ± 0.01 | 26.5 ± 7.48 |
| Large Int. | 0.12 ± 0.03 | 17.7 ± 6.69 | 0.05 ± 0.01 | 21.0 ± 6.42 |
| Heart | 0.08 ± 0.02 | 24.5 ± 3.43 | 0.03 ± 0.01 | 35.4 ± 12.3 |
| Urine | 2.02 ± 2.61 | 7.46 ± 8.98 | 0.64 ± 0.22 | 1.51 ± 0.36 |

Example 23

Biodistribution of In-111-Labeled IMP 274 in GW-39 Tumor Bearing Nude Mice and in GW-39 Tumor Bearing Nude Mice Pretargeting with hMN-14×m734

Biodistribution of In-111-Labeled IMP 274 was determined in GW-39 Tumor Bearing Nude Mice and is summarized in Table 10. Biodistribution of In-111-Labeled IMP 274 in GW-39 Tumor Bearing Nude Mice pretargeted with hMN-14×m734 is shown in Tables 11.

TABLE 10

In-111-Labeled IMP 274 Biodistribution in GW-39 Tumor Bearing Nude Mice. ID/g Determined at 0.5 hr, 1 hr, 4 hr, and 24 hr Post Injection of the Peptide.

| Tissue | 0.5 hr | 1 hr | 4 hr | 24 hr |
|---|---|---|---|---|
| Tumor | 1.44 ± 0.37 | 0.91 ± 0.07 | 0.23 ± 0.05 | 0.12 ± 0.01 |
| Liver | 0.35 ± 0.07 | 0.29 ± 0.10 | 0.18 ± 0.03 | 0.20 ± 0.03 |
| Spleen | 0.34 ± 0.11 | 0.20 ± 0.04 | 0.08 ± 0.04 | 0.16 ± 0.01 |
| Kidney | 4.48 ± 0.83 | 2.75 ± 0.56 | 1.77 ± 0.32 | 1.65 ± 0.32 |
| Lung | 0.75 ± 0.21 | 0.39 ± 0.20 | 0.10 ± 0.01 | 0.07 ± 0.01 |
| Blood | 1.12 ± 0.24 | 0.60 ± 0.09 | 0.18 ± 0.10 | 0.06 ± 0.01 |
| Stomach | 0.22 ± 0.07 | 0.13 ± 0.02 | 0.09 ± 0.04 | 0.13 ± 0.12 |
| Sm. Int. | 0.35 ± 0.10 | 0.33 ± 0.06 | 0.54 ± 0.39 | 0.18 ± 0.08 |
| Large Int. | 0.31 ± 0.17 | 0.13 ± 0.06 | 0.17 ± 0.08 | 0.14 ± 0.06 |
| Heart | 0.41 ± 0.07 | 0.51 ± 0.52 | 0.07 ± 0.01 | 0.04 ± 0.02 |
| Urine | 1034 ± 563 | 1050 ± 549 | 4.35 ± 5.62 | 0.21 ± 0.05 |

TABLE 11

In-111-Labeled IMP 274 Biodistribution in GW-39 Tumor Bearing Nude Mice Pretargeted 24 hr Prior to Peptide Injection with hMN-14 × m734. ID/g Determined at 0.5 hr, 1 hr, 4 hr, and 24 hr Post Injection of the Peptide.

| Tissue | 0.5 hr | 1 hr | 4 hr | 24 hr |
|---|---|---|---|---|
| Tumor | 5.59 ± 2.01 | 5.96 ± 2.75 | 6.79 ± 3.33 | 6.16 ± 3.87 |
| Liver | 0.72 ± 0.17 | 0.43 ± 0.14 | 0.66 ± 0.11 | 0.43 ± 0.06 |
| Spleen | 0.67 ± 0.14 | 0.62 ± 0.15 | 0.71 ± 0.18 | 0.49 ± 0.17 |
| Kidney | 5.53 ± 1.42 | 2.90 ± 0.54 | 5.74 ± 1.11 | 2.46 ± 0.48 |
| Lungs | 1.65 ± 0.62 | 1.10 ± 0.29 | 1.39 ± 0.36 | 0.83 ± 0.22 |
| Blood | 3.40 ± 1.13 | 2.09 ± 0.72 | 3.18 ± 1.08 | 2.06 ± 0.75 |
| Stomach | 0.40 ± 0.11 | 0.38 ± 0.11 | 0.43 ± 0.16 | 0.23 ± 0.08 |
| Sm Int. | 0.60 ± 0.16 | 0.56 ± 0.10 | 0.60 ± 0.11 | 0.56 ± 0.07 |
| Large Int. | 0.28 ± 0.04 | 0.29 ± 0.03 | 0.24 ± 0.04 | 0.17 ± 0.04 |
| Heart | 0.96 ± 0.40 | 0.67 ± 0.16 | 0.78 ± 0.31 | 0.48 ± 0.15 |
| Urine | 1560 ± 105 | 227 ± 279 | 549 ± 22.2 | 170 ± 67.2 |

Example 24

Biodistribution of In-111-Labeled IMP 225 in GW-39 Tumor Bearing Nude Mice and in GW-39 Tumor Bearing Nude Mice Pretargeting with hMN-14×m734

Biodistribution of In-111'-Labeled IMP 225 was determined in GW-39 Tumor Bearing Nude Mice and is summarized in Table 12. Biodistribution of In-111-Labeled IMP 225 in GW-39 Tumor Bearing Nude Mice pretargeted with hMN-14×m734 is shown in Table 13.

TABLE 12

In-111-Labeled IMP 225 Biodistribution in GW-39 Tumor Bearing Nude Mice. ID/g Determined at 0.5 hr, 1 hr, 4 hr, and 24 hr Post Injection of the Peptide.

| Tissue | 0.5 hr | 1 hr | 4 hr | 24 hr |
|---|---|---|---|---|
| Tumor | 1.62 ± 0.45 | 1.03 ± 0.26 | 0.21 ± 0.03 | 0.10 ± 0.01 |
| Liver | 0.39 ± 0.05 | 0.26 ± 0.12 | 0.19 ± 0.05 | 0.14 ± 0.02 |
| Spleen | 0.21 ± 0.06 | 0.69 ± 1.19 | 0.11 ± 0.02 | 0.08 ± 0.02 |
| Kidney | 6.86 ± 1.41 | 4.18 ± 1.06 | 2.66 ± 0.69 | 1.21 ± 0.39 |
| Lung | 0.72 ± 0.21 | 0.54 ± 0.50 | 0.14 ± 0.04 | 0.04 ± 0.01 |
| Blood | 1.28 ± 0.23 | 0.62 ± 0.35 | 0.18 ± 0.04 | 0.04 ± 0.01 |
| Stomach | 0.27 ± 0.05 | 0.55 ± 0.37 | 0.14 ± 0.10 | 0.06 ± 0.03 |
| Sm. Int. | 0.39 ± 0.07 | 0.43 ± 0.11 | 0.16 ± 0.06 | 0.10 ± 0.02 |
| Large Int. | 0.32 ± 0.10 | 0.16 ± 0.07 | 0.47 ± 0.21 | 0.16 ± 0.04 |
| Heart | 0.30 ± 0.07 | 0.49 ± 0.68 | 0.06 ± 0.01 | 0.03 ± 0.01 |
| Urine | 1500 ± 263 | 552 ± 493 | 3.12 ± 2.23 | 0.21 ± 0.03 |

TABLE 13

In-111-Labeled IMP 225 Biodistribution in GW-39 Tumor Bearing Nude Mice Pretargeted 24 hr Prior to Peptide Injection with hMN-14 × m734. ID/g Determined at 0.5 hr, 1 hr, 4 hr, and 24 hr Post Injection of the Peptide.

| Tissue | 0.5 hr | 1 hr | 4 hr | 24 hr |
|---|---|---|---|---|
| Tumor | 7.84 ± 3.66 | 9.00 ± 2.08 | 5.71 ± 2.47 | 5.21 ± 1.27 |
| Liver | 0.99 ± 0.04 | 0.93 ± 0.25 | 0.61 ± 0.14 | 0.51 ± 0.10 |
| Spleen | 0.67 ± 0.10 | 0.43 ± 0.09 | 0.36 ± 0.19 | 0.34 ± 0.06 |
| Kidney | 10.6 ± 4.53 | 6.01 ± 2.70 | 2.84 ± 0.38 | 2.17 ± 0.80 |
| Lungs | 1.42 ± 0.33 | 0.89 ± 0.22 | 0.59 ± 0.49 | 0.16 ± 0.04 |
| Blood | 3.92 ± 0.20 | 2.98 ± 0.63 | 0.93 ± 0.26 | 0.23 ± 0.05 |
| Stomach | 0.85 ± 0.20 | 0.62 ± 0.31 | 0.19 ± 0.05 | 0.11 ± 0.02 |
| Sm Int. | 0.70 ± 0.31 | 0.49 ± 0.12 | 0.27 ± 0.07 | 0.21 ± 0.08 |
| Large Int. | 0.59 ± 0.24 | 0.29 ± 0.07 | 0.44 ± 0.13 | 0.21 ± 0.07 |
| Heart | 0.80 ± 0.09 | 0.58 ± 0.09 | 0.24 ± 0.10 | 0.16 ± 0.04 |
| Urine | 920 ± 322 | 1082 ± 541 | 6.44 | 2.12 ± 0.79 |

Example 25

In-Vivo Biodistribution of IMP 224 in BALB/c mice

Kits were reconstituted with 400 µCi In-111 in 0.5 mL water. The In-111 kit solution was incubated at room temperature for 10 min and then diluted with 1.5 mL of the cold indium containing pH 7.2, 0.5 M acetate buffer. The labeled peptide was analyzed by ITLC in saturated NaCl. The loose In-111 was at the top 20% of the ITLC strip.

Each mouse was injected with 100 µL (20 µCi) of the In-111 labeled peptide. The animals were anesthetized and sacrificed at 30 minutes, 1 hours, 2 hours, 4 hours, and 24 hours using three mice per time point. Blood, muscle, liver, lungs, kidneys, spleen, large intestine, small intestine, stomach, urine, and tail were collected and counted. The results of the biodistribution study are shown in Table 14.

TABLE 14

Biodistribution in BALB/c mice % ID/g of IMP 224
(Dox = N—NH—$C_6H_4$—CO—
Lys(DTPA)-Tyr-Lys(DTPA)—$NH_2$ $MH^+$ 1847
radiolabeled with In-111 and saturated with cold indium.

| Tissue | 30 min | 1 hr | 2 hr | 4 hr | 24 hr |
|---|---|---|---|---|---|
| Liver | 0.57 ± 0.04 | 0.31 ± 0.03 | 0.17 ± 0.03 | 0.17 ± 0.01 | 0.13 ± 0.02 |
| Spleen | 0.57 ± 0.18 | 0.27 ± 0.06 | 0.12 ± 0.01 | 0.11 ± 0.01 | 0.07 ± 0.00 |
| Kidney | 8.45 ± 1.79 | 5.36 ± 1.01 | 3.75 ± 0.52 | 4.03 ± 0.45 | 2.12 ± 0.17 |
| Lungs | 1.61 ± 0.34 | 0.99 ± 0.26 | 0.25 ± 0.02 | 0.17 ± 0.02 | 0.09 ± 0.02 |
| Blood | 1.44 ± 0.28 | 0.54 ± 0.12 | 0.12 ± 0.01 | 0.10 ± 0.01 | 0.02 ± 0.00 |
| Stomach | 0.61 ± 0.07 | 0.15 ± 0.07 | 0.05 ± 0.01 | 0.06 ± 0.02 | 0.04 ± 0.02 |
| Small Int. | 0.72 ± 0.08 | 0.37 ± 0.19 | 0.09 ± 0.01 | 0.09 ± 0.03 | 0.05 ± 0.01 |
| Large Int. | 0.59 ± 0.43 | 0.18 ± 0.04 | 0.38 ± 0.15 | 0.30 ± 0.06 | 0.08 ± 0.03 |
| Muscle | 0.51 ± 0.19 | 0.21 ± 0.08 | 0.03 ± 0.02 | 0.02 ± 0.00 | 0.01 ± 0.00 |
| Urine | 1553 | 1400 ± 421 | 19.1 | 1.72 ± 0.67 | 0.42 ± 0.18 |
| Tail | 3.66 ± 0.43 | 1.90 ± 0.09 | 0.46 ± 0.09 | 0.24 ± 0.03 | 0.58 ± 0.22 |

Example 26

In-Vivo Stability and Clearance of IMP 224

Kits were reconstituted with 4 mCi In-111 in 0.5 mL water. The In-111 kit was incubated at room temperature for 10 min and then diluted with 0.5 mL of the cold indium containing 0.5 M pH 7.2 acetate buffer. The labeled peptide was analyzed by ITLC in saturated NaCl. The loose In-111 was at the top 20% of the ITLC strip.

Each mouse was injected with 100 µL (400 µCi) of the In-111 labeled peptide. The animals were anesthetized and sacrificed at 30 min and 1 hr using two animals per time point. The serum and urine samples were collected, stored on ice, and sent on ice as soon as possible for HPLC analysis. The HPLC (by size exclusion chromatography) of the urine samples showed that the In-111 labeled peptide could still bind to the antibody. The reverse phase HPLC analysis showed that the radiolabeled peptide was excreted intact in the urine. The amount of activity remaining in the serum was too low to be analyzed by reverse phase HPLC due to the poor sensitivity of the detector. Doxorubicin has ~95% hepatobiliary clearance. Thus, by attaching the bis DTPA peptide in a hydrolyzeable manner, the biodistribution of the drug is altered to give ~100% renal excretion. This renders the drug far less toxic because all of the nontargeted drug is rapidly excreted intact. Clearance results are shown in Table 15.

TABLE 15

Activity Recovered in The Urine and Serum

| | 30 min | | 1 hr | |
|---|---|---|---|---|
| Tissue | Animal #1 | Animal #2 | Animal #1 | Animal #2 |
| Urine | 220 µCi | 133 µCi | 41.1 µCi | 273 µCi |
| Serum | 1.92 µCi | 3.64 µCi | 1.21 µCi | 1.27 µCi |

Example 27

Pretargeting Experiments with IMP 224 and IMP 225

A lyophilized kit of IMP 224 containing 10 micrograms of peptide was used. The kit was lyophilized in 2 mL vials and reconstituted with 1 mL sterile water. A 0.5 mL aliquot was removed and mixed with 1.0 mCi In-111. The In-111 kit solution was incubated at room temperature for 10 minutes then 0.1 mL was removed and diluted with 1.9 mL of the cold indium containing acetate buffer BM 8-12 in a sterile vial. The labeled peptide was analyzed by ITLC in saturated NaCl. The loose In-111 was at the top 20% of the ITLC strip.

Female nude mice (Taconic NCRNU, 3-4 weeks old) with GW 39 tumor xenografts were used for the pretargeting experiments. Tumors were 0.3-0.8 g. Each animal was injected with 100 microliters (5 Ci, 15 g, 1.5×$10^{-10}$ mol) of the I-125 labeled antibody F6×734-F(ab')$_2$.

Seventy two hours later, each mouse was injected with 100 L (10Ci) of the In-111 labeled peptide. The animals were anesthetized and sacrificed at 1 hour, 4 hours and 24 hours using five mice per time point. Tumor, blood, muscle, liver, lungs, kidneys, spleen, large intestine, small intestine, stomach, urine and tail were collected and counted.

The experiment was repeated with a lyophilized kit of IMP 225 $NH_2$-Lys(DTPA)-Tyr-Lys(DTPA)-Cys(Dox-$COCH_2$)-Ac (SEQ ID NO: 4) $MNa^+$ 1938, containing 11 micrograms of peptide. The biodistribution results are summarized in Tables 16-18.

TABLE 16

Biodistribution of In-111-IMP-224 in nude mice bearing GW-39 tumor xenografts, previously given F6 × 734-F(ab')₂ 72 h earlier. Data in % ID/g tissue. n = 5.

| Tissue | 1 h | | 4 h | | 24 h | |
|---|---|---|---|---|---|---|
| | I-125 | In-111 | I-125 | In-111 | I-125 | In-111 |
| GW-39 | 10.0 ± 1.5 | 10.3 ± 1.7 | 9.8 ± 2.6 | 11.0 ± 2.0 | 8.8 ± 1.2 | 9.7 ± 1.1 |
| Liver | 0.1 ± 0.0 | 0.4 ± 0.1 | 0.1 ± 0.0 | 0.3 ± 0.0 | 0.1 ± 0.0 | 0.3 ± 0.0 |
| Spleen | 0.1 ± 0.0 | 0.4 ± 0.1 | 0.1 ± 0.0 | 0.2 ± 0.0 | 0.1 ± 0.0 | 0.2 ± 0.0 |
| Kidney | 0.3 ± 0.1 | 3.5 ± 0.6 | 0.2 ± 0.0 | 2.8 ± 0.3 | 0.2 ± 0.0 | 1.9 ± 0.2 |
| Lungs | 0.2 ± 0.0 | 0.8 ± 0.2 | 0.2 ± 0.0 | 0.4 ± 0.0 | 0.2 ± 0.0 | 0.1 ± 0.0 |
| Blood | 0.4 ± 0.1 | 1.8 ± 0.6 | 0.4 ± 0.1 | 0.9 ± 0.2 | 0.4 ± 0.0 | 0.2 ± 0.0 |
| Stomach | 0.5 ± 0.2 | 0.8 ± 1.3 | 0.5 ± 0.2 | 0.1 ± 0.0 | 0.7 ± 0.2 | 0.1 ± 0.0 |
| Small Int. | 0.1 ± 0.0 | 0.5 ± 0.4 | 0.1 ± 0.0 | 0.2 ± 0.0 | 0.1 ± 0.0 | 0.1 ± 0.0 |
| Large Int. | 0.1 ± 0.0 | 0.1 ± 0.0 | 0.1 ± 0.0 | 0.3 ± 0.1 | 0.1 ± 0.1 | 0.1 ± 0.1 |
| Muscle | 0.0 ± 0.0 | 0.3 ± 0.2 | 0.0 ± 0.0 | 0.0 ± 0.0 | 0.0 ± 0.0 | 0.0 ± 0.0 |
| Urine | 1.1 ± 2.0 | 168 ± 106 | 1.8 ± 0.6 | 31.8 ± 31 | 0.9 ± 0.2 | 1.2 ± 0.2 |
| Tail | 0.1 ± 0.0 | 1.1 ± 0.2 | 0.1 ± 0.0 | 0.4 ± 0.1 | 0.2 ± 0.0 | 0.2 ± 0.0 |

TABLE 17

Biodistribution of In-111-IMP-224 in nude mice bearing GW-39 tumor xenografts, previously given F6 × 734-F(ab')₂ 72 h earlier. Data in tumor-to-normal organ ratios. n = 5.

| Tissue | 1 h | | 4 h | | 24 h | |
|---|---|---|---|---|---|---|
| | I-125 | In-111 | I-125 | In-111 | I-125 | In-111 |
| GW-39 | 1 | 1 | 1 | 1 | 1 | 1 |
| Liver | 85.4 ± 25 | 24.0 ± 5.9 | 81.8 ± 25 | 35.4 ± 6.9 | 61.1 ± 8.5 | 31.6 ± 5.8 |
| Spleen | 81.0 ± 34 | 28.7 ± 8.7 | 74.5 ± 25 | 44.7 ± 10 | 60.8 ± 8.6 | 47.0 ± 2.2 |
| Kidney | 39.7 ± 9.4 | 3.0 ± 0.5 | 57.1 ± 14 | 3.9 ± 0.5 | 39.6 ± 4.8 | 5.0 ± 0.5 |
| Lungs | 51.2 ± 10 | 13.4 ± 2.7 | 50.7 ± 10 | 30.1 ± 4.9 | 50.3 ± 10 | 69.0 ± 9.4 |
| Blood | 25.2 ± 8.3 | 6.1 ± 2.5 | 22.9 ± 7 | 12.8 ± 2.0 | 21.8 ± 4.2 | 41.8 ± 6.3 |
| Stomach | 21.0 ± 6.7 | 48.7 ± 37 | 22.1 ± 7 | 128 ± 46 | 14.9 ± 6.3 | 147 ± 39 |
| Small Int. | 137 ± 41 | 31.9 ± 18 | 128 ± 37 | 51.6 ± 14 | 102 ± 3.7 | 110 ± 13 |
| Large Int. | 136 ± 32 | 87.1 ± 35 | 130 ± 39 | 45.6 ± 19 | 113 ± 12 | 92.4 ± 38 |
| Muscle | 209 ± 86 | 38.6 ± 13 | 1396 ± | 727 ± 797 | 233 ± 42 | 283 ± 46 |
| Urine | 11.0 ± 23 | 0.3 ± 0.5 | 6.3 ± 4.2 | 0.71 ± 0.6 | 9.8 ± 1.9 | 8.3 ± 1.3 |
| Tail | 72.7 ± 20 | 9.4 ± 2.8 | 73.6 ± 20 | 26.4 ± 5.2 | 53.9 ± 10 | 55.9 ± 5.7 |

TABLE 18

Biodistribution of In-111-IMP-225 in nude mice bearing GW-39 tumor xenografts, previously given F6 × 734-F(ab')₂ 72 h earlier. Data in % ID/g tissue. n = 5.

| Tissue | 1 h | | 4 h | | 24 h | |
|---|---|---|---|---|---|---|
| | I-125 | In-111 | I-125 | In-111 | I-125 | In-111 |
| GW-39 | 6.2 ± 5.9 | 14.6 ± 14 | 10.5 ± 3.8 | 16.5 ± 4.8 | 8.3 ± 3.0 | 10.1 ± 2.3 |
| Liver | 0.1 ± 0.1 | 0.4 ± 0.2 | 0.2 ± 0.0 | 0.4 ± 0.1 | 0.1 ± 0.0 | 0.3 ± 0.1 |
| Spleen | 0.5 ± 0.7 | 1.6 ± 2.4 | 0.2 ± 0.0 | 0.4 ± 0.1 | 0.1 ± 0.0 | 0.4 ± 0.1 |
| Kidney | 0.3 ± 0.1 | 3.8 ± 0.9 | 0.3 ± 0.1 | 3.8 ± 0.4 | 0.2 ± 0.1 | 1.7 ± 0.3 |
| Lungs | 0.3 ± 0.1 | 0.8 ± 0.4 | 0.3 ± 0.0 | 0.6 ± 0.1 | 0.2 ± 0.1 | 0.2 ± 0.1 |
| Blood | 0.5 ± 0.1 | 2.0 ± 0.4 | 0.8 ± 0.4 | 1.3 ± 0.2 | 0.3 ± 0.1 | 0.4 ± 0.2 |
| Stomach | 0.1 ± 0.2 | 1.1 ± 0.9 | 0.8 ± 0.4 | 0.4 ± 0.2 | 0.3 ± 0.0 | 0.1 ± 0.0 |
| Small Int. | 0.1 ± 0.0 | 0.4 ± 0.1 | 0.1 ± 0.0 | 0.3 ± 0.2 | 0.1 ± 0.0 | 0.1 ± 0.0 |
| Large Int. | 0.1 ± 0.0 | 0.2 ± 0.0 | 0.1 ± 0.0 | 0.3 ± 0.1 | 0.1 ± 0.0 | 0.1 ± 0.0 |
| Muscle | 0.0 ± 0.0 | 0.3 ± 0.2 | 0.1 ± 0.0 | 0.2 ± 0.0 | 0.0 ± 0.0 | 0.1 ± 0.0 |
| Urine | 2.8 ± 3.4 | 110 ± 40 | 2.0 ± 1.0 | 13.5 ± 6.4 | 0.3 ± 0.3 | 0.7 ± 0.4 |
| Tail | 0.4 ± 0.2 | 1.2 ± 0.1 | 0.2 ± 0.0 | 0.8 ± 0.2 | 0.1 ± 0.1 | 0.5 ± 0.7 |

Example 28

Pretargeting in SCID Mice Inoculated with Daudi Cells

SCID mice were inoculated with Daudi (Burkitt's lymphoma) cells to produce disseminating disease. One group of mice received four i.p. injections of LL2x734 administered on days 1, 3, 7, and 9. This was followed by four i.p. injections of IMP-225 on days 2, 4, 8, and 10. A control group (no IMP-225) received IMP-225 alone on days 2, 4, 8, and 10. See FIG. 14A. Mice were observed daily for signs of paralysis as the endpoint of survival. Median percent survival was calculated and analyzed using Kaplan-Meier plots (log-rank analysis). See FIG. 14B.

Example 29

Synthesis of DTPA

DTPA may be synthesized as outlined in the schematics shown in FIGS. 15 and 16.

Three Step Method.

a. Synthesis of N-(2-((5-dibenzosuberyl)amino)ethyl)-1,2-ethanediamine, 3: Diethylenetriamine 1, 350 mL, was poured into a 1000 ml three neck flask, which had been flushed with nitrogen. The solution was cooled in an ice/salt bath to 3° C. The protecting group precursor 5-chlorodibenzosuberane 2 (15.017 g, $6.57 \times 10^{-2}$ mol) was slowly added by spoonfuls to the reaction mixture over a 15 min period under a positive pressure of nitrogen. The reaction was magnetically stirred and allowed to warm slowly to room temperature over 18 hr. The reaction was then cooled in the ice bath and 350 mL of water was slowly added (keeping the temperature below 50° C.). The reaction mixture was extracted with $4 \times 100$ mL $CH_2Cl_2$. The organic layers were combined and washed with $2 \times 100$ mL $H_2O$. The organic extracts were then dried over $Na_2SO_4$, filtered and concentrated on the rotary evaporator to provide 19.258 g (99% yield) of the yellow oily product. ESMS MH+ 296.

b. Synthesis of N,N,N',N"-Tetra((tert-butoxy-carbonyl)methyl)-N"-(2-((5-dibenzosuberyl)amino)ethyl)-1,2-ethanediamine 5: The crude N-(2-((5-dibenzosuberyl)amino) ethyl)-1,2-ethanediamine 3, 53 g ($1.8 \times 10^{-1}$ mol) was dissolved in 90 mL acetonitrile and placed under nitrogen. Diisopropylethyl amine, 71 mL ($5.49 \times 10^{-1}$ mol, 836 M %) was added and the solution was cooled in an ice bath. Tert-Butyl bromoacetate 4, 42 mL ($2.48 \times 10^{-1}$ mol, 446 M %) was added dropwise, and the reaction was allowed to warm slowly as it stirred overnight under nitrogen. The following day an additional 15 mL ($4.06 \times 10^{-2}$ mol, 62 M %) was added. The reaction was stirred overnight at room temperature. The reaction mixture then was concentrated on the rotary evaporator. The crude product was mixed with 200 mL ethyl acetate and extracted with $2 \times 100$ mL and $2 \times 50$ ml saturated sodium bicarbonate. The organic solution was dried over $Na_2SO_4$, filtered, and concentrated on the rotary evaporator to obtain 56 g of the crude product as an amber oil.

c. Synthesis of 1-tert-Butyl hydroxy 3,6,9-Tris((tert-butoxycarbonyl)methyl)-3,6,9-triazaundecanedioic Acid 7: The crude N,N,N',N"-Tetra((tert-butoxy-carbonyl)methyl)-N"-(2-((5-dibenzosuberyl)amino)ethyl)-1,2-ethanediamine 5 was mixed with 36.541.g ($3.97 \times 10^{-1}$ mol, 604 mol %) of glyoxylic acid monohydrate 6 and dissolved in 50 ml methanol. The Parr bottle was flushed with nitrogen and the catalyst 1.721 g (10% palladium on carbon) was added. After two days, an additional 0.999 g of catalyst was added. The mixture was placed under 50 PSI $H_2$ and was shaken at room temperature on the Parr shaker until the reaction was complete as judged by reverse phase HPLC (5 days). The reaction mixture was filtered through celite to remove the catalyst. The celite was washed with methanol. The filtrate was concentrated under reduced pressure on the rotary evaporator. The crude product was dissolved in 200 ml ether and washed with 100 ml $H_2O$ and 50 ml $H_2O$. The organic layer was then extracted with $2 \times 50$ ml portions of 1 M citric acid. The citric acid extract formed three layers. The bottom two layers were separated from the ether layer. Hexanes, 100 mL, were added to the ether layer and the organic layer was extracted with an additional 50 mL of 1 M citric acid. The combined citric acid extracts were then extracted with 100 mL hexanes. The water extracts and the citric acid extracts were combined and carefully neutralized to ~pH 8.0 with $Na_2CO_3$. The basified solution was extracted with $2 \times 200$ mL ethyl acetate. The organic extracts were dried over $Na_2SO_4$, filtered and concentrated under reduced pressure on the rotary evaporator. The crude product was mixed with 26.302 g of glyoxylic acid, 25 mL diisopropylethylamine, 2.147 g 10% Pd/C, and 50 mL MeOH. The mixture was shaken under 50 PSI $H_2$ for two days. The reaction mixture was filtered through celite and then concentrated under reduced pressure on the rotary evaporator. The crude product was dissolved in 200 mL ethyl acetate and extracted with $2 \times 100$ mL saturated $NaHCO_3$. The organic layer was washed with 100 mL 1 M $NaH_2PO_4$ and dried over $Na_2SO_4$. The reaction mixture was filtered and concentrated to provide 22.2 g of the crude product as a yellow oil. The crude product was purified by pouring the crude product onto a pad of flash silica % full in a 600 mL sintered glass funnel and eluting with a gradient of solvents. The funnel was eluted with 200 mL portions of $4 \times 100\%$ hexanes, $4 \times 75:25$ hexanes/ethyl acetate, $4 \times 1:1$ hexanes/ethyl acetate, $4 \times 25:75$ hexanes/ethyl acetate, $4 \times 100\%$ ethyl acetate, $3 \times 100\%$ $CHCl_3$, and $7 \times 95:5$ $CHCl_3/MeOH$. The oily amber product, 17.648 g (45% yield) was found in the 95:5 $CHCl_3/MeOH$ fractions (3 to 7).

Four Step Method.

a. Synthesis of N-(2-((5-dibenzosuberyl)amino)ethyl)-1, 2-ethanediamine, 3. Dithethylenetriamine 1, 250 mL, was placed in a one liter three neck round bottom flask equipped with a magnetic stir bar. The solution was placed under an atmosphere of nitrogen and cooled in an ice bath to 4° C. The 12.108 g ($5.29 \times 10^{-2}$ mol) of 5-chlorodibenzosuberane 2 was added in spoonfuls over 10 min. The reaction was allowed to slowly warm to room temperature and stir for 2.5 days. The reaction was then cooled in an ice bath and 350 mL of water was added. The solution was extracted with $4 \times 100$ mL $CH_2Cl_2$. The organic layers were combined and washed with $2 \times 100$ mL water. The organic layer was dried over sodium sulfate, filtered and concentrated on the rotary evaporator to afford 15.268 g (97.8% yield) of the crude product as an oil.

b. Synthesis of N,N,N',N"-Tetra((tert-butoxy-carbonyl)methyl)-N"-(2-((5-dibenzosuberyl)amino)ethyl)-1,2-ethanediamine 5. The entire crude product from the previous reaction 3 was dissolved in 75 mL of acetonitrile. Diisopropylethylamine, 68 mL was added to the reaction solution, which was flushed with nitrogen and cooled in an ice bath. tert-Butyl bromoacetate 4, 40 mL ($2.71 \times 10^{-1}$, 523 mol %) was added dropwise to the reaction solution and the solution was allowed to slowly warm to room temperature as it stirred overnight. The next day an additional 7.5 mL of tert-butyl bromoacetate 4 was added to drive the reaction to completion. The reaction was stirred at room temperature for one more day and then concentrated under reduced pressure on the rotary evaporator. Ethyl acetate, 200 mL was added and extraction was performed with 3×100 mL of saturated sodium bicarbonate solution. The organic layer was dried over sodium sulfate and concentrated under reduced pressure to obtain an amber oil. The oil was then further concentrated at 80° C. under hi-vacuum on the rotary evaporator to obtain 40.938 g of the crude product as an amber oil.

c. Synthesis of N,N,N',N"-Tetra((tert-butoxy-carbonyl)methyl)-N"-(2-(amino)ethyl)-1,2-ethanediamine. The crude product, 40.873 g, was dissolved in 40 mL methanol and placed in a 500 mL Parr hydrogenation bottle. Citric acid, 10.505 g was then added and the bottle was purged with nitrogen. The catalyst, 1.551 g of 10% palladium on activated carbon, was then added to the Parr bottle. The mixture was then placed on the Parr shaker under 50 PSI $H_2$. The hydrogenation was nearly complete after shaking for two days under 50 PSI $H_2$ but the reaction was allowed to proceed for an additional two days before it was removed from the Parr shaker. The reaction mixture was filtered through celite. The filtrate was concentrated on the rotary evaporator and then dissolved in 200 mL diethylether. The solution was carefully mixed with 300 mL of a saturated $NaHCO_3$ solution. The ether layer and the bicarbonate layers were separated. The bicarbonate layer was back extracted with 2×50 mL of ether. The ether layers were combined and mixed with 300 mL hexanes. The organic layer was then extracted with 3×50 mL 1 M citric acid. The citric acid extracts were combined and extracted with 2×100 mL portions of 1:1 ether/hexanes solution (to remove traces of suberane). Sodium carbonate, 16.322 g was slowly added to the citric acid solution with 100 mL of ethyl acetate on top of the aqueous layer. Additional sodium carbonate was added until the pH was adjusted to pH 8 by pH paper. The solution was then extracted with 3×100 mL ethyl acetate. The ethyl acetate extracts were combined and dried over sodium sulfate. The solution was filtered and concentrated on the rotary evaporator to afford 21.755 g (75% yield) of the crude product as a yellow oil. The crude product was dissolved in 25 mL of ether and placed on a pad of flash silica ¾ full in a 600 mL sintered glass funnel. The funnel was eluted with 200 mL portions of 4×100% hexanes, 4×9:1 hexanes/ethyl acetate, 4×75:25 hexanes/ethyl acetate, 8×50:50 hexanes/ethyl acetate, 4×25:75 hexanes/ethyl acetate and 4×100% ethyl acetate. The product appears to be present in all the fractions from 75:25 hexanes/ethyl acetate to 100% ethyl acetate. The HPLC shows increased levels of impurities in the 75:25 hexanes/ethyl acetate fractions as well as the first three 50:50 ethyl acetate/hexanes fractions. These fractions contain about 5.9 g of material. The remaining fractions that contain product were combined to afford 11.332 g ($MH^+$ 560, 39% yield) of the oily product.

d. Synthesis of 1-tert-butoxy 3,6,9-Tris((tert-butoxycarbonyl)methyl)-3,6,9-triazaundecanedioic Acid 8. The purified product from the previous reaction 11.332 g was dissolved in 40 mL methanol and placed under an atmosphere of nitrogen in a 500 mL Parr bottle. Glyoxylic acid monohydrate 6, 13.813 g was added to the solution followed by 1.102 g of 10% palladium on activated carbon. The bottle was placed on the Parr shaker under 50 PSI $H_2$. The mixture was shaken under overnight under $H_2$ and an aliquot tested the following day revealed that the reaction was ~90% complete. The reaction mixture was charged with 0.685 g of fresh catalyst and returned to the hydrogenator for three additional days at 50 PSI $H_2$. The reaction solution was then filtered through celite, concentrated on the rotary evaporator and dissolved in 200 mL ethyl acetate and dissolved in 200 mL ethyl acetate. The ethyl acetate solution was carefully mixed with 175 mL of saturated $NaHCO_3$ solution. The organic layer was washed with 100 mL water followed by a wash with 100 mL 1 M $NaH_2PO_4$ and finally 100 mL saturated NaCl. The organic layer was dried over sodium sulfate, filtered and concentrated on the rotary evaporator to afford 10.444 g (84% yield) of a yellow oil.

Example 30

Activating and Conjugating DTPA

The DTPA, 5 g was dissolved in 40 mL 1.0 M tetrabutylammonium hydroxide in methanol. The methanol was removed under hi-vacuum to obtain a viscous oil. The oil was dissolved in 50 mL DMF and the volatile solvents were removed under hi-vacuum on the rotary evaporator. The DMF treatment was repeated two more times. The viscous oil was then dissolved in 50 ml DMF and mixed with 5 g HBTU. An 8 ml aliquot of the activated DTPA solution was then added to the resin which was vortex mixed for 14 hr. The DTPA treatment was repeated until the resin gave a negative test for amines using the Kaiser test. Alternatively, DTPA Tetra-t-butyl ester could be used with conventional coupling agents such as DIC and HBTU. (See Arano Y et al., *J Med Chem*. 1996 Aug. 30;39(18): 3451-60).

Example 31

Conjugation of a Carboxylesterase to di-DTPA-Peptide

Carboxylesterase (5 mg) in 0.2 M phosphate buffer, pH 8.0, is treated with a five-fold molar excess of the cross-linking agent sulfo-succinimidyl-[4-maleimidomethyl]-cyclohexane-1-carboxylate (sulfo-SMCC). After stirring two hours at room temperature, the activated enzyme is separated from low molecular weight contaminants using a spin-column of G-25 Sephadex and equilibrated in 0.1 M phosphate buffer, pH 7, containing 1 mM EDTA. The tetrapeptide N-acetyl-Cys-Lys(DTPA)-Tyr-Lys(DTPA)-$NH_2$ (SEQ ID NO: 1) (ten-fold molar excess) is added to the activated enzyme and dissolved in the same buffer as used in the spin-column. After stirring for one hour at room temperature, the peptide carboxylesterase conjugate is purified from unreacted peptide by spin-column chromatography on G-25 Sephadex in 0.25 M acetate buffer, pH 6.0. Successful conjugation is demonstrated by indium-111 labeling of an aliquot of the conjugate, and analysis by size-exclusion HPLC.

Example 32

Preparation of a Carboxylesterase-DTPA Conjugate

Two vials of rabbit liver carboxylesterase (SIGMA; protein content ~17 mg) are reconstituted in 2.2 ml of 0.1 M sodium phosphate buffer, pH 7.7 and mixed with a 25-fold molar excess of CA-DTPA using a freshly prepared stock solution (~25 mg/ml) of the latter in DMSO. The final concentration of DMSO in the conjugation mixture is 3% (v/v). After 1 hour of incubation, the mixture is pre-purified on two 5-mL spin-columns (Sephadex G50/80 in 0.1 M sodium phosphate pH 7.3) to remove excess reagent and DMSO. The eluate is purified on a TSK 3000G Supelco column using 0.2 M sodium phosphate pH 6.8 at 4 ml/min. The fraction containing conjugate is concentrated on a Centricon-10™ concentrator, and buffer-exchanged with 0.1 M sodium acetate pH 6.5. Recovery: 0.9 ml, 4.11 mg/ml (3.7 mg). Analytical HPLC analysis using standard conditions, with in-line UV detection, revealed a major peak with a retention time of 9.3 min and a minor peak at 10.8 min in 95-to-5 ratio. Enzymatic analysis showed 115 enzyme units/mg protein, comparable to unmodified carboxylesterase. Mass spectral analyses (MALDI mode) of both unmodified and DTPA-modified CE shows an average DTPA substitution ratio near 1.5. A metal-binding assay using a known excess of indium spiked with radioactive indium confirmed the DTPA:enzyme ratio to be 1.24 and 1.41 in duplicate experiments. Carboxylesterase-DTPA is labeled with In-111 acetate at a specific activity of 12.0 mCi/mg, then treated with excess of non-radioactive indium acetate, and finally treated with 10 mM EDTA to scavenge off excess non-radioactive indium. Incorporation by HPLC and ITLC analyses is 97.7%. A HPLC sample is completely complexed with a 20-fold molar excess of bi-specific antibody hMN-14 Fab'×734 Fab', and the resultant product further complexes with WI2 (anti-ID to hMN-14), with the latter in 80-fold molar excess with respect to bi-specific antibody.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compounds/compositions described herein as presently representative of preferred embodiments are exemplary and are not intended as limitations on the scope of the invention. Changes therein and other uses will occur to those skilled in the art, which are encompassed within the invention.

It will be readily apparent to one skilled in the art that varying substitutions and modifications may be made to the invention disclosed herein without departing from the scope and spirit of the invention. For example, a variety of different binding pairs can be utilized, as well as a variety of different therapeutic and diagnostic agents. Thus, such additional embodiments are within the scope of the present invention.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

The invention claimed is:

1. A method of preparing a polyalkylene polyamine substituted at one or more nitrogen positions with an alkyl carboxylate group, comprising:

reacting a polyalkylene polyamine having a formula $NH_2$—R with a molecule having a formula Z-$X^1$ to form a molecule (I) having a formula Z-NH—R, wherein R is a straight chain or branched alkyl group that has between 1 and 20 carbon atoms and includes one or more nitrogen atoms, Z is a protecting group, and $X^1$ is a leaving group;

reacting molecule (I) with a molecule (II) having a formula:

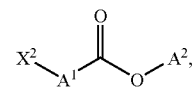

wherein $X^2$ is a leaving group and $A^1$ and $A^2$ are straight chain or branched alkyl groups having between 1 and 12 carbon atoms, to form a molecule (III) having a formula:

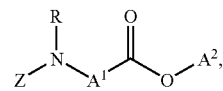

wherein one or more nitrogen atoms within R are optionally substituted with a molecule having the formula:

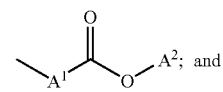

removing and replacing the protecting group Z;

wherein Z is removed and replaced by reacting molecule (III) with $H_2$, palladium and glyoxylic acid monohydrate.

2. The method of claim 1, wherein the polyalkylene polyamine has the formula $NH_2$—$((CH_2)_V$—$NH$—$(CH_2)_W)_Y$—$NH^2$, wherein V, W, and Y are between 1 and 8 and are the same or different.

3. The method of claim 2, wherein the polyalkylene polyamine is diethylenetriamine.

4. The method of claim 1, wherein the protecting group Z comprises one or more aromatic groups.

5. The method of claim 4, wherein the protecting group Z comprises one or more benzene rings.

6. The method of claim 4, wherein the protecting group Z has the formula

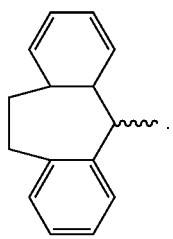

7. The method of claim 1, wherein removing and replacing Z comprises reacting molecule (III) with $H_2$ and palladium to form a molecule (IV) in a first step and reacting molecule (IV) with $H_2$ and palladium and glyoxylic acid monohydrate in a second step and wherein molecule (IV) has a formula:

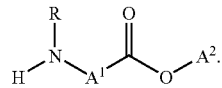

8. The method of claim 1, wherein Z is removed and replaced with a substituent having the formula:

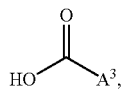

wherein $A^3$ is $CH_2$ to form a molecule (V) having a formula:

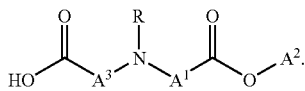

9. The method of claim 8, wherein molecule (V) has the formula:

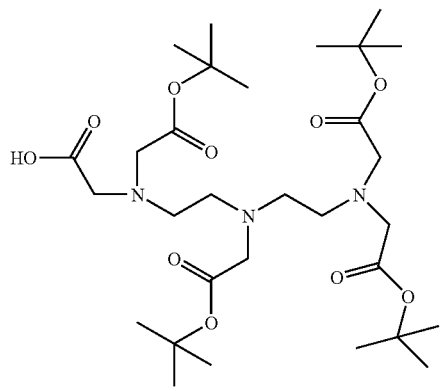

10. The method of claim 1, wherein $X^1$ is halogen, mesylate or tosylate.

11. The method of claim 10, wherein $X^1$ is bromide or chloride.

12. The method of claim 1, wherein $X^2$ is halogen, mesylate or tosylate.

13. The method of claim 12, wherein $X^2$ is bromide or chloride.

14. The method of claim 1, wherein $A^1$ is $—CH_2—$.

15. The method of claim 1, wherein $A^2$ is tert-butyl.

* * * * *